(12) United States Patent
Mudd et al.

(10) Patent No.: US 11,332,500 B2
(45) Date of Patent: May 17, 2022

(54) HETEROTANDEM BICYCLIC PEPTIDE COMPLEXES

(71) Applicant: BicycleTx Limited, Cambridge (GB)

(72) Inventors: Gemma Mudd, Cambridge (GB); Punit Upadhyaya, Lexington, MA (US); Kevin McDonnell, Lexington, MA (US)

(73) Assignee: BICYCLETX LIMITED, Cambridge (GB)

( * ) Notice: Subject to any disclaimer, the term of this patent is extended or adjusted under 35 U.S.C. 154(b) by 0 days.

(21) Appl. No.: 17/062,662

(22) Filed: Oct. 5, 2020

(65) Prior Publication Data

US 2021/0101937 A1  Apr. 8, 2021

Related U.S. Application Data

(60) Provisional application No. 62/910,129, filed on Oct. 3, 2019.

(51) Int. Cl.
*C07K 11/00* (2006.01)
*C07K 11/02* (2006.01)

(52) U.S. Cl.
CPC .................................. *C07K 11/02* (2013.01)

(58) Field of Classification Search
CPC .... A61K 38/00; A61K 47/543; A61K 47/545; A61K 47/60; A61K 47/64; A61P 35/00; C07K 11/02; C07K 14/70503; C07K 14/70532; C07K 14/70578; C07K 14/715
See application file for complete search history.

(56) References Cited

U.S. PATENT DOCUMENTS

| | | |
|---|---|---|
| 10,875,894 B2 | 12/2020 | Chen et al. |
| 10,919,937 B2 | 2/2021 | Beswick et al. |
| 2014/0249292 A1 | 9/2014 | Tite et al. |
| 2019/0184025 A1 | 6/2019 | Chen et al. |
| 2019/0307836 A1 | 10/2019 | Keen et al. |
| 2019/0389906 A1 | 12/2019 | Beswick et al. |
| 2020/0255477 A1 | 8/2020 | Chen et al. |
| 2020/0338203 A1 | 10/2020 | Chen et al. |
| 2020/0354406 A1 | 11/2020 | Stephen et al. |
| 2021/0040154 A1 | 2/2021 | Mudd et al. |
| 2021/0069287 A1 | 3/2021 | Mudd et al. |
| 2021/0101932 A1 | 4/2021 | Chen et al. |
| 2021/0101933 A1 | 4/2021 | Chen et al. |
| 2021/0101937 A1 | 4/2021 | Mudd et al. |
| 2021/0147484 A1 | 5/2021 | Beswick et al. |
| 2021/0261620 A1 | 8/2021 | Teufel et al. |
| 2021/0269480 A1 | 9/2021 | Beswick et al. |

FOREIGN PATENT DOCUMENTS

| | | |
|---|---|---|
| WO | WO-2004/077062 A2 | 9/2004 |
| WO | WO-2010/089115 A1 | 8/2010 |
| WO | WO-2012/057624 A1 | 5/2012 |
| WO | WO-2016/067035 A1 | 5/2016 |
| WO | WO-2017/173408 A1 | 10/2017 |
| WO | WO-2017/182672 A1 | 10/2017 |
| WO | WO-2017/191460 A1 | 11/2017 |
| WO | WO-2018/156740 A1 | 8/2018 |
| WO | WO-2019/025811 A | 2/2019 |
| WO | WO-2019/122860 A1 | 6/2019 |
| WO | WO-2019/122861 A1 | 6/2019 |
| WO | WO-2019/122863 A1 | 6/2019 |
| WO | WO-2019/162682 A1 | 8/2019 |
| WO | WO-2019/193328 A1 | 10/2019 |
| WO | WO-2019/243313 A1 | 12/2019 |
| WO | WO-2019/243832 A1 | 12/2019 |
| WO | WO-2019/243833 A1 | 12/2019 |
| WO | WO-2020/084305 A1 | 4/2020 |
| WO | WO-2020/128526 A1 | 6/2020 |
| WO | WO-2020/201753 A1 | 10/2020 |
| WO | WO-2020/225577 A1 | 11/2020 |
| WO | WO-2021/019243 A1 | 2/2021 |
| WO | WO-2021/019244 A1 | 2/2021 |
| WO | WO-2021/019245 A1 | 2/2021 |
| WO | WO-2021/019246 A1 | 2/2021 |
| WO | WO-2021/028686 A1 | 2/2021 |
| WO | WO-2021/064428 A1 | 4/2021 |

OTHER PUBLICATIONS

Bicycle Therapeutics, Press Release—MarketWatch.com, Apr. 2018.
Chen et al., "Peptide Ligands Stabilized by Small Molecules," Angew. Chem. Int. Ed., 2014, vol. 53, pp. 1602-1606.
Gfeller et al., "Current tools for predicting cancer-specific T cell immunity," Oncoimmunology, 5(7): 1-9, (2016).
International Search Report and Written Opinion for International Application No. PCT/GB2019/050951, dated Jul. 4, 2019, 11 pages.
Liu et al., "Abstract 3642: Tumor antigen expression-dependent activiation of the CD137 costimulatory pathway by bispecific DART proteins," American Association for Cancer Research, 77(13): supplement Jul. 2017, 1-4, (2017).
Loktev et al., "Multicyclic Peptides as Scaffolds for the Development of Tumor Targeting Agents," Current Medicinal Chemistry, 2017, vol. 24, pp. 2141-2155.
Morrison, "Chemical Strategies for Bicyclic Peptide Formation," Univ. of Leeds, Sep. 2015, pp. 1-60.
Mulder et al., "Scaffold Optimization in Discontinuous Epitope Containing Protein Mimics of gp120 Using Smart Libraries," Org. Biomol. Chem. 2013, vol. 11, pp. 2676-2684.

(Continued)

*Primary Examiner* — Aradhana Sasan
*Assistant Examiner* — Mercy H Sabila
(74) *Attorney, Agent, or Firm* — Dechert LLP; Andrea L. C. Reid; Gang Wang

(57) ABSTRACT

The present invention relates to heterotandem bicyclic peptide complexes which comprise a first peptide ligand, which binds to a component present on a cancer cell, conjugated via a linker to a second peptide ligand, which binds to a component present on an immune cell. The invention also relates to the use of said heterotandem bicyclic peptide complexes in preventing, suppressing or treating cancer.

21 Claims, No Drawings

Specification includes a Sequence Listing.

(56) References Cited

OTHER PUBLICATIONS

International Search Report and Written Opinion for International Application No. PCT/GB2020/051827, dated Nov. 3, 2020, 11 Pages.
Pickens et al., "Practical Considerations, Challenges and Limitations of Bioconjugation via Azide-Alkyne Cycloaddition," Bioconjugate Chem., 2018, vol. 29, pp. 686-701.
Rhodes et al., Chemistry—A European Journal, vol. 23, No. 52, Sep. 2017, pp. 12690-12703.
Smeenk et al., "Reconstructing the Discontinuous and Conformational β1/β3-Loop Binding Site on hFSH/hCG by Using Highly Constrained Multicyclic Peptides," ChemBioChem 2015, vol. 16, pp. 91-99.
Upadhyaya, "Activation of CD137 Using Multivalent and Tumour Targeted Bicyclic Peptides," XP055669343, URL:https://www.bicycletherapeutics.com/wp-content/uploads/PU_2019-Peptide-Congress_publication.pdf, Peptide Congress, Apr. 25, 2019, 25 Pages.

HETEROTANDEM BICYCLIC PEPTIDE COMPLEXES

FIELD OF THE INVENTION

The present invention relates to heterotandem bicyclic peptide complexes which comprise a first peptide ligand, which binds to a component present on a cancer cell, conjugated via a linker to a second peptide ligand, which binds to a component present on an immune cell. The invention also relates to the use of said heterotandem bicyclic peptide complexes in preventing, suppressing or treating cancer.

REFERENCE TO SEQUENCE LISTING

A Sequence Listing is being submitted electronically via EFS in the form of a text file, created Dec. 9, 2020, and named 176531_SL_20201209.txt (35,338 bytes), the contents of which are incorporated herein by reference in their entirety.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al.

(2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a heterotandem bicyclic peptide complex comprising:
(a) a first peptide ligand which binds to a component present on a cancer cell; conjugated via a linker to
(b) a second peptide ligand which binds to a component present on an immune cell;
wherein each of said peptide ligands comprise a polypeptide comprising at least three reactive groups, separated by at least two loop sequences, and a molecular scaffold which forms covalent bonds with the reactive groups of the polypeptide such that at least two polypeptide loops are formed on the molecular scaffold, characterised in that said heterotandem bicyclic peptide complex comprises the following first and second peptide ligands:

| Heterotandem Complex No. | First Peptide | Second Peptide |
|---|---|---|
| BCY12229 | [Ac]D[HArg]CSAGWLTMCQKLHLCPSH (SEQ ID NO: 1; BCY11865) | Ac-C[tBuAla]PE[D-Lys(PYA)]PYCFADPY[Nle]CA (SEQ ID NO: 67; BCY8928) |
| BCY12230 | [Ac]D[HArg]CSKGWLTMCQK(Ac)LHLCPSH (SEQ ID NO: 2; BCY11866) | Ac-C[tBuAla]PE[D-Lys(PYA)]PYCFADPY[Nle]CA (SEQ ID NO: 67; BCY8928) |
| BCY12231 | [Ac]D[HArg]CSAGWLTKCQK(Ac)LHLCPSH (SEQ ID NO: 3; BCY11867) | Ac-C[tBuAla]PE[D-Lys(PYA)]PYCFADPY[Nle]CA (SEQ ID NO: 67; BCY8928) |
| BCY12232 | [Ac]D[HArg]CSAGWLTMCKK(Ac)LHLCPSH (SEQ ID NO: 4; BCY11868) | Ac-C[tBuAla]PE[D-Lys(PYA)]PYCFADPY[Nle]CA (SEQ ID NO: 67; BCY8928) |
| BCY12242 | [Ac]D[HArg]CSAGWLTMCQK(Ac)LKLCPSH (SEQ ID NO: 5; BCY11869) | Ac-C[tBuAla]PE[D-Lys(PYA)]PYCFADPY[Nle]CA (SEQ ID NO: 67; BCY8928) |

-continued

| Heterotandem Complex No. | First Peptide | Second Peptide |
|---|---|---|
| BCY12375 | Ac-SDKCSAGWLTMCQK[PYA]LHLCPSH (SEQ ID NO: 6; BCY10861) | [Ac]C[tBuAla]EE(dK)PYCFADPY[Nle]C[Dap(PYA)] (SEQ ID NO: 68; BCY12023) |
| BCY12663 | [Ac]SD[HArg]CSAGWLTMCQ[HArg]LHLCPSHK (SEQ ID NO: 7; BCY12479) | Ac-C[tBuAla]PE[D-Lys(PYA)]PYCFADPY[Nle]CA (SEQ ID NO: 67; BCY8928) |
| BCY12796 | [Ac]SD[HArg]CSAGWLTMC[HArg]QLNLCPSHK (SEQ ID NO: 8; BCY12477) | Ac-C[tBuAla]PE[D-Lys(PYA)]PYCFADPY[Nle]CA (SEQ ID NO: 67; BCY8928) |
| BCY12021 | Ac-SDKCSAGWLTMCQK[PYA]LHLCPSH (SEQ ID NO: 9; BCY10861) | [Ac]C[tBuAla]PE[dK]PYCFADPY[Nle]C[Dap(PYA)] (SEQ ID NO: 69; BCY11144) |
| BCY12233 | [PYA]A[HArg]DC[HyP]LVNPLCLHP[dD]W[HArg]C (SEQ ID NO: 10; BCY11813) | Ac-C[tBuAla]PE[D-Lys]PYCFADPY[Nle]CA (SEQ ID NO: 70; BCY8920) |
| BCY12234 | [Ac]A[HArg]DC[HyP]LVNPLCLHP[dD]W[HArg]CK(PYA) (SEQ ID NO: 11; BCY11814) | Ac-C[tBuAla]PE[D-Lys]PYCFADPY[Nle]CA (SEQ ID NO: 70; BCY8920) |
| BCY12235 | [Ac]A[HArg]DC[HyP]LVNPLCLK(PYA)P[dD]W[HArg]C (SEQ ID NO: 12; BCY11815) | Ac-C[tBuAla]PE[D-Lys]PYCFADPY[Nle]CA (SEQ ID NO: 70; BCY8920) |
| BCY12236 | [Ac]A[HArg]DC[HyP]K(PYA)VNPLCLHP[dD]W[HArg]C (SEQ ID NO: 13; BCY11816) | Ac-C[tBuAla]PE[D-Lys]PYCFADPY[Nle]CA (SEQ ID NO: 70; BCY8920) |
| BCY12237 | [Ac]A[HArg]DC[HyP]LVNPLCK(PYA)HP[dD]W[HArg]C (SEQ ID NO: 14; BCY11817) | Ac-C[tBuAla]PE[D-Lys]PYCFADPY[Nle]CA (SEQ ID NO: 70; BCY8920) |
| BCY12711 | A[HArg]DC[HyP]LVNPLCLHP[dD]W[HArg]C (SEQ ID NO: 15; BCY9594) | [Ac]C[tBuAla]EE[dK(PYA)]PYCFADPY[Nle]C (SEQ ID NO: 71; BCY12143) |
| BCY12712 | A[HArg]DC[HyP]LVNPLCLHP[dD]W[HArg]C (SEQ ID NO: 15; BCY9594) | [Ac]C[tBuAla]PE[dK(PYA)]PYCFADPY[Nle]C (SEQ ID NO: 72; BCY12149) |
| BCY12713 | A[HArg]DC[HyP]LVNPLCLHP[dD]W[HArg]C (SEQ ID NO: 15; BCY9594) | [Ac]C[tBuAla]PE[dK(PYA)]PYCFANPY[Nle]C (SEQ ID NO: 73; BCY12147) |
| BCY12714 | A[HArg]DC[HyP]LVNPLCLHP[dD]W[HArg]C (SEQ ID NO: 15; BCY9594) | [Ac]C[tBuAla]PE[dK(PYA)]PYCFAEPY[Nle]C (SEQ ID NO: 74; BCY12145) |
| BCY12715 | A[HArg]DC[HyP]LVNPLCLHP[dD]W[HArg]C (SEQ ID NO: 15; BCY9594) | [Ac]C[tBuAla]PE[dK(PYA)]PYCFA[Aad]PY[Nle]C (SEQ ID NO: 75; BCY12146) |
| BCY12717 | A[HArg]DC[HyP]LVNPLCLHP[dD]W[HArg]C (SEQ ID NO: 15; BCY9594) | [Ac]C[tBuAla]PE[dK(PYA)]PYCFADPY[Nle][Cysteamine] (SEQ ID NO: 76; BCY12352) |
| BCY12718 | A[HArg]DC[HyP]LVNPLCLHP[dD]W[HArg]C (SEQ ID NO: 15; BCY9594) | [3-mercaptopropionic acid][tBuAla]PE[dK(PYA)]PYCFADPY[Nle]C (SEQ ID NO: 77; BCY12353) |
| BCY12719 | A[HArg]DC[HyP]LVNPLCLHP[dD]W[HArg]C (SEQ ID NO: 15; BCY9594) | [3-mercaptopropionic acid][tBuAla]PE[dK(PYA)]PYCFADPY[Nle][Cysteamine] (SEQ ID NO: 78; BCY12354) |
| BCY12720 | A[HArg]DC[HyP]LVNPLCLHP[dD]W[HArg]C (SEQ ID NO: 15; BCY9594) | Palmitic acid-yGly-yGlu-C[tBuAla]PE[dK(PYA)]PYCFADPY[Nle]C (SEQ ID NO: 79; BCY12360) |
| BCY12961 | [Ac]A[HArg]DC[HyP]LVNPLCLHP[dD]W[HArg]CK (SEQ ID NO: 16; BCY12734) | Ac-C[tBuAla]PE[D-Lys(PYA)]PYCFADPY[Nle]CA (SEQ ID NO: 67; BCY8928) |
| BCY12962 | [Ac]A[HArg]DC[HyP]LVNPLCLKP[dD]W[HArg]C (SEQ ID NO: 17; BCY12735) | Ac-C[tBuAla]PE[D-Lys(PYA)]PYCFADPY[Nle]CA (SEQ ID NO: 67; BCY8928) |
| BCY12963 | [Ac]A[HArg]DC[HyP]KVNPLCLHP[dD]W[HArg]C (SEQ ID NO: 18; BCY12736) | Ac-C[tBuAla]PE[D-Lys(PYA)]PYCFADPY[Nle]CA (SEQ ID NO: 67; BCY8928) |
| BCY12964 | [Ac]A[HArg]DC[HyP]LVNPLCKHP[dD]W[HArg]C (SEQ ID NO: 19; BCY12737) | Ac-C[tBuAla]PE[D-Lys(PYA)]PYCFADPY[Nle]CA (SEQ ID NO: 67; BCY8928) |
| BCY12965 | A[HArg]DC[HyP]LVNPLCLHP[dE]V[HArg]C (SEQ ID NO: 20; BCY12738) | Ac-C[tBuAla]PE[D-Lys(PYA)]PYCFADPY[Nle]CA (SEQ ID NO: 67; BCY8928) |

| Heterotandem Complex No. | First Peptide | Second Peptide |
| --- | --- | --- |
| BCY12966 | A[HArg]EC[HyP]LVNPLCLHP[dE]V[HArg]C (SEQ ID NO: 21; BCY12739) | Ac-C[tBuAla]PE[D-Lys(PYA)]PYCFADPY[Nle]CA (SEQ ID NO: 67; BCY8928) |
| BCY13029 | A[HArg]DC[HyP]LVNPLCLEP[dD]W[HArg]C (SEQ ID NO: 22; BCY12854) | Ac-C[tBuAla]PE[D-Lys(PYA)]PYCFADPY[Nle]CA (SEQ ID NO: 67; BCY8928) |
| BCY13030 | A[HArg]DC[HyP]LVNPLCLHP[dD]WTC (SEQ ID NO: 23; BCY12855) | Ac-C[tBuAla]PE[D-Lys(PYA)]PYCFADPY[Nle]CA (SEQ ID NO: 67; BCY8928) |
| BCY13031 | A[HArg]DC[HyP]LVNPLCLEP[dD]WTC (SEQ ID NO: 24; BCY12856) | Ac-C[tBuAla]PE[D-Lys(PYA)]PYCFADPY[Nle]CA (SEQ ID NO: 67; BCY8928) |
| BCY13032 | A[HArg]DC[HyP]LVNPLCLEP[dD]WTC[dA] (SEQ ID NO: 25; BCY12857) | Ac-C[tBuAla]PE[D-Lys(PYA)]PYCFADPY[Nle]CA (SEQ ID NO: 67; BCY8928) |
| BCY13033 | A[HArg]DC[HyP]LVNPLCLEP[dA]WTC (SEQ ID NO: 26; BCY12858) | Ac-C[tBuAla]PE[D-Lys(PYA)]PYCFADPY[Nle]CA (SEQ ID NO: 67; BCY8928) |
| BCY13034 | A[HArg]DC[HyP]LVNPLCL[33DPA]P[dD]WTC (SEQ ID NO: 27; BCY12859) | Ac-C[tBuAla]PE[D-Lys(PYA)]PYCFADPY[Nle]CA (SEQ ID NO: 67; BCY8928) |
| BCY13035 | C[HyP]LVNPLCL[33DPA]P[dD]WTC SEQ ID NO: 28; BCY12860) | Ac-C[tBuAla]PE[D-Lys(PYA)]PYCFADPY[Nle]CA (SEQ ID NO: 67; BCY8928) |
| BCY13036 | C[HyP]LVNPLCLEP[dD]WTC[dA] (SEQ ID NO: 29; BCY12861) | Ac-C[tBuAla]PE[D-Lys(PYA)]PYCFADPY[Nle]CA (SEQ ID NO: 67; BCY8928) |
| BCY13037 | A[HArg]DC[HyP][Cba]VNPLCLHP[dD]W[HArg]C (SEQ ID NO: 30; BCY12862) | Ac-C[tBuAla]PE[D-Lys(PYA)]PYCFADPY[Nle]CA (SEQ ID NO: 67; BCY8928) |
| BCY13038 | A[HArg]DC[HyP][Cba]VNPLCLEP[dD]WTC (SEQ ID NO: 31; BCY12863) | Ac-C[tBuAla]PE[D-Lys(PYA)]PYCFADPY[Nle]CA (SEQ ID NO: 67; BCY8928) |
| BCY13039 | [dA][HArg]DC[HyP][Cba]VNPLCLEP[dD]WTC[dA] (SEQ ID NO: 32; BCY12864) | Ac-C[tBuAla]PE[D-Lys(PYA)]PYCFADPY[Nle]CA (SEQ ID NO: 67; BCY8928) |
| BCY13040 | C[HyP][Cba]VNPLCL[33DPA]P[dD]WTC[dA] (SEQ ID NO: 33; BCY12865) | Ac-C[tBuAla]PE[D-Lys(PYA)]PYCFADPY[Nle]CA (SEQ ID NO: 67; BCY8928) |
| BCY13041 | A[HArg]DC[HyP]LVNPLCL[33DPA]P[dD]W[HArg]C (SEQ ID NO: 34; BCY12866) | Ac-C[tBuAla]PE[D-Lys(PYA)]PYCFADPY[Nle]CA (SEQ ID NO: 67; BCY8928) |
| BCY13141 | A[HArg]DC[HyP]LVNPLCLEP[dD]WTC (SEQ ID NO: 24; BCY12856) | [3-mercaptopropionic acid][tBuAla]PE[dK(PYA)]PYCFADPY[Nle]C (SEQ ID NO: 77; BCY12353) |
| BCY13142 | A[HArg]DC[HyP]LVNPLCLHP[dD]W[HArg]C (SEQ ID NO: 15; BCY9594) | [3-mercaptopropionic acid][tBuAla]EE[dK]PYCFADPY[Nle]C (SEQ ID NO: 80; BCY13137) |
| BCY13143 | A[HArg]DC[HyP]LVNPLCLEP[dD]WTC (SEQ ID NO: 24; BCY12856) | [3-mercaptopropionic acid][tBuAla]EE[dK]PYCFADPY[Nle]C (SEQ ID NO: 80; BCY13137) |
| BCY13250 | A[HArg]DC[HyP]LVNPLCLHP[d1Nal]W[HArg]C (SEQ ID NO: 35; BCY13116) | Ac-C[tBuAla]PE[D-Lys(PYA)]PYCFADPY[Nle]CA (SEQ ID NO: 67; BCY8928) |
| BCY13251 | A[HArg]DC[HyP]LVNPLCL[1Nal]P[dD]W[HArg]C (SEQ ID NO: 36; BCY13117) | Ac-C[tBuAla]PE[D-Lys(PYA)]PYCFADPY[Nle]CA (SEQ ID NO: 67; BCY8928) |
| BCY13252 | A[HArg]DC[HyP]LVNPLCLEP[d1Nal]WTC (SEQ ID NO: 37; BCY13118) | Ac-C[tBuAla]PE[D-Lys(PYA)]PYCFADPY[Nle]CA (SEQ ID NO: 67; BCY8928) |
| BCY13253 | C[HyP]LVNPLCLONalp[dD]WTC (SEQ ID NO: 38; BCY13119) | Ac-C[tBuAla]PE[D-Lys(PYA)]PYCFADPY[Nle]CA (SEQ ID NO: 67; BCY8928) |
| BCY13254 | [Ac]C[HyP]LVNPLCL[33DPA]P[dD]WTC[dK] (SEQ ID NO: 39; BCY13120) | Ac-C[tBuAla]PE[D-Lys(PYA)]PYCFADPY[Nle]CA (SEQ ID NO: 67; BCY8928) |
| BCY13255 | [NMeAla][HArg]DC[HyP]LVNPLCLHP[dD]W[HArg]C (SEQ ID NO: 40; BCY13121) | Ac-C[tBuAla]PE[D-Lys(PYA)]PYCFADPY[Nle]CA (SEQ ID NO: 67; BCY8928) |
| BCY13256 | [NMeAla][HArg]DC[HyP]LVNPLCLEP[dD]WTC (SEQ ID NO: 41; BCY13122) | Ac-C[tBuAla]PE[D-Lys(PYA)]PYCFADPY[Nle]CA (SEQ ID NO: 67; BCY8928) |

| Heterotandem Complex No. | First Peptide | Second Peptide |
|---|---|---|
| BCY13257 | [dA][HArg]DC[HyP][Cba]VNPLCLEP[dA]WTC[dA] (SEQ ID NO: 42; BCY13123) | Ac-C[tBuAla]PE[D-Lys(PYA)]PYCFADPY[Nle]CA (SEQ ID NO: 67; BCY8928) |
| BCY13258 | [d1Nal][HArg]DC[HyP][Cba]VNPLCLEP[dA]WTC[dA] (SEQ ID NO: 43; BCY13124) | Ac-C[tBuAla]PE[D-Lys(PYA)]PYCFADPY[Nle]CA (SEQ ID NO: 67; BCY8928) |
| BCY13260 | [dA]EDC[HyP]LVNPLCLEP[dD]WTC SEQ ID NO: 44; BCY13126) | Ac-C[tBuAla]PE[D-Lys(PYA)]PYCFADPY[Nle]CA (SEQ ID NO: 67; BCY8928) |
| BCY13261 | [dA][dA]DC[HyP]LVNPLCLEP[dD]WTC SEQ ID NO: 45; BCY13127) | Ac-C[tBuAla]PE[D-Lys(PYA)]PYCFADPY[Nle]CA (SEQ ID NO: 67; BCY8928) |
| BCY13262 | ADC[HyP]LVNPLCLEP[dD]WTC (SEQ ID NO: 46; BCY13128) | Ac-C[tBuAla]PE[D-Lys(PYA)]PYCFADPY[Nle]CA (SEQ ID NO: 67; BCY8928) |
| BCY13264 | A[HArg]DC[HyP][hGlu]VNPLCLHP[dD]W[HArg]C (SEQ ID NO: 47; BCY13130) | Ac-C[tBuAla]PE[D-Lys(PYA)]PYCFADPY[Nle]CA (SEQ ID NO: 67; BCY8928) |
| BCY13265 | A[HArg]DC[HyP]LVNPLC[hGlu]HP[dD]W[HArg]C (SEQ ID NO: 48; BCY13131) | Ac-C[tBuAla]PE[D-Lys(PYA)]PYCFADPY[Nle]CA (SEQ ID NO: 67; BCY8928) |
| BCY13266 | A[HArg]DC[HyP]LVNPLCL[hGlu]P[dD]W[HArg]C (SEQ ID NO: 49; BCY13132) | Ac-C[tBuAla]PE[D-Lys(PYA)]PYCFADPY[Nle]CA (SEQ ID NO: 67; BCY8928) |
| BCY13268 | A[HArg]DC[HyP]LVNPLCLHP[dNle]W[HArg]C (SEQ ID NO: 50; BCY13134) | Ac-C[tBuAla]PE[D-Lys(PYA)]PYCFADPY[Nle]CA (SEQ ID NO: 67; BCY8928) |
| BCY13269 | A[HArg]DC[HyP]LVNPLCL[Nle]P[dD]W[HArg]C (SEQ ID NO: 51; BCY13135) | Ac-C[tBuAla]PE[D-Lys(PYA)]PYCFADPY[Nle]CA (SEQ ID NO: 67; BCY8928) |
| BCY13340 | C[HyP][Cba]VNPLCL[33DPA]P[dD]WTC[dA] (SEQ ID NO: 33; BCY12865) | [3-mercaptopropionic acid][tBuAla]PE[dK(PYA)]PYCFADPY[Nle]C (SEQ ID NO: 77; BCY12353) |
| BCY13342 | C[HyP]LVNPLCL[33DPA]P[dD]WTC (SEQ ID NO: 28; BCY12860) | [3-mercaptopropionic acid][tBuAla]PE[dK(PYA)]PYCFADPY[Nle]C (SEQ ID NO: 77; BCY12353) |
| BCY11616 | CP[1Nal][dD]CM[HArg]DWSTP[HyP]WC SEQ ID NO: 52; BCY8116) | Ac-ACIEE(D-K)(PYA)QYCFADPY(Nle)CA (SEQ ID NO: 81; BCY7744) |
| BCY12238 | [Ac]CP[1Nal][dK]CM[HArg]DWSTP[HyP]WC (SEQ ID NO: 53; BCY12024) | Ac-C[tBuAla]PE[D-Lys(PYA)]PYCFADPY[Nle]CA (SEQ ID NO: 67; BCY8928) |
| BCY12377 | CP[1Nal][dD]CM[HArg]DWSTP[HyP]WC SEQ ID NO: 52; BCY8116) | [Ac]C[tBuAla]EE[dK(PYA)]PYCFADPY[Nle]C (SEQ ID NO: 71; BCY12143) |
| BCY12379 | CP[1Nal][dD]CM[HArg]DWSTP[HyP]WC SEQ ID NO: 52; BCY8116) | [Ac]C[tBuAla]PE[dK(PYA)]PYCFADPY[Nle]C (SEQ ID NO: 72; BCY12149) |
| BCY12572 | CP[1Nal][dD]CM[HArg]DWSTP[HyP]WC SEQ ID NO: 52; BCY8116) | [Ac]C[tBuAla]PE[dK(PYA)]PYCFADPY[Nle][Cysteamine] (SEQ ID NO: 76; BCY12352) |
| BCY12573 | CP[1Nal][dD]CM[HArg]DWSTP[HyP]WC SEQ ID NO: 52; BCY8116) | [3-mercaptopropionic acid][tBuAla]PE[dK(PYA)]PYCFADPY[Nle]C (SEQ ID NO: 77; BCY12353) |
| BCY12574 | CP[1Nal][dD]CM[HArg]DWSTP[HyP]WC SEQ ID NO: 52; BCY8116) | [3-mercaptopropionic acid][tBuAla]PE[dK(PYA)]PYCFADPY[Nle][Cysteamine] (SEQ ID NO: 78; BCY12354) |
| BCY12575 | CP[1Nal][dD]CM[HArg]DWSTP[HyP]WC SEQ ID NO: 52; BCY8116) | Palmitic acid-yGly-yGlu-C[tBuAla]PE[dK(PYA)]PYCFADPY[Nle]C (SEQ ID NO: 79; BCY12360) |
| BCY12576 | [3-mercaptopropionic acid]P[1Nal][dK]CM[HArg]DWSTP[HyP]WC (SEQ ID NO: 54; BCY12363) | Ac-C[tBuAla]PE[D-Lys(PYA)]PYCFADPY[Nle]CA (SEQ ID NO: 67; BCY8928) |
| BCY12577 | [Ac]CP[1Nal][dK]CM[HArg]DWSTP[HyP]W[Cysteamine] (SEQ ID NO: 55; BCY12364) | Ac-C[tBuAla]PE[D-Lys(PYA)]PYCFADPY[Nle]CA (SEQ ID NO: 67; BCY8928) |
| BCY12578 | [3-mercaptopropionic acid]P[1Nal][dK]CM [HArg]DWSTP[HyP]W[Cysteamine] (SEQ ID NO: 56; BCY12365) | Ac-C[tBuAla]PE[D-Lys(PYA)]PYCFADPY[Nle]CA (SEQ ID NO: 67; BCY8928) |

| Heterotandem Complex No. | First Peptide | Second Peptide |
|---|---|---|
| BCY12579 | [Ac]CP[1Nal][dK]CM[HArg]HWSTP[HyP]WC (SEQ ID NO: 57; BCY12366) | Ac-C[tBuAla]PE[D-Lys(PYA)]PYCFADPY[Nle]CA (SEQ ID NO: 67; BCY8928) |
| BCY12580 | [Ac]CP[1Nal][dK]CM[HArg]EWSTP[HyP]WC (SEQ ID NO: 58; BCY12367) | Ac-C[tBuAla]PE[D-Lys(PYA)]PYCFADPY[Nle]CA (SEQ ID NO: 67; BCY8928) |
| BCY12581 | CP[1Nal][dE]CM[HArg]DWSTP[HyP]WC SEQ ID NO: 59; BCY12368) | Ac-C[tBuAla]PE[D-Lys(PYA)]PYCFADPY[Nle]CA (SEQ ID NO: 67; BCY8928) |
| BCY12582 | CP[1Nal][dA]CM[HArg]DWSTP[HyP]WC SEQ ID NO: 60; BCY12369) | Ac-C[tBuAla]PE[D-Lys(PYA)]PYCFADPY[Nle]CA (SEQ ID NO: 67; BCY8928) |
| BCY12583 | CP[1Nal][dE]CL[HArg]DWSTP[HyP]WC SEQ ID NO: 61; BCY12370) | Ac-C[tBuAla]PE[D-Lys(PYA)]PYCFADPY[Nle]CA (SEQ ID NO: 67; BCY8928) |
| BCY12584 | Palmitic-yGlu-yGlu-CP[1Nal][dK]CM[HArg]DWSTP[HyP]WC SEQ ID NO: 62; BCY12371) | Ac-C[tBuAla]PE[D-Lys(PYA)]PYCFADPY[Nle]CA (SEQ ID NO: 67; BCY8928) |
| BCY12585 | CP[1Nal][dE]CM[HArg]EWSTP[HyP]WC SEQ ID NO: 63; BCY12384) | Ac-C[tBuAla]PE[D-Lys(PYA)]PYCFADPY[Nle]CA (SEQ ID NO: 67; BCY8928) |
| BCY12709 | CP[1Nal][dD]CM[HArg]DWSTP[HyP]WC SEQ ID NO: 52; BCY8116) | [Ac]C[tBuAla]PE[dK(PYA)]PYCFAD[NMeAla]Y[Nle]C (SEQ ID NO: 82; BCY12381) |
| BCY12710 | CP[1Nal][dD]CM[HArg]DWSTP[HyP]WC SEQ ID NO: 52; BCY8116) | [Ac]C[tBuAla]PE[dK(PYA)]PYCFAD[NMeDAla]Y[Nle]C (SEQ ID NO: 83; BCY12382) |
| BCY11468 | [PYA][B-Ala]CP[1Nal][dD]CM[HArg]DWSTP[HyP]WC (SEQ ID NO: 64; BCY11016) | Ac-C[tBuAla]PE[D-Lys(PYA)]PYCFADPY[Nle]CA (SEQ ID NO: 67; BCY8928) |
| BCY11618 | [PYA][B-Ala]CP[1Nal][dK]CM[HArg]DWSTP[HyP]WC (SEQ ID NO: 65; BCY11143) | Ac-C[tBuAla]PE[D-Lys]PYCFADPY[Nle]CA (SEQ ID NO: 70; BCY8920) |
| BCY11776 | CP[1Nal][dD]CM[HArg]DWSTP[HyP]WC SEQ ID NO: 52; BCY8116) | [Ac]C[tBuAla]PE[dK]PYCFADPY[Nle]C[Dap(PYA)] (SEQ ID NO: 69; BCY11144) |
| BCY11860 | [PYA][B-Ala]CP[1Nal][dK]CM[HArg]DWSTP[HyP]WC (SEQ ID NO: 65; BCY11143) | Ac-C[tBuAla]PE[D-Lys]PYCFADPY[Nle]CA (SEQ ID NO: 70; BCY8920) |
| BCY12020 | [PYA][B-Ala]CP[1Nal][dD]CM[HArg]DWSTP[HyP]WC (SEQ ID NO: 64; BCY11016) | [Ac]C[tBuAla]PE[dK]PYCFADPY[Nle]C[Dap(PYA)] (SEQ ID NO: 69; BCY11144) |
| BCY12661 | [PYA]CP[1Nal][dD]CM[HArg]DWSTP[HyP]WC (SEQ ID NO: 66; BCY11015) | [Ac]C[tBuAla]EE(dK)PYCFADPY[Nle]C[Dap(PYA)] (SEQ ID NO: 68; BCY12023) |
| BCY12969 | CP[1Nal][dD]CM[HArg]DWSTP[HyP]WC SEQ ID NO: 52; BCY8116) | [Ac]C[tBuAla]PE[dK(PYA)]PYCFADPY[Nle]C[1,2-diaminoethane] (SEQ ID NO: 84; BCY12358) | wherein 1Nal represents 1-naphthylalanine, HArg represents homoarginine, HyP represents hydroxyproline, B-Ala represents beta-alanine, PYA represents 4-pentynoic acid, 3,3-DPA represents 3,3-diphenylalanine, Cba represents β-cyclobutylalanine, hGlu represents homoglutamic acid, Nle represents norleucine, NMeAla represents N-methyl-alanine, tBuAla represents t-butyl-alanine, Aad represents alpha-L-aminoadipic acid, Ac represents an acetyl group, Dap represents diaminopropionic acid, or a pharmaceutically acceptable salt thereof.

According to a further aspect of the invention, there is provided a pharmaceutical composition comprising a heterotandem bicyclic peptide complex as defined herein in combination with one or more pharmaceutically acceptable excipients.

According to a further aspect of the invention, there is provided a heterotandem bicyclic peptide complex as defined herein for use in preventing, suppressing or treating cancer.

DETAILED DESCRIPTION OF THE INVENTION

First Peptide Ligands

References herein to the term "cancer cell" includes any cell which is known to be involved in cancer. Cancer cells are created when the genes responsible for regulating cell division are damaged. Carcinogenesis is caused by mutation and epimutation of the genetic material of normal cells, which upsets the normal balance between proliferation and cell death. This results in uncontrolled cell division and the evolution of those cells by natural selection in the body. The uncontrolled and often rapid proliferation of cells can lead to benign or malignant tumours (cancer). Benign tumors do not spread to other parts of the body or invade other tissues. Malignant tumors can invade other organs, spread to distant iodations (metastasis) and become life-threatening.

In one embodiment, the cancer cell is selected from an HT1080, A549, SC-OV-3, PC3, H1376, NCI-H292, LnCap, MC38, 4T1-D02 and RKO tumor cell.

In one embodiment, the component present on a cancer cell is Nectin-4.

Nectin-4 is a surface molecule that belongs to the nectin family of proteins, which comprises 4 members. Nectins are cell adhesion molecules that play a key role in various biological processes such as polarity, proliferation, differentiation and migration, for epithelial, endothelial, immune and neuronal cells, during development and adult life. They are involved in several pathological processes in humans. They are the main receptors for poliovirus, herpes simplex virus and measles virus. Mutations in the genes encoding Nectin-1 (PVRL1) or Nectin-4 (PVRL4) cause ectodermal dysplasia syndromes associated with other abnormalities. Nectin-4 is expressed during foetal development. In adult tissues its expression is more restricted than that of other members of the family. Nectin-4 is a tumour-associated antigen in 50%, 49% and 86% of breast, ovarian and lung carcinomas, respectively, mostly on tumours of bad prognosis. Its expression is not detected in the corresponding normal tissues. In breast tumours, Nectin-4 is expressed mainly in triple-negative and ERBB2+ carcinomas. In the serum of patients with these cancers, the detection of soluble forms of Nectin-4 is associated with a poor prognosis. Levels of serum Nectin-4 increase during metastatic progression and decrease after treatment. These results suggest that Nectin-4 could be a reliable target for the treatment of cancer. Accordingly, several anti-Nectin-4 antibodies have been described in the prior art. In particular, Enfortumab Vedotin (ASG-22ME) is an antibody-drug conjugate (ADC) targeting Nectin-4 and is currently clinically investigated for the treatment of patients suffering from solid tumours.

In one embodiment, the first peptide ligand comprises a Nectin-4 binding bicyclic peptide ligand.

Suitable examples of Nectin-4 binding bicyclic peptide ligands are disclosed in PCT Patent Application No PCT/GB2019/051740, the peptides of which are incorporated herein by reference.

In one embodiment, the Nectin-4 binding bicyclic peptide is selected from any of the peptides of SEQ ID NOS: 52 to 66 described herein.

In an alternative embodiment, the component present on a cancer cell is EphA2.

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov et al. (2004) Dev Cell 7, 465-80). Functional and biochemical Eph responses occur at higher ligand oligomerization states (Stein et al. (1998) Genes Dev 12, 667-678).

Among other patterning functions, various Ephs and ephrins have been shown to play a role in vascular development. Knockout of EphB4 and ephrin-B2 results in a lack of the ability to remodel capillary beds into blood vessels (Poliakov et al., supra) and embryonic lethality. Persistent expression of some Eph receptors and ephrins has also been observed in newly-formed, adult micro-vessels (Brantley-Sieders et al. (2004) Curr Pharm Des 10, 3431-42; Adams (2003) J Anat 202, 105-12).

The de-regulated re-emergence of some ephrins and their receptors in adults also has been observed to contribute to tumor invasion, metastasis and neo-angiogenesis (Nakamoto et al. (2002) Microsc Res Tech 59, 58-67; Brantley-Sieders et al., supra). Furthermore, some Eph family members have been found to be over-expressed on tumor cells from a variety of human tumors (Brantley-Sieders et al., supra); Marme (2002) Ann Hematol 81 Suppl 2, S66; Booth et al. (2002) Nat Med 8, 1360-1).

EPH receptor A2 (ephrin type-A receptor 2) is a protein that in humans is encoded by the EPHA2 gene.

EphA2 is upregulated in multiple cancers in man, often correlating with disease progression, metastasis and poor prognosis e.g.: breast (Zelinski et al (2001) Cancer Res. 61, 2301-2306; Zhuang et al (2010) Cancer Res. 70, 299-308; Brantley-Sieders et al (2011) PLoS One 6, e24426), lung (Brannan et al (2009) Cancer Prev Res (Phila) 2, 1039-1049; Kinch et al (2003) Clin Cancer Res. 9, 613-618; Guo et al (2013) J Thorac Oncol. 8, 301-308), gastric (Nakamura et al (2005) Cancer Sci. 96, 42-47; Yuan et al (2009) Dig Dis Sci 54, 2410-2417), pancreatic (Mudali et al (2006) Clin Exp Metastasis 23, 357-365), prostate (Walker-Daniels et al (1999) Prostate 41, 275-280), liver (Yang et al (2009) Hepatol Res. 39, 1169-1177) and glioblastoma (Wykosky et al (2005) Mol Cancer Res. 3, 541-551; Li et al (2010) Tumour Biol. 31, 477-488).

The full role of EphA2 in cancer progression is still not defined although there is evidence for interaction at numerous stages of cancer progression including tumour cell growth, survival, invasion and angiogenesis. Downregulation of EphA2 expression suppresses tumour cancer cell propagation (Binda et al (2012) Cancer Cell 22, 765-780), whilst EphA2 blockade inhibits VEGF induced cell migration (Hess et al (2001) Cancer Res. 61, 3250-3255), sprouting and angiogenesis (Cheng et al (2002) Mol Cancer Res. 1, 2-11; Lin et al (2007) Cancer 109, 332-40) and metastatic progression (Brantley-Sieders et al (2005) FASEB J. 19, 1884-1886).

An antibody drug conjugate to EphA2 has been shown to significantly diminish tumour growth in rat and mouse xenograft models (Jackson et al (2008) Cancer Research 68, 9367-9374) and a similar approach has been tried in man although treatment had to be discontinued for treatment related adverse events (Annunziata et al (2013) Invest New drugs 31, 77-84).

In one embodiment, the first peptide ligand comprises an EphA2 binding bicyclic peptide ligand.

Suitable examples of EphA2 binding bicyclic peptide ligands are disclosed in WO 2019/122860, WO 2019/122861 and WO 2019/122863, the peptides of which are incorporated herein by reference.

In one embodiment, the EphA2 binding bicyclic peptide is selected from any of the peptides of SEQ ID NOS: 10 to 51 described herein.

In an alternative embodiment, the component present on a cancer cell is PD-L1.

Programmed cell death 1 ligand 1 (PD-L1) is a 290 amino acid type I transmembrane protein encoded by the CD274 gene on mouse chromosome 19 and human chromosome 9. PD-L1 expression is involved in evasion of immune responses involved in chronic infection, e.g., chronic viral infection (including, for example, HIV, HBV, HCV and HTLV, among others), chronic bacterial infection (including, for example, *Helicobacter pylori*, among others), and chronic parasitic infection (including, for example, *Schistosoma mansoni*). PD-L1 expression has been detected in a number of tissues and cell types including T-cells, B-cells, macrophages, dendritic cells, and nonhaematopoietic cells including endothelial cells, hepatocytes, muscle cells, and placenta.

PD-L1 expression is also involved in suppression of anti-tumour immune activity. Tumours express antigens that can be recognised by host T-cells, but immunologic clearance of tumours is rare. Part of this failure is due to immune suppression by the tumour microenvironment. PD-L1 expression on many tumours is a component of this suppressive milieu and acts in concert with other immunosuppressive signals. PD-L1 expression has been shown in situ on a wide variety of solid tumours including breast, lung, colon, ovarian, melanoma, bladder, liver, salivary, stomach, gliomas, thyroid, thymic epithelial, head, and neck (Brown J A et al. 2003 Immunol. 170:1257-66; Dong H et al. 2002 Nat. Med. 8:793-800; Hamanishi J, et al. 2007 Proc. Natl. Acad. Sci. USA 104:3360-65; Strome S E et al. 2003 Cancer Res. 63:6501-5; Inman B A et al. 2007 Cancer 109:1499-505; Konishi J et al. 2004 Clin. Cancer Res. 10:5094-100; Nakanishi J et al. 2007 Cancer Immunol. Immunother. 56:1173-82; Nomi T et al. 2007 Clin. Cancer Res. 13:2151-57; Thompson R H et al. 2004 Proc. Natl. Acad. Sci. USA 101: 17174-79; Wu C et al. 2006 Acta Histochem. 108:19-24). In addition, the expression of the receptor for PD-L1, Programmed cell death protein 1 (also known as PD-1 and CD279) is upregulated on tumour infiltrating lymphocytes, and this also contributes to tumour immunosuppression (Blank C et al. 2003 Immunol. 171:4574-81). Most importantly, studies relating PD-L1 expression on tumours to disease outcome show that PD-L1 expression strongly correlates with unfavourable prognosis in kidney, ovarian, bladder, breast, gastric, and pancreatic cancer (Hamanishi J et al. 2007 Proc. Natl. Acad. Sci. USA 104:3360-65; Inman B A et al. 2007 Cancer 109:1499-505; Konishi J et al. 2004 Clin. Cancer Res. 10:5094-100; Nakanishi J et al. 2007 Cancer Immunol. Immunother. 56:1173-82; Nomi T et al. 2007 Clin. Cancer Res. 13:2151-57; Thompson R H et al. 2004 Proc. Natl. Acad. Sci. USA 101:17174-79; Wu C et al. 2006 Acta Histochem. 108:19-24). In addition, these studies suggest that higher levels of PD-L1 expression on tumours may facilitate advancement of tumour stage and invasion into deeper tissue structures.

The PD-1 pathway can also play a role in haematologic malignancies. PD-L1 is expressed on multiple myeloma cells but not on normal plasma cells (Liu J et al. 2007 Blood 110:296-304). PD-L1 is expressed on some primary T-cell lymphomas, particularly anaplastic large cell T lymphomas (Brown J A et al, 2003 Immunol. 170:1257-66). PD-1 is highly expressed on the T-cells of angioimmunoblastic lymphomas, and PD-L1 is expressed on the associated follicular dendritic cell network (Dorfman D M et al. 2006 Am. J. Surg. Pathol. 30:802-10). In nodular lymphocyte-predominant Hodgkin lymphoma, the T-cells associated with lymphocytic or histiocytic (L&H) cells express PD-1. Microarray analysis using a readout of genes induced by PD-1 ligation suggests that tumour-associated T-cells are responding to PD-1 signals in situ in Hodgkin lymphoma (Chemnitz J M et al. 2007 Blood 110:3226-33). PD-1 and PD-L1 are expressed on CD4 T-cells in HTLV-1-mediated adult T-cell leukaemia and lymphoma (Shimauchi T et al. 2007 Int. J. Cancer 121: 2585-90). These tumour cells are hyporesponsive to TCR signals.

Studies in animal models demonstrate that PD-L1 on tumours inhibits T-cell activation and lysis of tumour cells and in some cases leads to increased tumour-specific T-cell death (Dong H et al. 2002 Nat. Med. 8:793-800; Hirano F et al. 2005 Cancer Res. 65:1089-96). Tumour-associated APCs can also utilise the PD-1:PD-L1 pathway to control antitumour T-cell responses. PD-L1 expression on a population of tumour-associated myeloid DCs is upregulated by tumour environmental factors (Curiel T J et al. 2003 Nat. Med. 9:562-67). Plasmacytoid dendritic cells (DCs) in the tumour-draining lymph node of B16 melanoma express IDO, which strongly activates the suppressive activity of regulatory T-cells. The suppressive activity of IDO-treated regulatory T-cells required cell contact with IDO-expressing DCs (Sharma M D et al. 2007 Clin. Invest. 117:2570-82).

In one embodiment, the first peptide ligand comprises a PD-L1 binding bicyclic peptide ligand.

Suitable examples of PD-L1 binding bicyclic peptide ligands are disclosed in GB Patent Application Nos. 1905631.6 and 1904622.6, the peptides of which are incorporated herein by reference.

In one embodiment, the PD-L1 binding bicyclic peptide is selected from any of the peptides of SEQ ID NOS: 1 to 9 described herein.

In an alternative embodiment, the component present on a cancer cell is prostate-specific membrane antigen (PSMA).

Prostate-specific membrane antigen (PSMA) (also known as Glutamate carboxypeptidase II (GCPII), N-acetyl-L-aspartyl-L-glutamate peptidase I (NAALADase I) and NAAG peptidase) is an enzyme that in humans is encoded by the FOLH1 (folate hydrolase 1) gene. Human GCPII contains 750 amino acids and weighs approximately 84 kDa.

Human PSMA is highly expressed in the prostate, roughly a hundred times greater than in most other tissues. In some prostate cancers, PSMA is the second-most upregulated gene product, with an 8- to 12-fold increase over levels in noncancerous prostate cells. Because of this high expression, PSMA is being developed as potential biomarker for therapy and imaging of some cancers. In human prostate cancer, the higher expressing tumors are associated with quicker time to progression and a greater percentage of patients suffering relapse.

In one embodiment, the first peptide ligand comprises a PSMA binding bicyclic peptide ligand.

Suitable examples of PSMA binding bicyclic peptide ligands are disclosed in GB Patent Application Nos 1820325.7 and 1912723.2 and PCT Patent Application No. PCT/EP2019/066273, the peptides of which are incorporated herein by reference.

Second Peptide Ligands

References herein to the term "immune cell" includes any cell within the immune system. Suitable examples include white blood cells, such as lymphocytes (e.g. T lymphocytes or T cells, B cells or natural killer cells). In one embodiment, the T cell is CD8 or CD4. In a further embodiment, the T cell is CD8. Other examples of immune cells include dendritic cells, follicular dendritic cells and granulocytes.

In one embodiment, the component present on an immune cell is CD137.

CD137 is a member of the tumour necrosis factor (TNF) receptor family. Its alternative names are tumour necrosis factor receptor superfamily member 9 (TNFRSF9), 4-IBB and induced by lymphocyte activation (ILA). CD137 can be expressed by activated T cells, but to a larger extent on CD8+ than on CD4+ T cells. In addition, CD137 expression is found on dendritic cells, follicular dendritic cells, natural killer cells, granulocytes and cells of blood vessel walls at sites of inflammation. One characterized activity of CD137 is its costimulatory activity for activated T cells. Crosslinking of CD137 enhances T cell proliferation, IL-2 secretion, survival and cytolytic activity. Further, it can enhance immune activity to eliminate tumours in mice.

CD137 is a T-cell costimulatory receptor induced on TCR activation (Nam et al., Curr. Cancer Drug Targets, 5:357-363 (2005); Waits et al., Annu. Rev, Immunol., 23:23-68 (2005)). In addition to its expression on activated CD4+ and CD8+ T cells, CD137 is also expressed on CD4+CD25+ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al. Annu. Rev. Immunol, 23:23-68 (2005)). On interaction with its ligand, CD137 leads to increased TCR-induced T-cell proliferation, cytokine production, functional maturation, and prolonged CD8+ T-cell survival (Nam et al, Curr. Cancer Drug Targets, 5:357-363 (2005), Watts et d-I., Annu. Rev. Immunol, 23:23-68 (2005)).

Signalling through CD137 by either CD137L or agonistic monoclonal antibodies (mAbs) against CD137 leads to increased TCR-induced T cell proliferation, cytokine production and functional maturation, and prolonged CD8+ T cell survival. These effects result from: (1) the activation of the NF-κB, c-Jun NH2-terminal kinase/stress-activated protein kinase (JNK/SAPK), and p38 mitogen-activated protein kinase (MAPK) signalling pathways, and (2) the control of anti-apoptotic and cell cycle-related gene expression.

Experiments performed in both CD137 and CD137L-deficient mice have additionally demonstrated the importance of CD137 costimulation in the generation of a fully competent T cell response.

IL-2 and IL-15 activated NK cells express CD137, and ligation of CD137 by agonistic mAbs stimulates NK cell proliferation and IFN-γ secretion, but not their cytolytic activity.

Furthermore, CD137-stimulated NK cells promote the expansion of activated T cells in vitro.

In accordance with their costimulatory function, agonist mAbs against CD137 have been shown to promote rejection of cardiac and skin allografts, eradicate established tumours, broaden primary antiviral CD8+ T cell responses, and increase T cell cytolytic potential. These studies support the view that CD137 signalling promotes T cell function which may enhance immunity against tumours and infection.

In one embodiment, the second peptide ligand comprises a CD137 binding bicyclic peptide ligand.

Suitable examples of CD137 binding bicyclic peptide ligands are disclosed in WO 2019/025811, the peptides of which are incorporated herein by reference.

In one embodiment, the CD137 binding bicyclic peptide is selected from any of the peptides of SEQ ID NOS: 67 to 84 described herein.

Linkers

It will be appreciated that the first peptide ligand may be conjugated to the second peptide ligand via any suitable linker. Typically the design of said linker will be such that the two Bicyclic peptides are presented in such a manner that they can bind unencumbered to their respective targets either alone or while simultaneously binding to both target receptors. Additionally, the linker should permit binding to both targets simultaneously while maintaining an appropriate distance between the target cells that would lead to the desired functional outcome. The properties of the linker may be modulated to increase length, rigidity or solubility to optimise the desired functional outcome. The linker may also be designed to permit the attachment of more than one Bicycle to the same target. Increasing the valency of either binding peptide may serve to increase the affinity of the heterotandem for the target cells or may help to induce oligomerisation of one or both of the target receptors.

In one embodiment, the linker is selected from the following sequences: -PEG5- and TCA-[PEG$_{10}$]$_3$.

Structural representations of these linkers are detailed below:

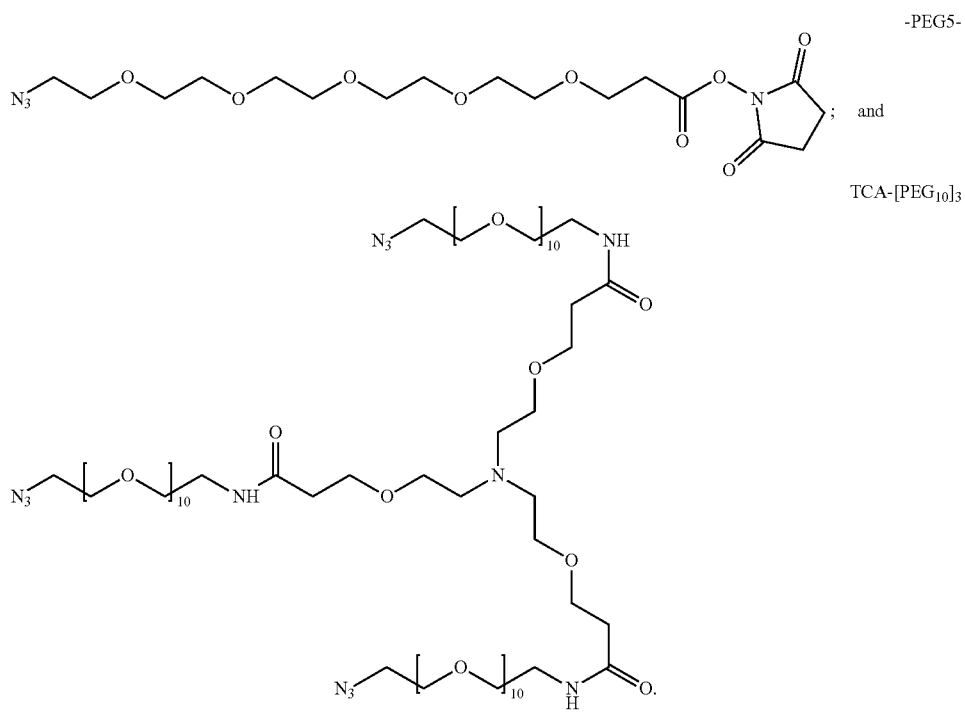

Heterotandem Complexes

In one specific embodiment, the first peptide ligand comprises a PD-L1 binding bicyclic peptide ligand attached to a TATA scaffold, the second peptide ligand comprises a CD137 binding bicyclic peptide ligand attached to a TATA scaffold and said heterotandem complex is selected from the complexes listed in Table A:

TABLE A (PD-L1:CD137; 1:1)

| Complex No. | PD-L1 BCY No. | Attachment Point | Linker | CD137 BCY No. | Attachment Point |
|---|---|---|---|---|---|
| BCY12229 | BCY11865 | Lys9 | Peg5 | BCY8928 | dLys(PYA)4 |
| BCY12230 | BCY11866 | Lys2 | Peg5 | BCY8928 | dLys(PYA)4 |
| BCY12231 | BCY11867 | Lys7 | Peg5 | BCY8928 | dLys(PYA)4 |
| BCY12232 | BCY11868 | Lys8 | Peg5 | BCY8928 | dLys(PYA)4 |
| BCY12242 | BCY11869 | Lys11 | Peg5 | BCY8928 | dLys(PYA)4 |
| BCY12375 | BCY10861 | Lys(PYA)9 | Peg5 | BCY12023 | dLys4 |
| BCY12663 | BCY12479 | C-term Lys | Peg5 | BCY8928 | dLys(PYA)4 |
| BCY12796 | BCY12477 | C-term Lys | Peg5 | BCY8928 | dLys(PYA)4 |
| BCY12021 | BCY10861 | Lys(PYA)9 | Peg5 | BCY11144 | dLys4 |

In one embodiment, the heterotandem bicyclic peptide complex is selected from: BCY12375 and BCY12021.

In one specific embodiment, the first peptide ligand comprises an EphA2 binding bicyclic peptide ligand attached to a TATA scaffold, the second peptide ligand comprises a CD137 binding bicyclic peptide ligand attached to a TATA scaffold and said heterotandem complex is selected from the complexes listed in Table B:

TABLE B (EphA2:CD137; 1:1)

| Complex No. | EphA2 BCY No. | Attachment Point | Linker | CD137 BCY No. | Attachment Point |
|---|---|---|---|---|---|
| BCY12233 | BCY11813 | N-term PYA | Peg5 | BCY8920 | dLys4 |
| BCY12234 | BCY11814 | C-term Lys(PYA) | Peg5 | BCY8920 | dLys4 |
| BCY12235 | BCY11815 | Lys(PYA) 8 | Peg5 | BCY8920 | dLys4 |
| BCY12236 | BCY11816 | Lys(PYA)2 | Peg5 | BCY8920 | dLys4 |
| BCY12237 | BCY11817 | Lys(PYA)7 | Peg5 | BCY8920 | dLys4 |
| BCY12711 | BCY9594 | N-terminus | Peg5 | BCY12143 | dLys (PYA)4 |
| BCY12712 | BCY9594 | N-terminus | Peg5 | BCY12149 | dLys (PYA)4 |
| BCY12713 | BCY9594 | N-terminus | Peg5 | BCY12147 | dLys (PYA)4 |
| BCY12714 | BCY9594 | N-terminus | Peg5 | BCY12145 | dLys (PYA)4 |
| BCY12715 | BCY9594 | N-terminus | Peg5 | BCY12146 | dLys (PYA)4 |
| BCY12717 | BCY9594 | N-terminus | Peg5 | BCY12352 | dLys (PYA)4 |
| BCY12718 | BCY9594 | N-terminus | Peg5 | BCY12353 | dLys (PYA)4 |
| BCY12719 | BCY9594 | N-terminus | Peg5 | BCY12354 | dLys (PYA)4 |
| BCY12720 | BCY9594 | N-terminus | Peg5 | BCY12360 | dLys (PYA)4 |
| BCY12961 | BCY12734 | C-term Lys | Peg5 | BCY8928 | dLys (PYA)4 |
| BCY12962 | BCY12735 | Lys8 | Peg5 | BCY8928 | dLys (PYA)4 |
| BCY12963 | BCY12736 | Lys2 | Peg5 | BCY8928 | dLys (PYA)4 |
| BCY12964 | BCY12737 | Lys7 | Peg5 | BCY8928 | dLys (PYA)4 |
| BCY12965 | BCY12738 | N-terminus | Peg5 | BCY8928 | dLys (PYA)4 |
| BCY12966 | BCY12739 | N-terminus | Peg5 | BCY8928 | dLys (PYA)4 |
| BCY13029 | BCY12854 | N-terminus | Peg5 | BCY8928 | dLys (PYA)4 |
| BCY13030 | BCY12855 | N-terminus | Peg5 | BCY8928 | dLys (PYA)4 |
| BCY13031 | BCY12856 | N-terminus | Peg5 | BCY8928 | dLys (PYA)4 |
| BCY13032 | BCY12857 | N-terminus | Peg5 | BCY8928 | dLys (PYA)4 |
| BCY13033 | BCY12858 | N-terminus | Peg5 | BCY8928 | dLys (PYA)4 |
| BCY13034 | BCY12859 | N-terminus | Peg5 | BCY8928 | dLys (PYA)4 |
| BCY13035 | BCY12860 | N-terminus | Peg5 | BCY8928 | dLys (PYA)4 |
| BCY13036 | BCY12861 | N-terminus | Peg5 | BCY8928 | dLys (PYA)4 |
| BCY13037 | BCY12862 | N-terminus | Peg5 | BCY8928 | dLys (PYA)4 |
| BCY13038 | BCY12863 | N-terminus | Peg5 | BCY8928 | dLys (PYA)4 |
| BCY13039 | BCY12864 | N-terminus | Peg5 | BCY8928 | dLys (PYA)4 |
| BCY13040 | BCY12865 | N-terminus | Peg5 | BCY8928 | dLys (PYA)4 |
| BCY13041 | BCY12866 | N-terminus | Peg5 | BCY8928 | dLys (PYA)4 |
| BCY13141 | BCY12856 | N-terminus | Peg5 | BCY12353 | dLys (PYA)4 |
| BCY13142 | BCY9594 | N-terminus | Peg5 | BCY13137 | dLys (PYA)4 |
| BCY13143 | BCY12856 | N-terminus | Peg5 | BCY13137 | dLys (PYA)4 |
| BCY13250 | BCY13116 | N-terminus | Peg5 | BCY8928 | dLys (PYA)4 |
| BCY13251 | BCY13117 | N-terminus | Peg5 | BCY8928 | dLys (PYA)4 |
| BCY13252 | BCY13118 | N-terminus | Peg5 | BCY8928 | dLys (PYA)4 |
| BCY13253 | BCY13119 | N-terminus | Peg5 | BCY8928 | dLys (PYA)4 |
| BCY13254 | BCY13120 | C-term dLys | Peg5 | BCY8928 | dLys (PYA)4 |
| BCY13255 | BCY13121 | N-terminus | Peg5 | BCY8928 | dLys (PYA)4 |
| BCY13256 | BCY13122 | N-terminus | Peg5 | BCY8928 | dLys (PYA)4 |
| BCY13257 | BCY13123 | N-terminus | Peg5 | BCY8928 | dLys (PYA)4 |
| BCY13258 | BCY13124 | N-terminus | Peg5 | BCY8928 | dLys (PYA)4 |
| BCY13260 | BCY13126 | N-terminus | Peg5 | BCY8928 | dLys (PYA)4 |
| BCY13261 | BCY13127 | N-terminus | Peg5 | BCY8928 | dLys (PYA)4 |
| BCY13262 | BCY13128 | N-terminus | Peg5 | BCY8928 | dLys (PYA)4 |
| BCY13264 | BCY13130 | N-terminus | Peg5 | BCY8928 | dLys (PYA)4 |
| BCY13265 | BCY13131 | N-terminus | Peg5 | BCY8928 | dLys (PYA)4 |

TABLE B-continued

(EphA2:CD137; 1:1)

| Complex No. | EphA2 BCY No. | Attachment Point | Linker | CD137 BCY No. | Attachment Point |
|---|---|---|---|---|---|
| BCY13266 | BCY13132 | N-terminus | Peg5 | BCY8928 | dLys (PYA)4 |
| BCY13268 | BCY13134 | N-terminus | Peg5 | BCY8928 | dLys (PYA)4 |
| BCY13269 | BCY13135 | N-terminus | Peg5 | BCY8928 | dLys (PYA)4 |
| BCY13340 | BCY12865 | N-terminus | Peg5 | BCY12353 | dLys (PYA)4 |
| BCY13342 | BCY12860 | N-terminus | Peg5 | BCY12353 | dLys (PYA)4 |

In one embodiment, the heterotandem bicyclic peptide complex is selected from: BCY13035, BCY13040, BCY13253, BCY13254, BCY13340 and BCY13342.

In one specific embodiment, the first peptide ligand comprises a Nectin-4 binding bicyclic peptide ligand attached to a TATA scaffold, the second peptide ligand comprises a CD137 binding bicyclic peptide ligand attached to a TATA scaffold and said heterotandem complex is selected from the complexes listed in Table C:

TABLE C

(Nectin-4:CD137; 1:1)

| Complex No. | Nectin-4 BCY No. | Attachment Point | Linker | CD137 BCY No. | Attachment Point |
|---|---|---|---|---|---|
| BCY11616 | BCY8116 | N-terminus | Peg5 | BCY7744 | dLys(PYA)4 |
| BCY12238 | BCY12024 | dLys3 | Peg5 | BCY8928 | dLys(PYA)4 |
| BCY12377 | BCY8116 | N-terminus | Peg5 | BCY12143 | dLys(PYA)4 |
| BCY12379 | BCY8116 | N-terminus | Peg5 | BCY12149 | dLys(PYA)4 |
| BCY12572 | BCY8116 | N-terminus | Peg5 | BCY12352 | dLys(PYA)4 |
| BCY12573 | BCY8116 | N-terminus | Peg5 | BCY12353 | dLys(PYA)4 |
| BCY12574 | BCY8116 | N-terminus | Peg5 | BCY12354 | dLys(PYA)4 |
| BCY12575 | BCY8116 | N-terminus | Peg5 | BCY12360 | dLys(PYA)4 |
| BCY12576 | BCY12363 | dLys3 | Peg5 | BCY8928 | dLys(PYA)4 |
| BCY12577 | BCY12364 | dLys3 | Peg5 | BCY8928 | dLys(PYA)4 |
| BCY12578 | BCY12365 | dLys3 | Peg5 | BCY8928 | dLys(PYA)4 |
| BCY12579 | BCY12366 | dLys3 | Peg5 | BCY8928 | dLys(PYA)4 |
| BCY12580 | BCY12367 | dLys3 | Peg5 | BCY8928 | dLys(PYA)4 |
| BCY12581 | BCY12368 | N-terminus | Peg5 | BCY8928 | dLys(PYA)4 |
| BCY12582 | BCY12369 | N-terminus | Peg5 | BCY8928 | dLys(PYA)4 |
| BCY12583 | BCY12370 | N-terminus | Peg5 | BCY8928 | dLys(PYA)4 |
| BCY12584 | BCY12371 | dLys3 | Peg5 | BCY8928 | dLys(PYA)4 |
| BCY12585 | BCY12384 | N-terminus | Peg5 | BCY8928 | dLys(PYA)4 |
| BCY12709 | BCY8116 | N-terminus | Peg5 | BCY12381 | dLys(PYA)4 |
| BCY12710 | BCY8116 | N-terminus | Peg5 | BCY12382 | dLys(PYA)4 |
| BCY11468 | BCY11016 | N-term PYA | TCA-[Peg10]3 | BCY8928 | dLys(PYA)4 |
| BCY11618 | BCY11143 | N-term PYA | Peg5 | BCY8920 | dLys4 |
| BCY11776 | BCY8116 | N-terminus | Peg5 | BCY11144 | C-term Dap(PYA) |
| BCY11860 | BCY11143 | N-term PYA | Peg5 | BCY8920 | dLys4 |
| BCY12020 | BCY11016 | N-term PYA | Peg5 | BCY11144 | C-term Dap(PYA) |
| BCY12661 | BCY11015 | N-term PYA | Peg5 | BCY12023 | dLys4 |
| BCY12969 | BCY8116 | N-terminus | Peg5 | BCY12358 | dLys(PYA)4 |

In one embodiment, the heterotandem bicyclic peptide complex is selected from: BCY11468, BCY11618, BCY11776, BCY11860, BCY12020, BCY12661 and BCY12969.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

Nomenclature

Molecular Format

N- or C-terminal extensions to the bicycle core sequence are added to the left or right side of the sequence, separated by a hyphen. For example, an N-terminal βAla-Sar10-Ala tail would be denoted as:

βAla-Sar10-A-(SEQ ID NO:X).

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa). For the avoidance of doubt, references to amino acids either as their full name or as their amino acid single or three letter codes are intended to be represented herein as L-amino acids unless otherwise stated. If such an amino acid is intended to be represented as a D-amino acid then the amino acid will be prefaced with a lower case d within square parentheses, for example [dA], [dD], [dE], [dK], [d1Nal], [dNle], etc.

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three reactive groups selected from cysteine, 3-mercaptopropionic acid and/or cysteamine and form at least two loops on the scaffold.

Reactive Groups

The molecular scaffold of the invention may be bonded to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group, such as penicillamine. Details of suitable reactive groups may be found in WO 2009/098450.

Examples of reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

The polypeptides of the invention contain at least three reactive groups. Said polypeptides can also contain four or more reactive groups. The more reactive groups are used, the more loops can be formed in the molecular scaffold.

In a preferred embodiment, polypeptides with three reactive groups are generated. Reaction of said polypeptides with a molecular scaffold/molecular core having a three-fold rotational symmetry generates a single product isomer. The generation of a single product isomer is favourable for several reasons. The nucleic acids of the compound libraries encode only the primary sequences of the polypeptide but not the isomeric state of the molecules that are formed upon reaction of the polypeptide with the molecular core. If only one product isomer can be formed, the assignment of the nucleic acid to the product isomer is clearly defined. If multiple product isomers are formed, the nucleic acid cannot give information about the nature of the product isomer that was isolated in a screening or selection process. The formation of a single product isomer is also advantageous if a specific member of a library of the invention is synthesized. In this case, the chemical reaction of the polypeptide with the molecular scaffold yields a single product isomer rather than a mixture of isomers.

In another embodiment, polypeptides with four reactive groups are generated. Reaction of said polypeptides with a molecular scaffold/molecular core having a tetrahedral symmetry generates two product isomers. Even though the two different product isomers are encoded by one and the same nucleic acid, the isomeric nature of the isolated isomer can be determined by chemically synthesizing both isomers, separating the two isomers and testing both isomers for binding to a target ligand.

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved.

In another embodiment, the reactive groups of the polypeptide of the invention are reacted with molecular linkers wherein said linkers are capable to react with a molecular scaffold so that the linker will intervene between the molecular scaffold and the polypeptide in the final bonded state.

In some embodiments, amino acids of the members of the libraries or sets of polypeptides can be replaced by any natural or non-natural amino acid. Excluded from these exchangeable amino acids are the ones harbouring functional groups for cross-linking the polypeptides to a molecular core, such that the loop sequences alone are exchangeable. The exchangeable polypeptide sequences have either random sequences, constant sequences or sequences with random and constant amino acids. The amino acids with reactive groups are either located in defined positions within the polypeptide, since the position of these amino acids determines loop size.

In one embodiment, a polypeptide with three reactive groups has the sequence $(X)_l Y(X)_m Y(X)_n Y(X)_o$, wherein Y represents an amino acid with a reactive group, X represents a random amino acid, m and n are numbers between 3 and 6 defining the length of intervening polypeptide segments, which may be the same or different, and l and o are numbers between 0 and 20 defining the length of flanking polypeptide segments.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination small molecules that bear the complementary reactive group, or by incorporating the unnatural amino acids into a chemically or recombinantly synthesised polypeptide when the molecule is being made after the selection/isolation phase. Further details can be found in WO 2009/098450 or Heinis et al., Nat Chem Biol 2009, 5 (7), 502-7.

In one embodiment, the reactive groups are selected from cysteine, 3-mercaptopropionic acid and/or cysteamine residues.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the invention contain an amine function, these may form quaternary ammonium salts, for example by reaction with an alkylating agent according to methods well known to the skilled person. Such quaternary ammonium compounds are within the scope of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:
  Incorporating hydrophobic moieties that exploit the hydrophobic effect and lead to lower off rates, such that higher affinities are achieved;
  Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and
  Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.
(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the Nectin-4 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment, the molecular scaffold may be a macromolecule. In one embodiment, the molecular scaffold is a macromolecule composed of amino acids, nucleotides or carbohydrates.

In one embodiment, the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of hexahydro-1,3,5-triazine, especially 1,3,5-Triacryloylhexahydro-1,3,5-triazine (TATA), or a derivative thereof.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene or iodoacetamide. Other scaffold reactive groups that are used to selectively couple compounds to cysteines in proteins are maleimides, αβ unsaturated carbonyl containing compounds and α-halomethylcarbonyl containing compounds. Examples of maleimides which may be used as molecular scaffolds in the invention include: tris-(2-maleimidoethyl) amine, tris-(2-maleimidoethyl)benzene, tris-(maleimido) benzene. An example of an αβ unsaturated carbonyl containing compound is 1,1',1"-(1,3,5-triazinane-1,3,5-triyl) triprop-2-en-1-one (TATA) (Angewandte Chemie, International Edition (2014), 53(6), 1602-1606). An example of an α-halomethylcarbonyl containing compound is N,N',N"-(benzene-1,3,5-triyl)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptides to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptides, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringers dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

According to a further aspect of the invention, there is provided a heterotandem bicyclic peptide complex as defined herein for use in preventing, suppressing or treating cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models. The invention is further described below with reference to the following examples.

EXAMPLES

In general, the heterotandem bicyclic peptide complexes of the invention may be prepared in accordance with the following general method:

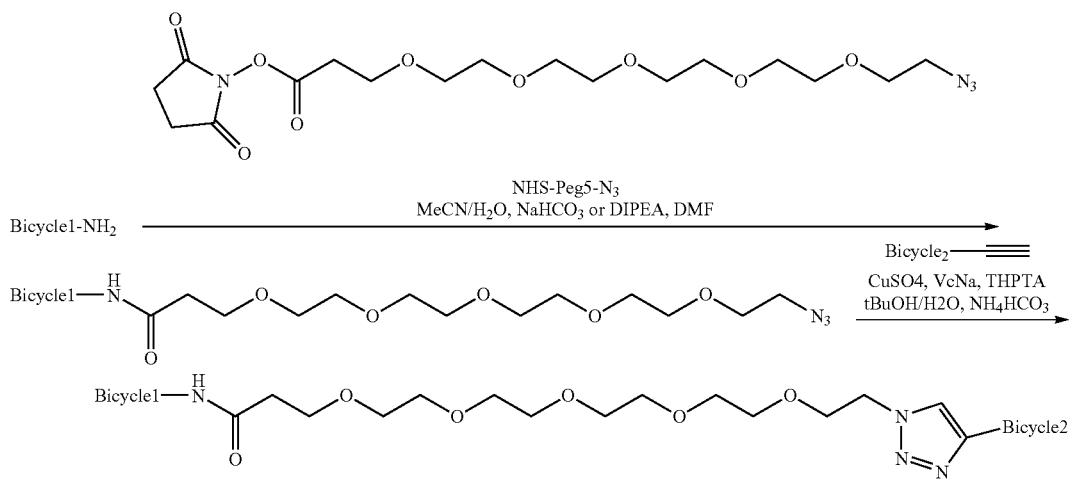

A mixture of Bicycle 1 (1.0 eq.) and NHS-PEG5-N3 (1.6 eq.) is dissolved in MeCN/H₂O (1:1), and the pH of the solution adjusted to 8 by dropwise addition of NaHCO₃ (0.1 M). The reaction mixture is stirred at 30° C. for 2 hr then concentrated under reduced pressure to remove solvent. The residue is then purified by prep-HPLC to give intermediate 2.

A mixture of intermediate 2 (1.0 eq) and Bicycle2 (1.0 eq) are dissolved in t-BuOH/H₂O (1:1), and then CuSO₄ (1.0 eq), VcNa (2.3 eq), and THPTA (1.0 eq) are added. Finally, 0.2 M NH₄HCO₃ is added to adjust pH to 8. The reaction mixture is stirred at 40° C. for 16 hr under N₂ atmosphere. The reaction mixture was directly purified by prep-HPLC.

More detailed experimental for selected heterotandem bicyclic peptide complexes of the invention are provided herein below:

Example 1: Synthesis of BCY12375

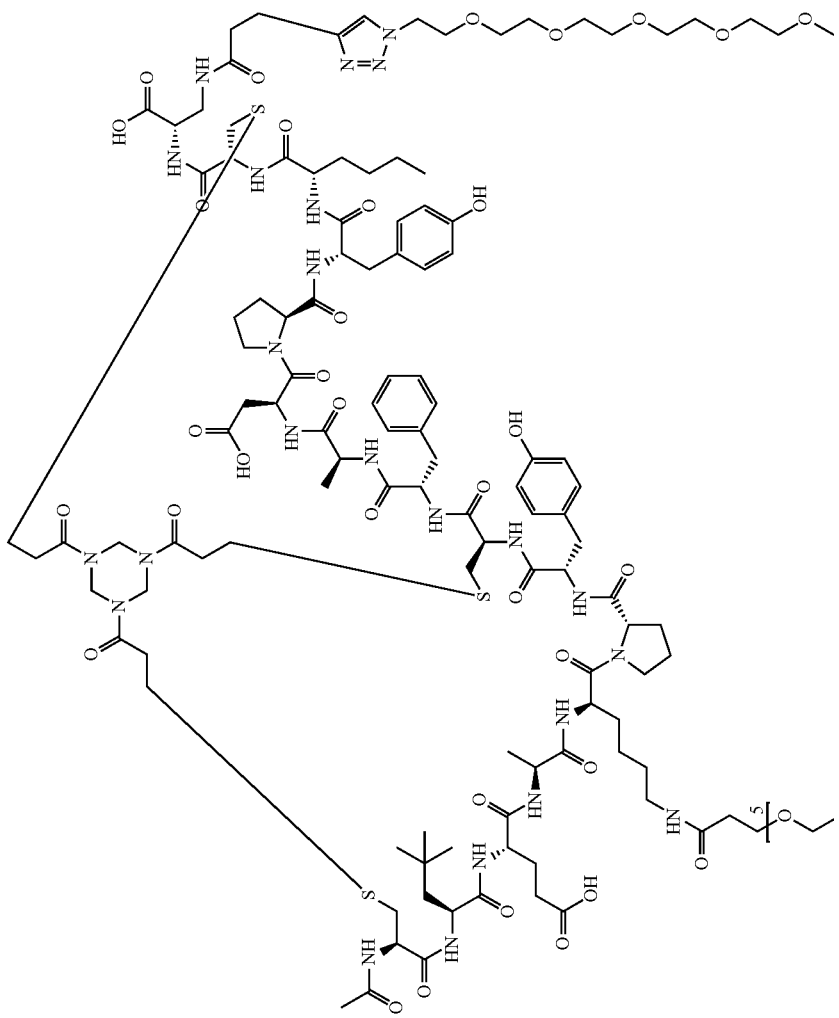

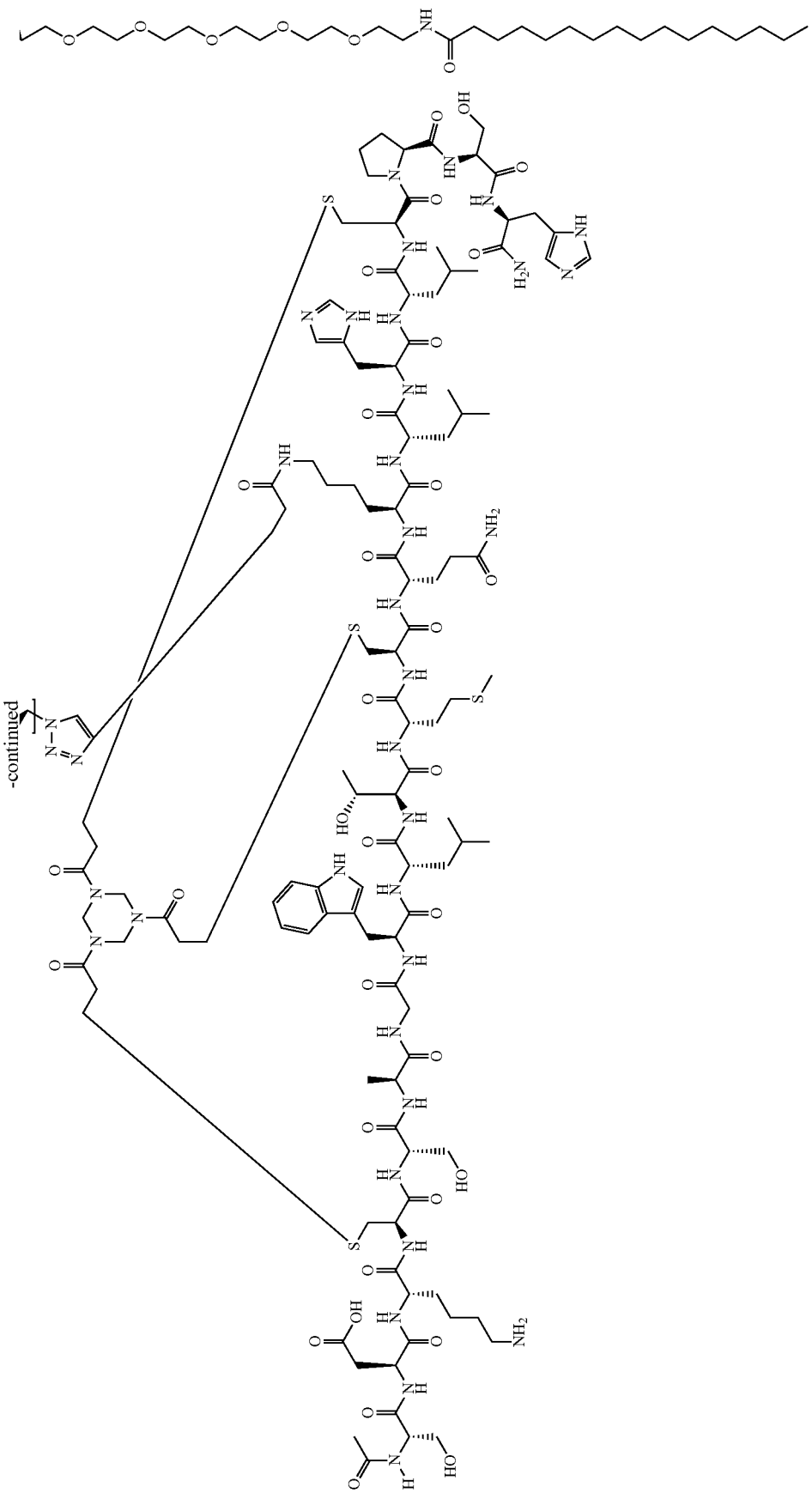

Procedure for Preparation of Palmitic Acid—PEG10-$N_3$

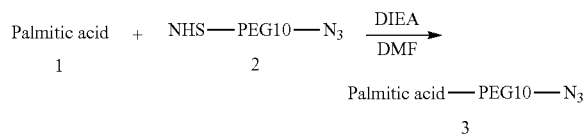

A mixture of Palmitic acid (100.0 mg, 282.89 μmol, 1.0 eq.), compound 2 (150.0 mg, 284.84 μmol, 1.0 eq.), and DIEA (74.5 mg, 574.11 μmol, 100.0 μL, 2.0 eq.) was dissolved in DMF (2 mL). The reaction mixture was stirred at 30° C. for 2 hr. LC-MS showed compound 1 was consumed completely and one main peak with desired m/z (MW: 765.03, observed m/z: 765.22) was detected. The reaction mixture was concentrated under reduced pressure to remove solvent and produced a residue. The residue was then purified by prep-HPLC (neutral condition). Palmitic acid—PEG10-$N_3$ (79.0 mg, 99.41 μmol, 35.14% yield, 96.27% purity) was obtained as a white solid.

Procedure for Preparation of Palmitic Acid-PEG10-BCY12023

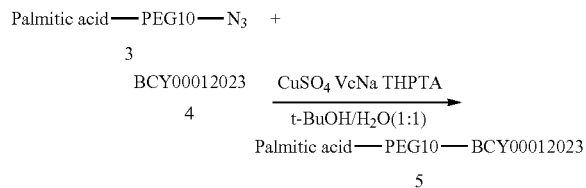

A mixture of compound 3 (50.0 mg, 22.07 μmol, 1.0 eq.), compound 2 (17.0 mg, 22.22 μmol, 1.0 eq.), and THPTA (10.0 mg, 23.02 μmol, 1.0 eq.) was dissolved in t-BuOH/$H_2O$ (1:1, 1 mL, pre-degassed and purged with $N_2$ for 3 times), and then $CuSO_4$ (0.4 M, 56.0 μL, 1.0 eq.) and VcNa (10.0 mg, 50.48 μmol, 2.3 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed Palmitic acid—PEG10-$N_3$ was remand and one main peak with desired m/z (calculated MW: 3030.60, observed m/z: 1010.35 ([M/3+H]+)) was detected. The reaction mixture was filtered and concentrated under reduced pressure to give a residue. The crude product was purified by prep-HPLC (TFA condition), and Palmitic acid—PEG10-BCY12023 (43.0 mg, 13.97 μmol, 63.30% yield, 98.46% purity) was obtained as a white solid.

Procedure for Preparation of Palmitic Acid—PEG10-BCY12023-PEG5-$N_3$

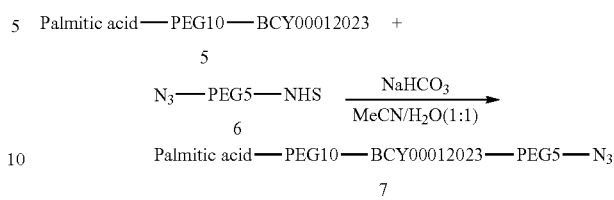

A mixture of compound 5 (43.0 mg, 14.19 μmol, 1.0 eq.), compound 6 (10.0 mg, 23.13 μmol, 1.6 eq.) was dissolved in MeCN/$H_2O$ (1:1, 1 mL), and then the pH of this solution was adjusted to 8 by dropwise addition of $NaHCO_3$ (0.1 M). The reaction mixture was stirred at 30° C. for 2 hr. LC-MS showed compound 5 was consumed completely and one main peak with desired m/z (MW: 3347.94, observed m/z: 1673.7 ([(M/2+$H^+$]), 1115.9 ([(M/3+$H^+$])) was detected. The reaction mixture was concentrated under reduced pressure to remove solvent and produced a residue. The residue was then purified by prep-HPLC (neutral condition). Palmitic acid—PEG10-BCY12023-PEG5-$N_3$ (16.0 mg, 4.43 μmol, 31.25% yield, 92.78% purity) was obtained as a white solid.

Procedure for Preparation of BCY12375

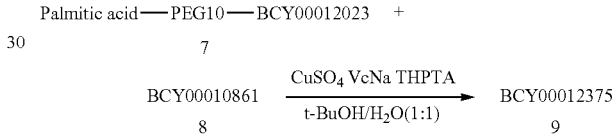

A mixture of compound 7 (8.0 mg, 2.39 μmol, 1.0 eq.), compound 8 (6.5 mg, 2.39 μmol, 1.0 eq.), and THPTA (1.1 mg, 2.53 μmol, 1.0 eq.) was dissolved in t-BuOH/$H_2O$ (1:1, 1 mL, pre-degassed and purged with $N_2$ for 3 times), and then $CuSO_4$ (0.4 M, 6.0 μL, 1.0 eq.) and VcNa (1.0 mg, 5.05 μmol, 2.1 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 16 hr under $N_2$ atmosphere. LC-MS showed compound 7 was remand and one main peak with desired m/z (calculated MW: 6064.08, observed m/z: 1516.4 ([M/4+H]+), 1212.8 ([M/5+H]+)) was detected. The reaction mixture was filtered and concentrated under reduced pressure to give a residue. The crude product was purified by prep-HPLC (TFA condition), and BCY12375 (6.2 mg, 0.99 μmol, 41.62% yield, 97.27% purity) was obtained as a white solid.

Example 2: Synthesis of BCY12021

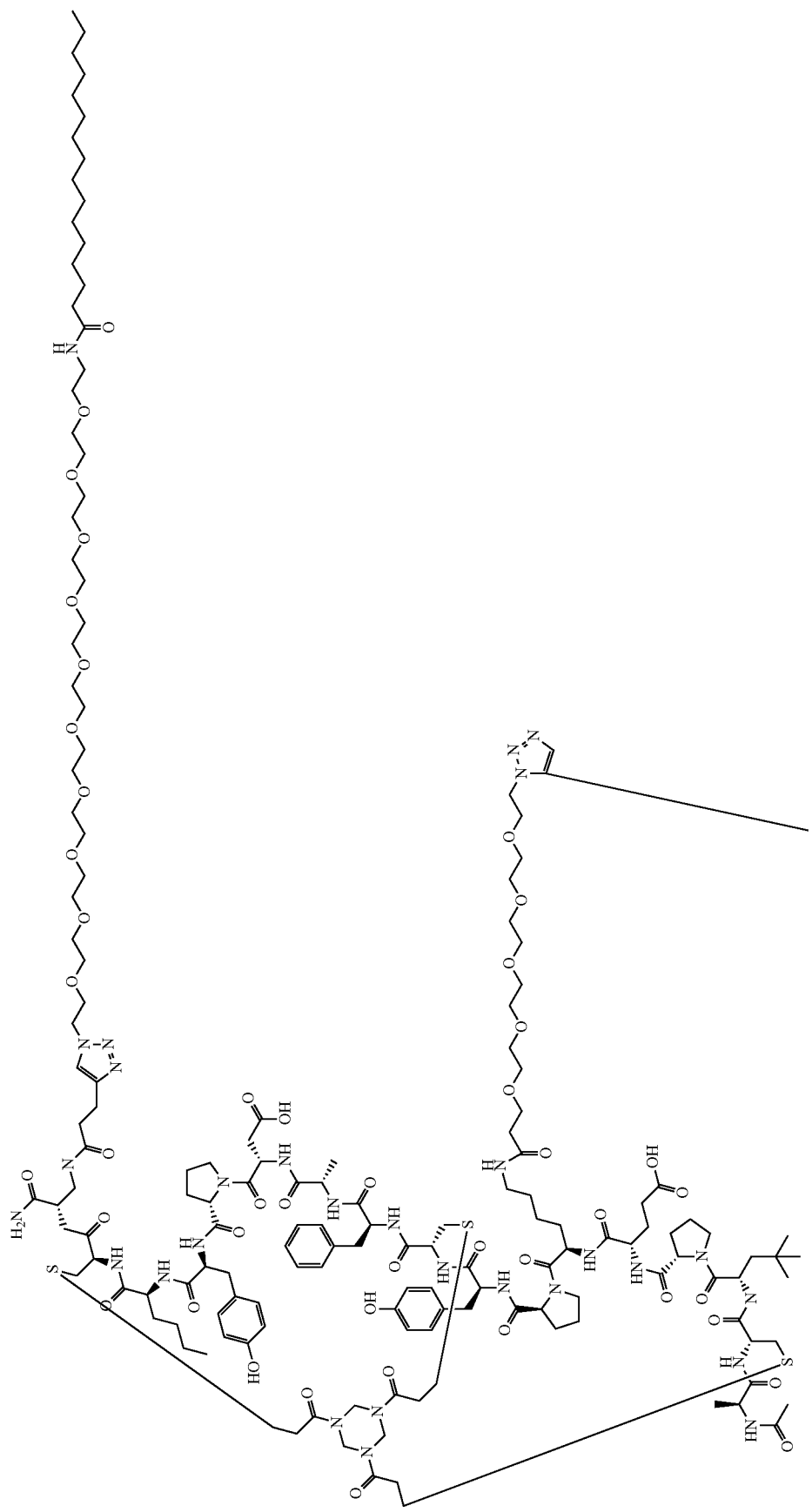

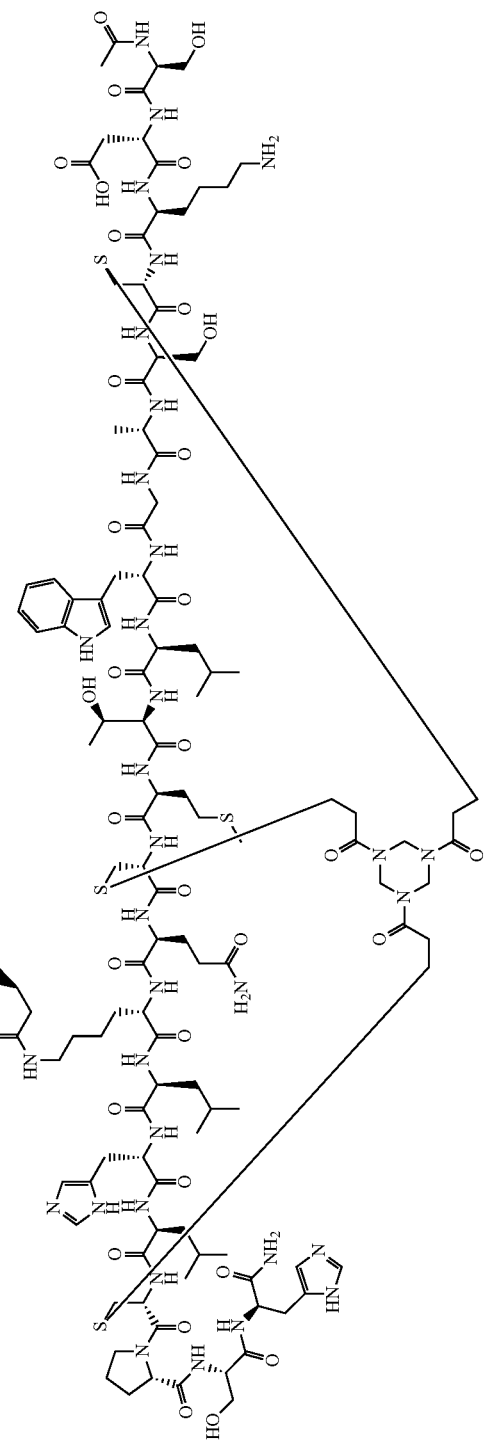

Procedure for Preparation of Palmitic Acid—PEG10-BCY11144

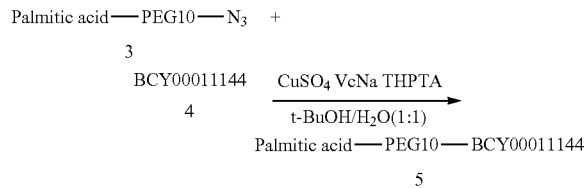

A mixture of compound 3 (160.0 mg, 69.45 μmol, 1.0 eq.), compound 4 (56.0 mg, 72.20 μmol, 1.0 eq.), and THPTA (35.0 mg, 80.55 μmol, 1.1 eq.) was dissolved in t-BuOH/H$_2$O (1:1, 2 mL, pre-degassed and purged with N$_2$ for 3 times), and then CuSO$_4$ (0.4 M, 56.0 μL, 1.0 eq.) and VcNa (30.0 mg, 151.43 μmol, 2.2 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 16 hr under N$_2$ atmosphere. LC-MS showed one main peak with desired m/z (calculated MW: 3068.70, observed m/z: 1533.81 ([M/2+H]$^+$), 1023.43 ([M/3+H]$^+$)) was detected. The reaction mixture was filtered and concentrated under reduced pressure to give a residue. The crude product was purified by prep-HPLC (TFA condition), and Palmitic acid—PEG10-BCY11144 (150.0 mg, 46.83 μmol, 67.42% yield, 95.80% purity) was obtained as a white solid.

Procedure for Preparation of Palmitic Acid—PEG10-BCY11144-PEG5-N$_3$

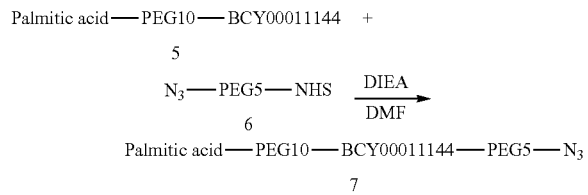

A mixture of compound 5 (47.0 mg, 15.32 μmol, 1.0 eq.), compound 6 (7.0 mg, 16.19 μmol, 1.0 eq.), and DIEA (3.0 mg, 22.97 μmol, 4.0 μL, 1.5 eq.) was dissolved in DMF (1 mL). The reaction mixture was stirred at 30° C. for 2 hr. LC-MS showed compound 5 was consumed completely and one main peak with desired m/z (MW: 3386.03, observed m/z: 1693.21 ([M/2+H]$^+$), 1129.13 ([M/3+H]$^+$)) was detected. The reaction mixture was concentrated under reduced pressure to remove solvent and produced a residue. The residue was then purified by prep-HPLC (neutral condition). Palmitic acid—PEG10-BCY11144-PEG5-N$_3$ (20.0 mg, 5.72 μmol, 37.33% yield, 96.79% purity) was obtained as a white solid.

Procedure for Preparation of BCY12021

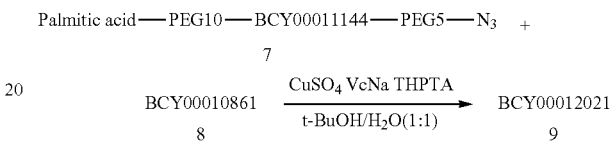

A mixture of compound 7 (10.0 mg, 2.95 μmol, 1.0 eq.), compound 8 (8.2 mg, 3.02 μmol, 1.0 eq.), and THPTA (1.5 mg, 3.45 μmol, 1.1 eq.) was dissolved in t-BuOH/H$_2$O (1:1, 1 mL, pre-degassed and purged with N$_2$ 3 times), and then CuSO$_4$ (0.4 M, 8.0 μL, 1.0 eq.) and VcNa (1.5 mg, 7.57 μmol, 2.5 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 16 hr under N$_2$ atmosphere. LC-MS showed one main peak with desired m/z (calculated MW: 6102.17, observed m/z: 1525.17 ([M/4+H]$^+$), 1221.3 ([M/5+H]$^+$)). The reaction mixture was filtered and concentrated under reduced pressure to give a residue. The crude product was purified by prep-HPLC (TFA condition), and BCY12021 (6.6 mg, 1.02 μmol, 34.62% yield, 94.54% purity) was obtained as a white solid.

Example 3: Synthesis of BCY11468

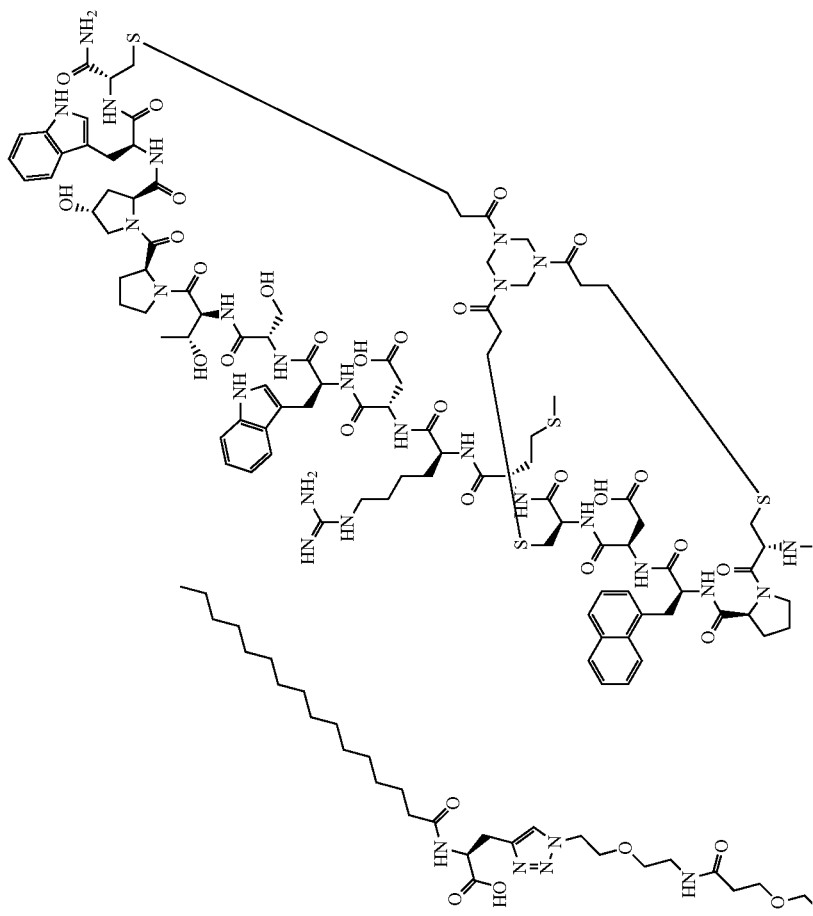

-continued
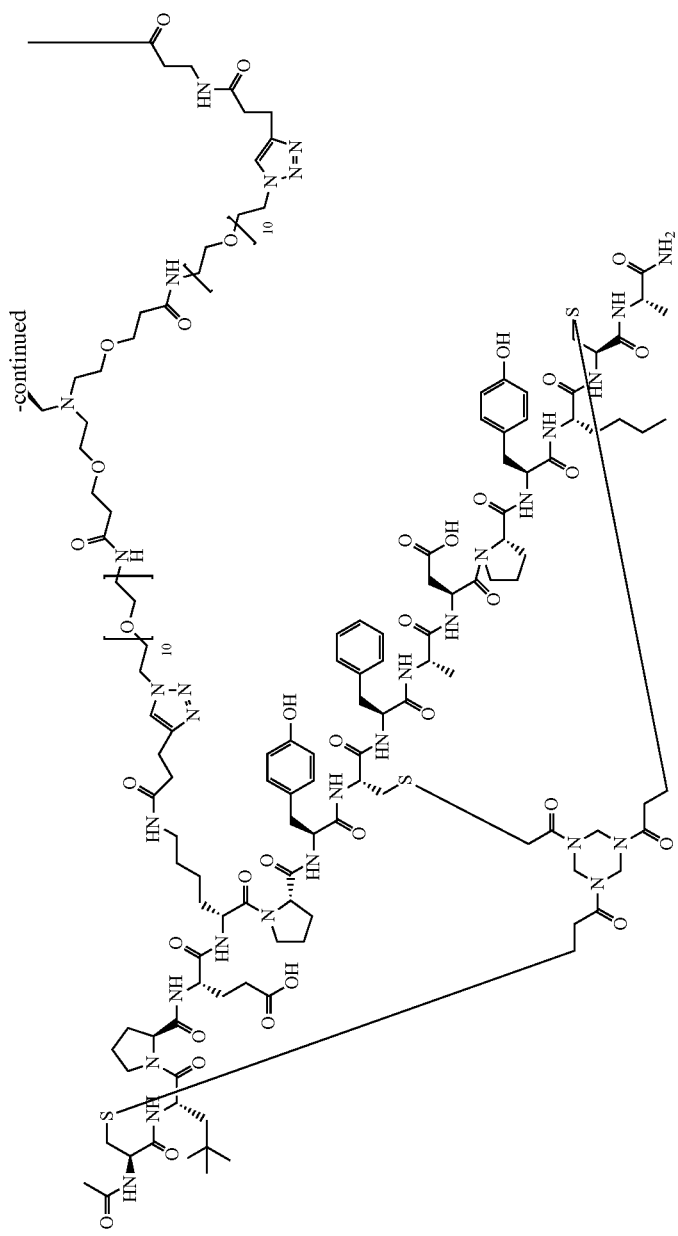

Procedure for Preparation of COM113

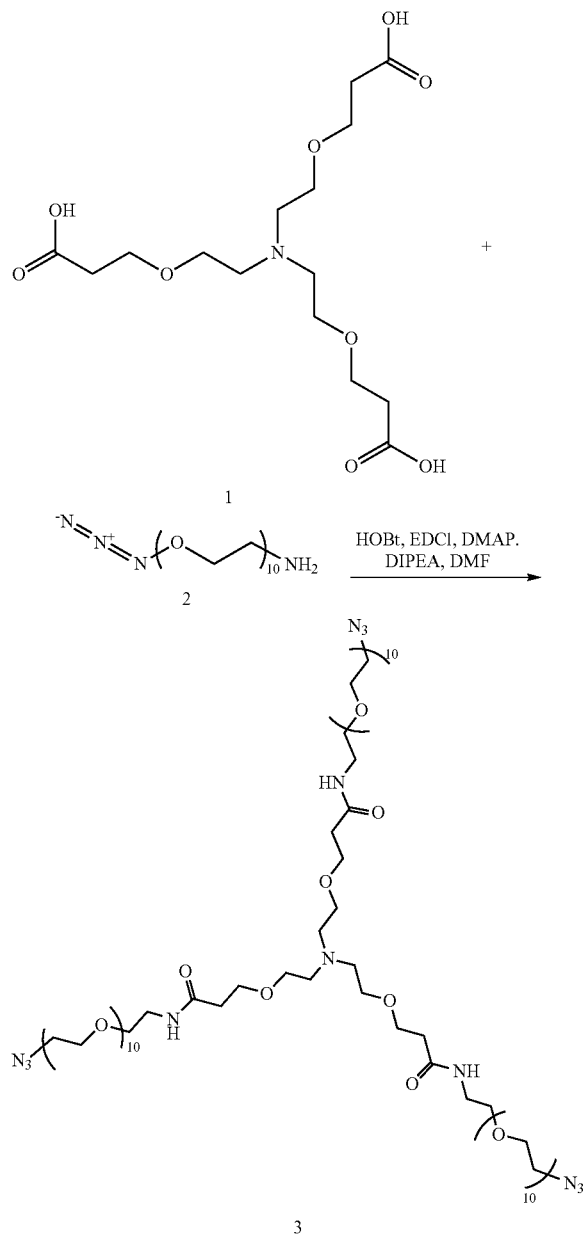

A mixture of compound 1 (50.0 mg, 124.4 μmol, 1.0 eq), EDCl (95.4 mg, 497.7 μmol, 4.0 eq), HOBt (55.5 mg, 410.6 μmol, 3.3 eq), and DMAP (15.2 mg, 124.4 μmol, 1.0 eq) was dissolved in 2 mL DMF, and then DIEA (134.9 mg, 1.04 mmol, 181.8 μL, 8.4 eq) was added to generate a homogenous solution. Next, compound 2 (200.0 mg, 379.8 μmol, 3.05 eq) dissolved in DMF (2 mL) was added to this solution dropwise. The reaction mixture was stirred at 30° C. for 16 hr. LC-MS showed compound 1 was consumed completely and one main peak with desired m/z (MW: 1891.19, observed m/z: 945.8600 ([M/2+H$^+$]) and 612.4400 ([(M-3H$_2$O)/3+H$^+$])) was detected. The reaction mixture was directly purified by prep-HPLC (TFA condition), resulting in COM113 (161 mg, 85.67 μmol, 68% yield) as a yellow oil after lyophilization.

Procedure for Preparation of COM113-BCY8928

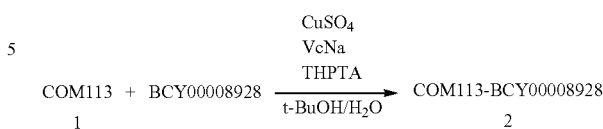

COM113 (50.0 mg, 26.44 μmol, 1.0 eq) and BCY8928 (53.0 mg, 23.9 μmol, 0.9 eq) were first dissolved in 2 mL of t-BuOH/H$_2$O (1:1), and then CuSO$_4$ (0.4 M, 66.1 μL, 1.0 eq), VcNa (10.5 mg, 53.0 μmol, 2.0 eq) and THPTA (23.0 mg, 52.93 μmol, 2.0 eq) was added. Finally, 1 M NH$_4$HCO$_3$ was added to adjust pH to 8. All solvents were degassed and purged with N$_2$ for 3 times. The reaction mixture was stirred at 30° C. for 16 hr under N$_2$ atmosphere. LC-MS showed one main peak with desired m/z (calculated MW: 4108.77 observed m/z: 1369.97 ([M/3+H]$^+$)). The reaction mixture was purified by prep-HPLC (TFA condition) and Compound 2 (14.0 mg, 3.21 μmol, 12.14% yield, 94.16% purity) was obtained as a white solid.

Procedure for Preparation of Palmitic Acid NHS Ester

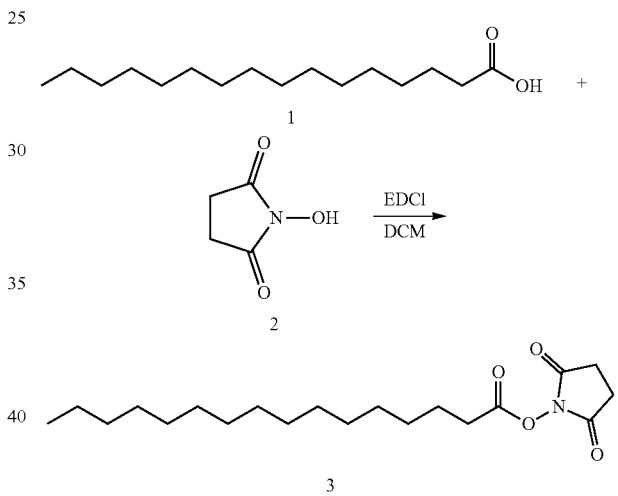

To a solution of palmitic acid (500 mg, 1.95 mmol, 586.85 μL, 1.0 eq), 1-hydroxypyrrolidine-2,5-dione (250 mg, 2.17 mmol, 1.11 eq) in DCM (5 mL) was added with EDCl (747.60 mg, 3.90 mmol, 2.0 eq). The mixture was stirred at 30° C. for 16 hr. TLC indicated Reactant 1 was consumed completely and one new spot formed. The reaction was clean according to TLC. The reaction mixture was filtered and concentrated under reduced pressure to give a residue. The residue was purified by column chromatography (SiO2, DCM:MeOH=0 to 100:1). The desired product was dried to obtain Palmitic acid NHS ester (0.68 g, 1.92 mmol, 98.65% yield) as a white solid.

Procedure for Preparation of Palmitic Acid-Propargylalanine

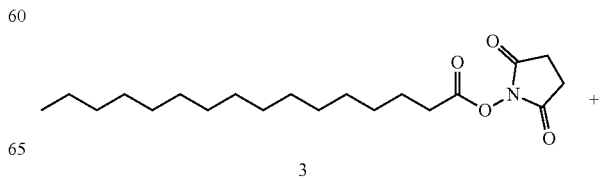

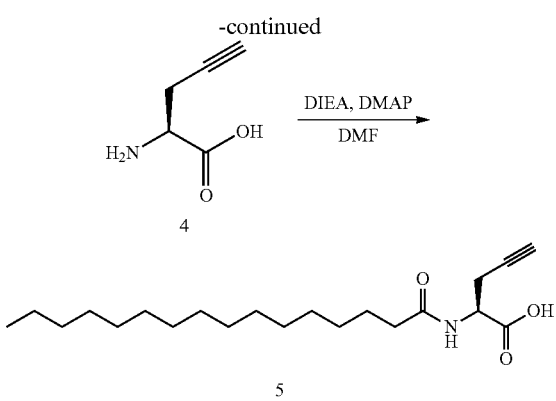

To a solution of compound 3 (120 mg, 339.47 μmol, 1.0 eq) and compound 4 (57.60 mg, 509.20 μmol, 1.5 eq) in DMF (6 mL) was added DIEA (131.62 mg, 1.02 mmol, 177.39 μL, 3.0 eq) and DMAP (41.47 mg, 339.47 μmol, 1.0 eq). The mixture was stirred at 40° C. for 16 hr. LC-MS showed Reactant 3 was consumed completely and one main peak with desired m/z or desired mass was detected. The reaction mixture was filtered and concentrated under reduced pressure to give a residue. The residue was purified by prep-HPLC (TFA condition). Palmitic acid-Propargylalanine (90 mg, 256.03 μmol, 75.42% yield) was obtained as a white solid.

Procedure for Preparation of COM113-BCY8928-Palmitic Acid

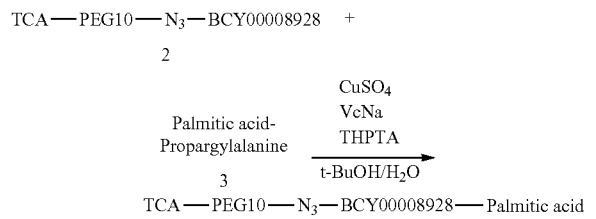

Compound 2 (14.0 mg, 3.41 μmol, 1.0 eq) and Compound 3 (1.1 mg, 3.13 μmol, 0.9 eq) were first dissolved in 2 mL of t-BuOH/H$_2$O (1:1), and then CuSO$_4$ (0.4 M, 10.0 μL, 1.1 eq), VcNa (2.0 mg, 10.1 μmol, 2.9 eq) and THPTA (2.0 mg, 4.6 μmol, 1.3 eq) was added. Finally 0.2 M NH$_4$HCO$_3$ was added to adjust pH to 8. All solvents here were degassed and purged with N$_2$ for 3 times. The reaction mixture was stirred at 35° C. for 16 hr under N$_2$ atmosphere. LC-MS showed one main peak with desired m/z (calculated MW: 4460.29, observed m/z: 1486.92 ([M/3+H]$^+$), 1115.58 ([M/4+H]$^+$), 895.83 ([M/5+H]$^+$)). The reaction mixture was purified by prep-HPLC (TFA condition) and Compound 4 (5.9 mg, 1.28 μmol, 37.66% yield, 97.0% purity) was obtained as a white solid.

Procedure for Preparation of BCY11468

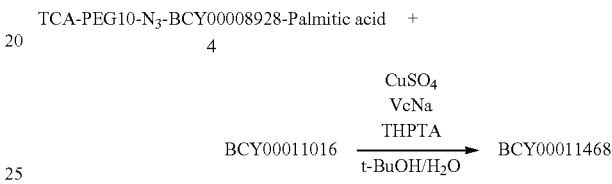

Compound 4 (5.9 mg, 1.32 μmol, 1.0 eq) and BCY11016 (3.0 mg, 1.29 μmol, 1 eq) were first dissolved in 2 mL of t-BuOH/H$_2$O (1:1), and then CuSO$_4$ (0.4 M, 8.0 μL, 2.4 eq), VcNa 2.0 mg, 7.6 eq) and THPTA (2.0 mg, 3.5 eq) was added. Finally, 1 M NH$_4$HCO$_3$ was added to adjust pH to 8. All solvents were degassed and purged with N$_2$ 3 times. The reaction mixture was stirred at 30° C. for 16 hr under N$_2$ atmosphere. LC-MS showed one main peak with desired m/z (calculated MW: 6783.93, observed m/z: 1131.7 ([M/6+H]$^+$)). The reaction mixture was purified by prep-HPLC (TFA condition) and BCY11468 (2.2 mg, 0.312 μmol, 23.57% yield, 96.16% purity) was obtained as a white solid.

Example 4: Synthesis of BCY11618

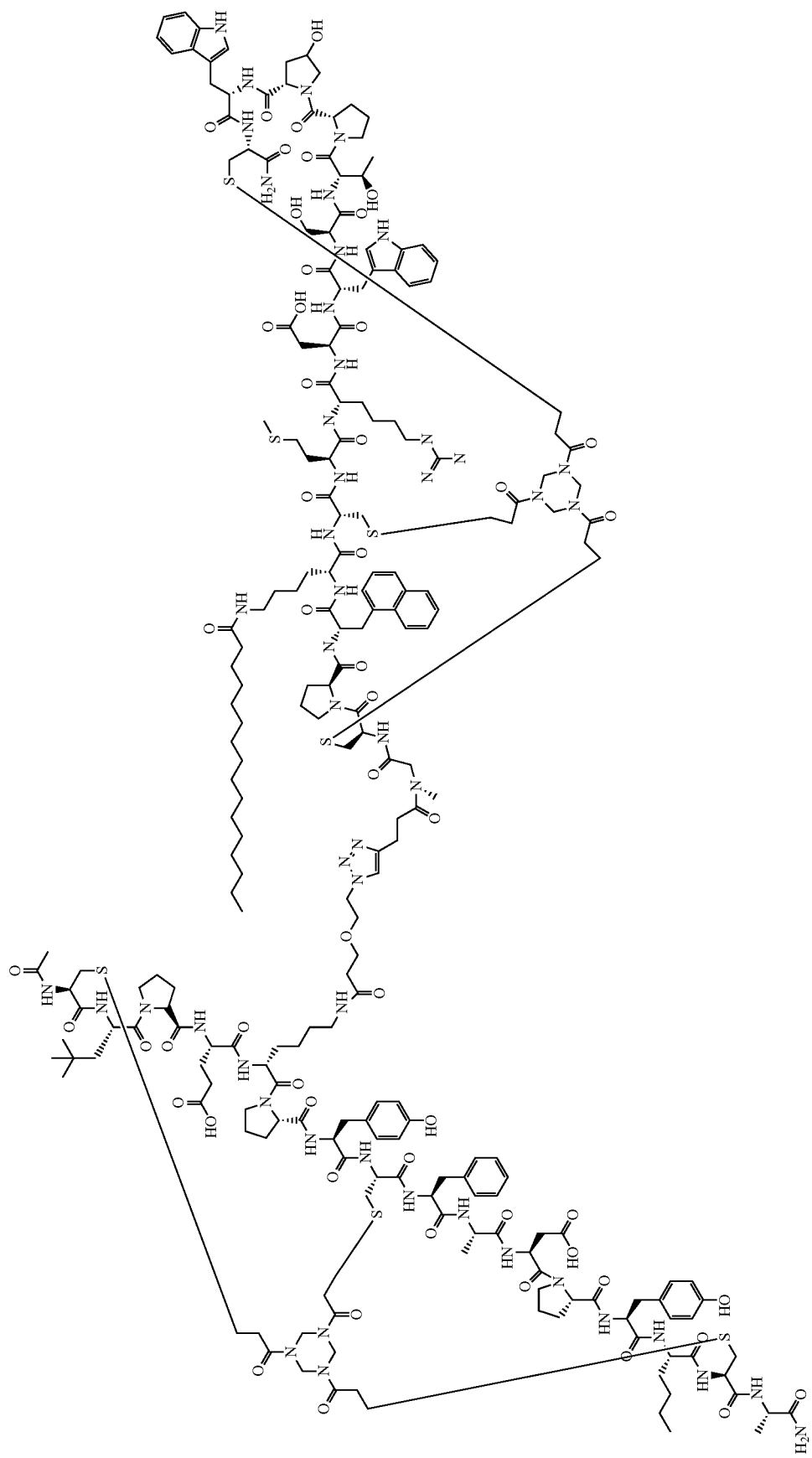

Procedure for Preparation of BCY8920-PEG5-N$_3$

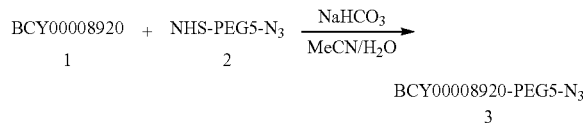

A mixture of BCY8920 (50.0 mg, 23.39 μmol, 1.0 eq.), compound 2 (10.2 mg, 23.51 μmol, 1.01 eq.) and NaHCO$_3$ (2.0 mg, 24.8 μmol, 1.0 eq.) was dissolved in MeCN/H$_2$O (1:1, 2 mL). The reaction mixture was stirred at 40° C. for 2 hr, until LC-MS showed BCY8920 was consumed completely and one main peak with desired m/z (calculated MW: 2454.83, observed m/z: 1227.67 ([M/2+1-1]$^+$) and 818.74 ([M/3+1-1]$^+$)) was detected. The reaction mixture was then concentrated under reduced pressure to remove solvent and produced a residue, following by purification by prep-HPLC (TFA condition). BCY8920-PEG5-N$_3$ (25 mg, 9.70 μmol, 41.47% yield, 95.26% purity) was obtained as a white solid.

Procedure for Preparation of BCY11143-dK(Palmitic Acid)

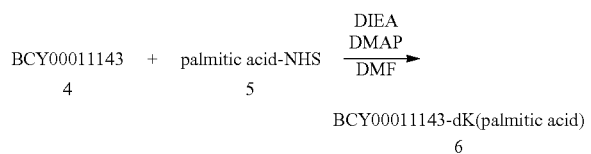

A mixture of BCY11143 (30.0 mg, 12.84 μmol, 1.0 eq.), compound 5 (5.0 mg, 14.12 μmol, 1.1 eq.), DIEA (1.7 mg, 12.84 μmol, 2.2 μL, 1.0 eq.) and DMAP (1.6 mg, 12.84 μmol, 1.0 eq.) was dissolved in DMF. The reaction mixture was stirred at 40° C. for 2 hr under N$_2$ atmosphere. LC-MS showed one main peak with desired m/z (calculated MW: 2575.14, observed m/z: 1287.68 ([M/2+H$^+$])) was detected. The reaction mixture was filtered and concentrated under reduced pressure to give a residue, which was then purified by prep-HPLC (TFA condition). BCY11143-dK(palmitic acid) (18.3 mg, 6.95 μmol, 54.17% yield, 97.86% purity) was obtained as a white solid.

Procedure for Preparation of BCY11618

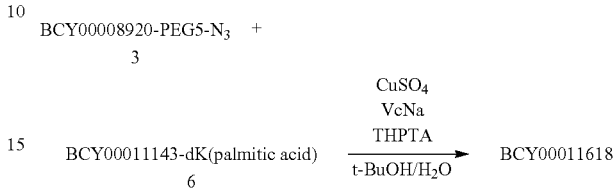

A mixture of compound 3 (5 mg, 2.04 μmol, 1.0 eq.), compound 6 (5.8 mg, 2.3 μmol, 1.1 eq.), and THPTA (0.9 mg, 2.07 μmol, 1.0 eq.) was dissolved in t-BuOH/H$_2$O (1:1, 1 mL, pre-degassed and purged with N$_2$ for 3 times), and then CuSO$_4$ (0.4 M, 5.1 μL, 1.0 eq.) and VcNa (0.4 M, 5.1 μL, 1.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 6 hr under N$_2$ atmosphere. LC-MS showed compound 3 was consumed completely and one main peak with desired m/z (calculated MW: 5029.97, observed m/z: 1257.8 ([M/4+H]$^+$) and 1006.6 ([M/5+H]$^+$)) was detected. The reaction mixture was filtered and concentrated under reduced pressure to give a residue. The crude product was purified by prep-HPLC (TFA condition), and BCY11618 (5.3 mg, 1.0 μmol, 49.15% yield, 95% purity) was obtained as a white solid.

Example 5: Synthesis of BCY11776

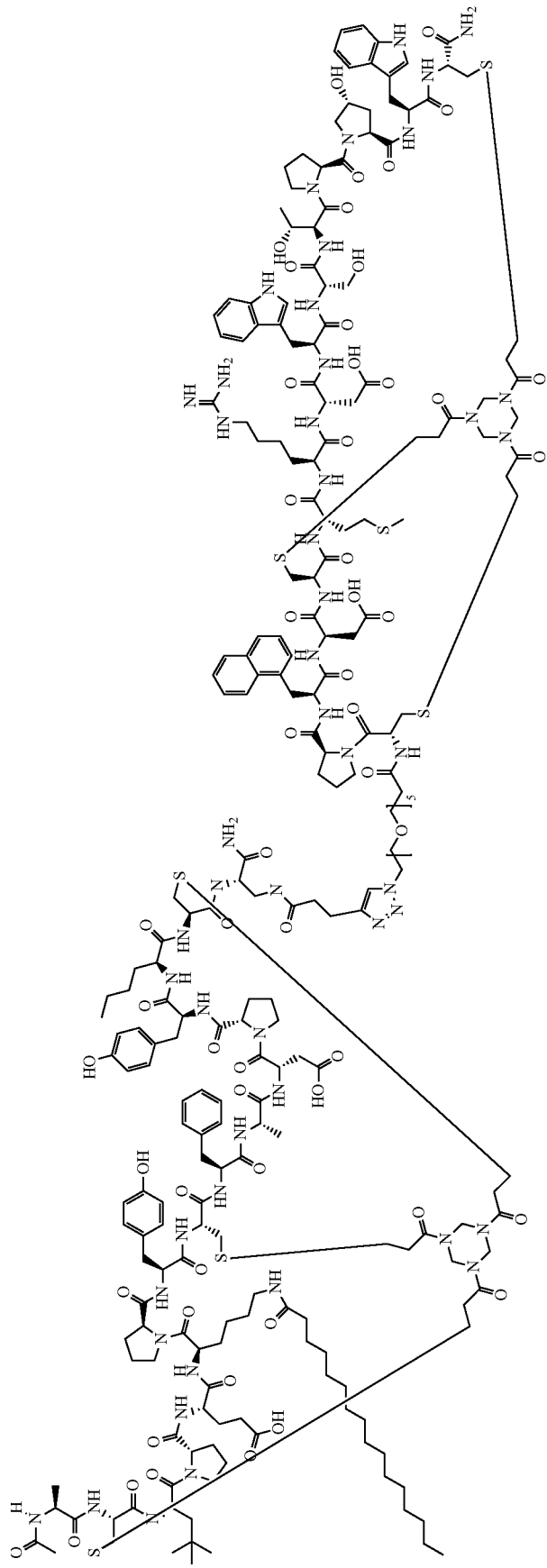

Procedure for Preparation of BCY8116-Peg5-N$_3$

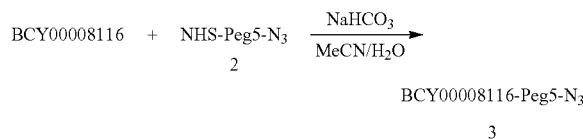

A mixture of BCY8116 (50.0 mg, 23.39 μmol, 1.0 eq.), compound 2 (10.2 mg, 23.51 μmol, 1.01 eq.) and NaHCO$_3$ (2.0 mg, 24.8 μmol, 1.0 eq.) was dissolved in MeCN/H$_2$O (1:1, 2 mL). The reaction mixture was stirred at 25° C. for 1 hr until LC-MS showed BCY8116 was consumed completely and one main peak with desired m/z (calculated MW: 2454.83, observed m/z: 1227.67 ([M/2+H$^+$]), 818.74 ([M/3+H$^+$])) was detected. The reaction mixture was then concentrated under reduced pressure to remove solvent and produced a residue, following by purification by prep-HPLC (TFA condition). Compound 3 (25.0 mg, 9.70 μmol, 41.47% yield, 95.26% purity) was obtained as a white solid.

Procedure for Preparation of Compound BCY11144-dK (Palmitic Acid)

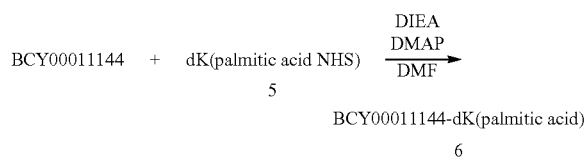

A mixture of BCY11144 (50.0 mg, 21.7 μmol, 1.0 eq.), compound 5 (8.5 mg, 23.87 μmol, 1.1 eq.), DIEA (2.81 mg, 21.7 μmol, 4.0 μL, 1.0 eq.) and DMAP (2.7 mg, 21.7 μmol, 1.0 eq.) was dissolved in DMF. The reaction mixture was stirred at 25° C. for 2 hr under N$_2$ atmosphere. LC-MS showed compound 3 was consumed completely and one main peak with desired m/z (calculated MW: 2542.08, observed m/z: 1271.7 ([M/2+H$^+$])) was detected. The reaction mixture was filtered and concentrated under reduced pressure to give a residue, which was then purified by prep-HPLC (TFA condition). Compound 6 (18.3 mg, 6.95 μmol, 54.17% yield, 96.68% purity) was obtained as a white solid.

Procedure for Preparation of BCY11776

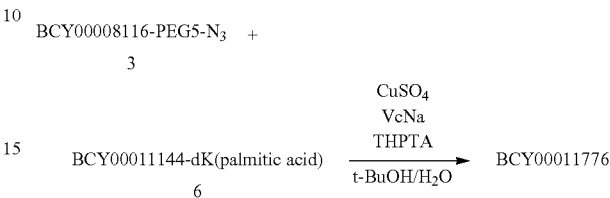

A mixture of compound 3 (10 mg, 4.0 μmol, 1.0 eq.), compound 6 (11.2 mg, 4.4 μmol, 1.1 eq.), and THPTA (1.8 mg, 1.0 eq.) was dissolved in t-BuOH/H$_2$O (1:1, 1 mL, pre-degassed and purged with N$_2$ for 3 times), and then CuSO$_4$ (0.4 M, 5.1 μL, 1 eq.) and VcNa (0.4 M, 5.1 μL, 1 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 6 hr under N$_2$ atmosphere. LC-MS showed compound 3 was consumed completely and one main peak with desired m/z (calculated MW: 5031.9, observed m/z: 1258.52 ([M/4+H$^+$]), 1006.7 ([M/5+H$^+$])) was detected. The reaction mixture was filtered and concentrated under reduced pressure to give a residue. The crude product was purified by prep-HPLC (TFA condition), and BCY11776 (12.5 mg, 2.4 μmol, 60.11% yield, 96.6% purity) was obtained as a white solid.

Example 6: Synthesis of BCY11860

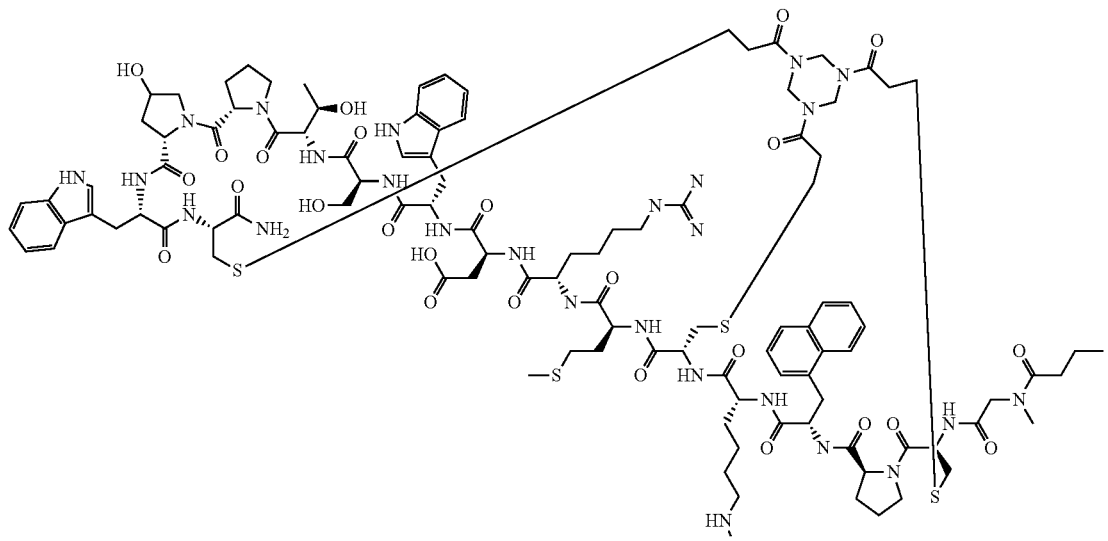

-continued
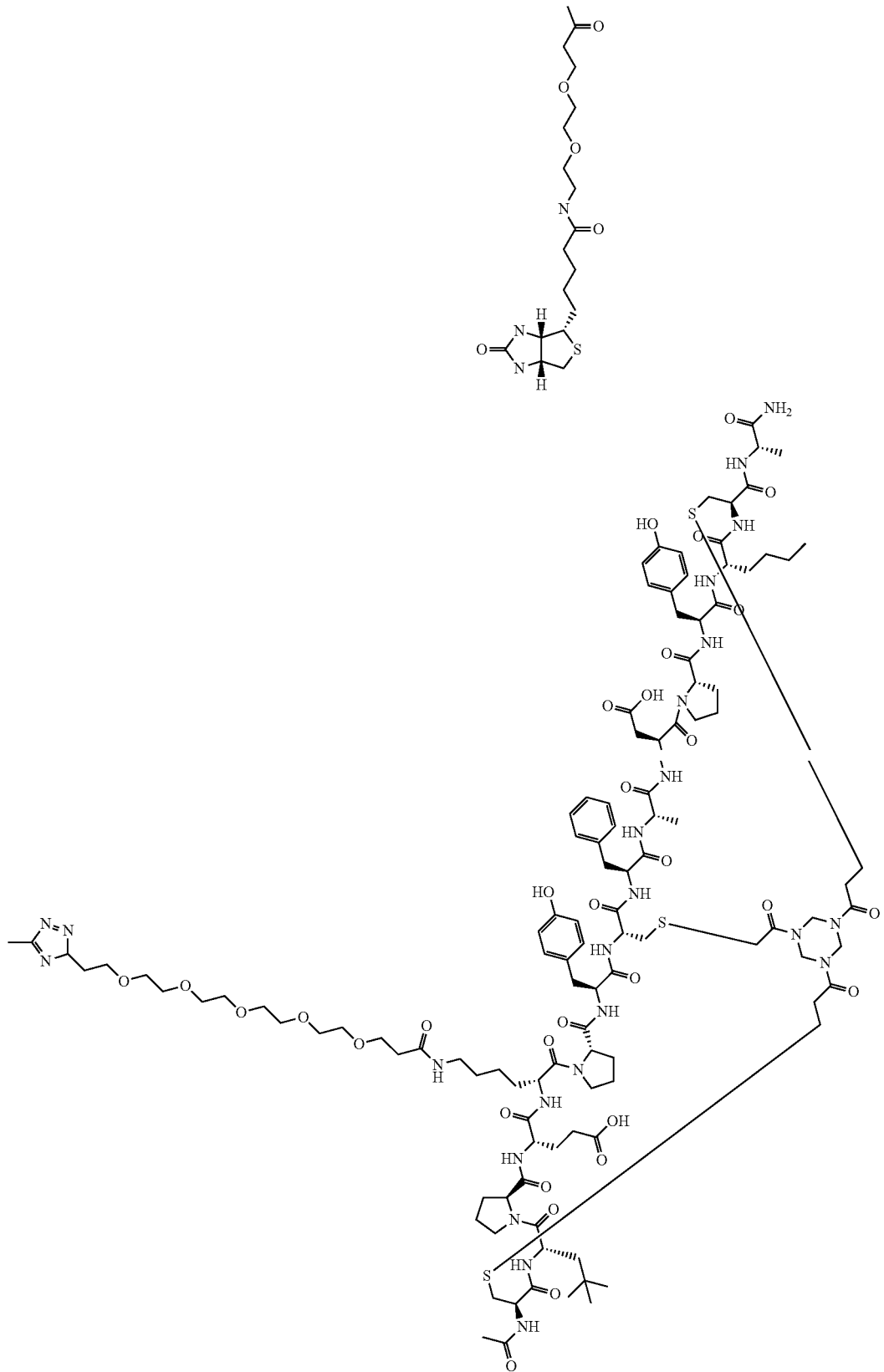

Procedure for Preparation of BCY8920-Peg5-BCY11143

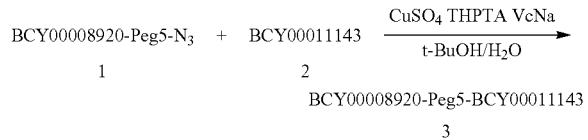

A mixture of BCY8920-PEG5-N$_3$ (20.0 mg, 8.15 μmol, 1.0 eq.), compound 2 (21.0 mg, 8.96 μmol, 1.1 eq.), and THPTA (0.4 M, 21.0 μL, 1.0 eq.) was dissolved in t-BuOH/H$_2$O (1:1, 1 mL, pre-degassed and purged with N$_2$ for 3 times), and then CuSO$_4$ (0.4 M, 21.0 μL, 1.0 eq.) and VcNa (0.4 M, 21.0 μL, 1.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 4 hr under N$_2$ atmosphere. LC-MS showed compound 1 was consumed completely and one main peak with desired m/z (calculated MW: 4791.56, observed m/z: 1597.28 ([M/3+H]$^+$), 1198.18 ([M/4+H]$^+$)) was detected. The reaction mixture was filtered and concentrated under reduced pressure to give a residue. The crude product was purified by prep-HPLC (TFA condition), and BCY8920-Peg5-BCY11143 (22.5 mg, 4.25 μmol, 52.13% yield, 90.44% purity) was obtained as a white solid.

Procedure for Preparation of BCY11860

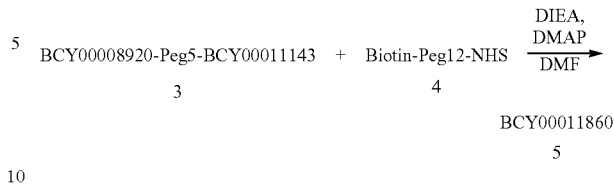

A mixture of compound 3 (5.0 mg, 1.04 μmol, 1.0 eq.), compound 4 (1.08 mg, 1.15 μmol, 1.1 eq.), and DIEA (0.4 M, 1.04 μmol, 3.0 μL, 1.0 eq.) and DMAP (0.2 mg, 1.04 μmol, 1.0 eq.) was dissolved in DMF (1.0 mL). The reaction mixture was stirred at 30° C. for 2 hr. LC-MS showed compound 3 was consumed completely and one main peak with desired m/z (MW: 5617.56, observed m/z: 1404.56 ([(M/4+H$^+$])) was detected. The reaction mixture was concentrated under reduced pressure to remove solvent and produced a residue. The residue was then purified by prep-HPLC (neutral condition). BCY11860 (2.9 mg, 0.48 μmol, 45.86% yield, 92.70% purity) was obtained as a white solid.

Example 7: Synthesis of BCY12020

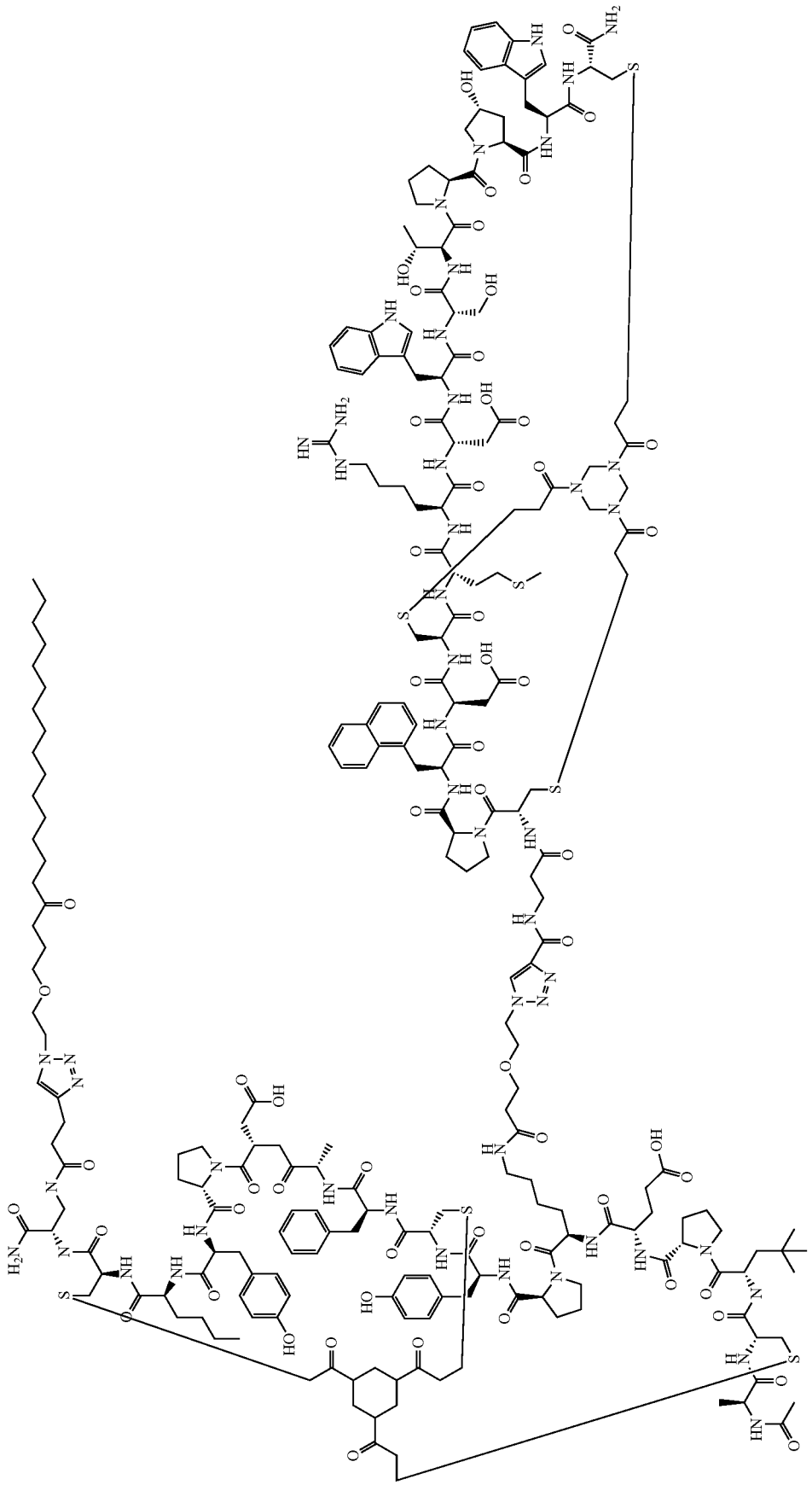

Procedure for Preparation of Palmitic Acid-PEG10-$N_3$

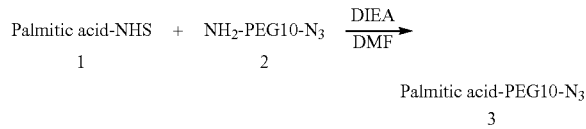

A mixture of Palmitic acid-NHS (100.0 mg, 282.89 μmol, 1.0 eq.), compound 2 (150.0 mg, 284.84 μmol, 1.0 eq.), and DIEA (74.5 mg, 574.11 μmol, 100.0 μL, 2.0 eq.) was dissolved in DMF (2 mL). The reaction mixture was stirred at 30° C. for 2 hr. LC-MS showed compound 1 was consumed completely and one main peak with desired m/z (MW: 765.03, observed m/z: 765.22) was detected. The reaction mixture was concentrated under reduced pressure to remove solvent and produced a residue. The residue was then purified by prep-HPLC (neutral condition). Palmitic acid-PEG10-$N_3$ (79.0 mg, 99.41 μmol, 35.14% yield, 96.27% purity) was obtained as a white solid.

Procedure for Preparation of Palmitic Acid-PEG10-BCY11144

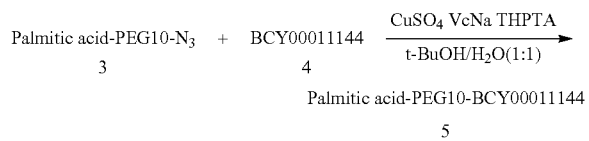

A mixture of compound 3 (160.0 mg, 69.45 μmol, 1.0 eq.), compound 2 (56.0 mg, 72.20 μmol, 1.0 eq.), and THPTA (35.0 mg, 80.55 μmol, 1.1 eq.) was dissolved in t-BuOH/$H_2O$ (1:1, 2 mL, pre-degassed and purged with $N_2$ 3 times), and then $CuSO_4$ (0.4 M, 56.0 μL, 1.0 eq.) and VcNa (30.0 mg, 151.43 μmol, 2.2 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 16 hr under $N_2$ atmosphere. LC-MS showed one main peak with desired m/z (calculated MW: 3068.70, observed m/z: 1533.81 ($[M/2+H]^+$), 1023.43 ($[M/3+H]^+$)). The reaction mixture was filtered and concentrated under reduced pressure to give a residue. The crude product was purified by prep-HPLC (TFA condition), and Palmitic acid-PEG10-BCY11144 (150.0 mg, 46.83 μmol, 67.42% yield, 95.80% purity) was obtained as a white solid.

Procedure for Preparation of Palmitic Acid-PEG10-BCY11144-PEG5-$N_3$

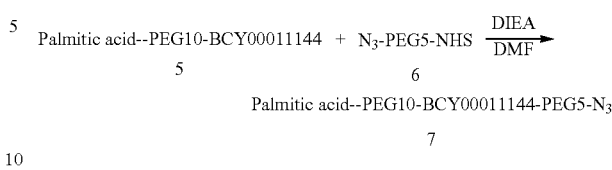

A mixture of compound 5 (47.0 mg, 15.32 μmol, 1.0 eq.), compound 6 (7.0 mg, 16.19 μmol, 1.1 eq.), and DIEA (3.0 mg, 22.97 μmol, 4.0 μL, 1.5 eq.) was dissolved in DMF (1 mL). The reaction mixture was stirred at 30° C. for 2 hr. LC-MS showed compound 5 was consumed completely and one main peak with desired m/z (MW: 3386.03, observed m/z: 1693.21 ($[M/2+H]^+$), 1129.13 ($[M/3+H]^+$)) was detected. The reaction mixture was concentrated under reduced pressure to remove solvent and produced a residue. The residue was then purified by prep-HPLC (neutral condition). Palmitic acid-PEG10-BCY11144-PEG5-$N_3$ (20.0 mg, 5.72 μmol, 37.33% yield, 96.79% purity) was obtained as a white solid.

Procedure for Preparation of BCY12020

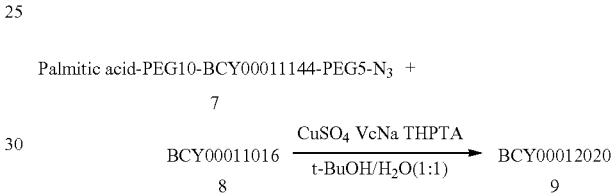

A mixture of compound 7 (50.0 mg, 14.77 μmol, 1.0 eq.), compound 8 (35.0 mg, 15.06 μmol, 1.0 eq.), and THPTA (10.0 mg, 23.02 μmol, 1.5 eq.) was dissolved in t-BuOH/$H_2O$ (1:1, 2 mL, pre-degassed and purged with $N_2$ for 3 times), and then $CuSO_4$ (0.4 M, 38.0 μL, 1.0 eq.) and VcNa (6.5 mg, 32.81 μmol, 2.2 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 16 hr under $N_2$ atmosphere. LC-MS showed one main peak with desired m/z (calculated MW: 5709.68, observed m/z: 1902.80 ($[M/3+H]^+$), 1427.56 ($[M/4+H]^+$)). The reaction mixture was filtered and concentrated under reduced pressure to give a residue. The crude product was purified by prep-HPLC (TFA condition), and BCY12020 (54.8 mg, 9.49 μmol, 64.24% yield, 98.83% purity) was obtained as a white solid.

Example 8: Synthesis of BCY12661

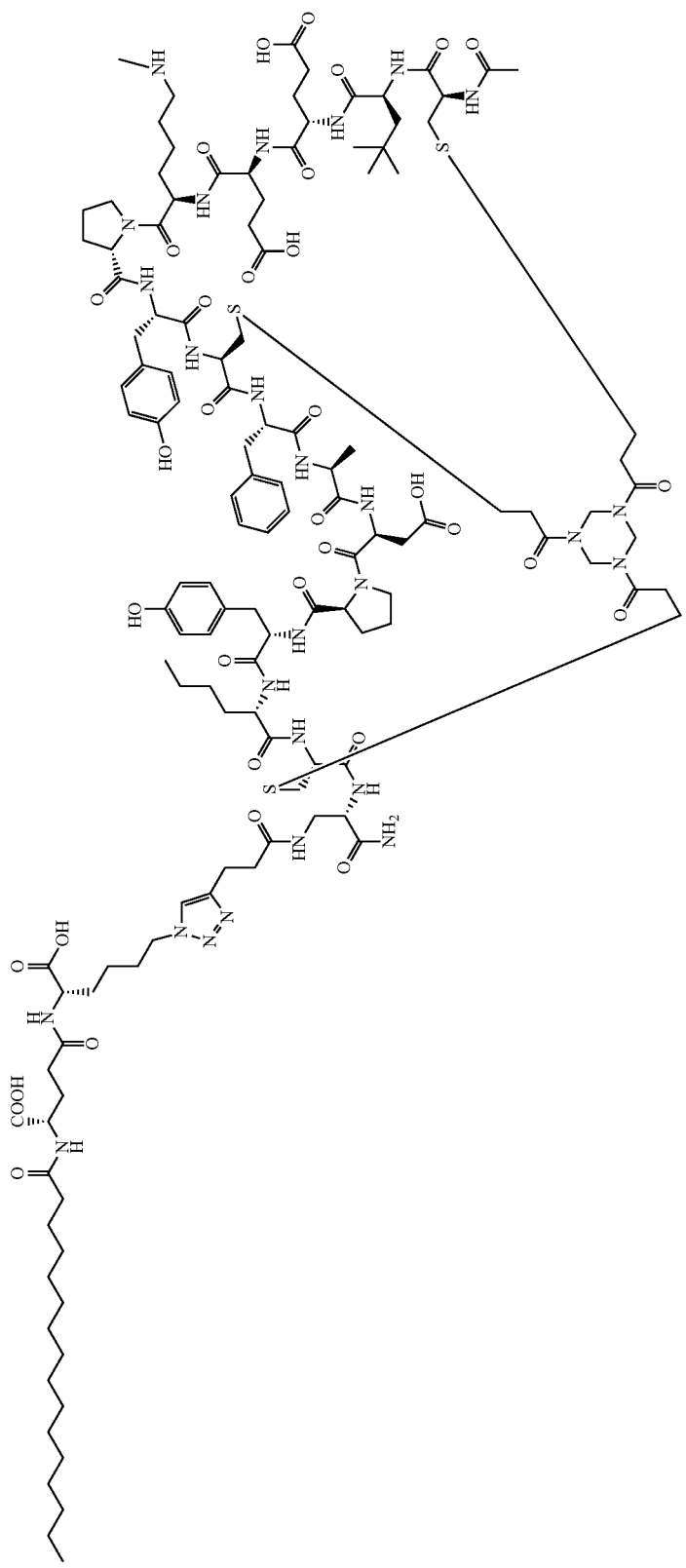

-continued
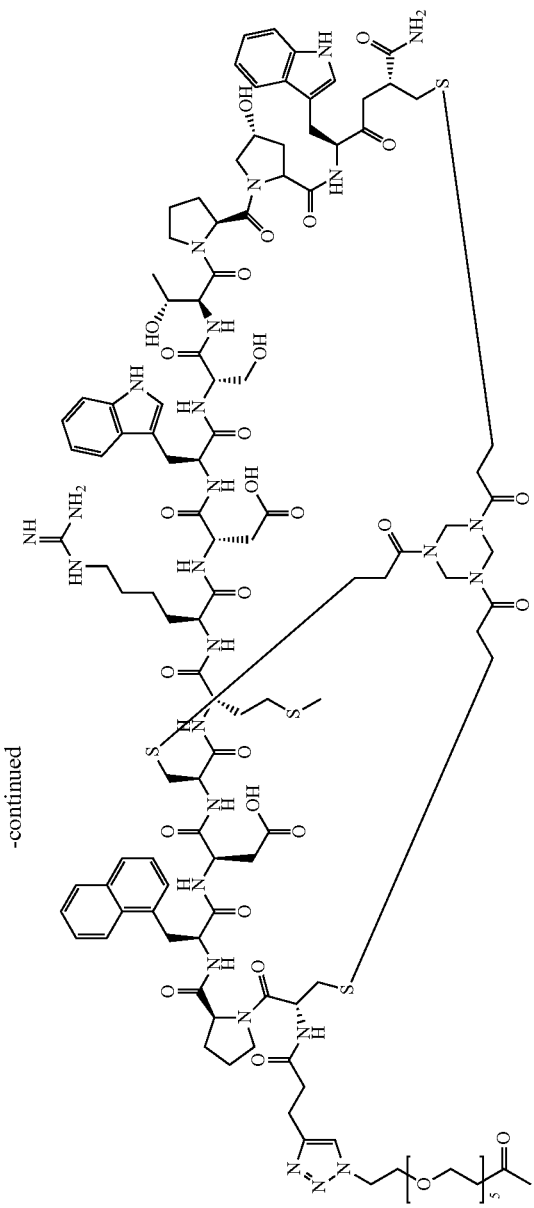

Procedure for Preparation of Compound 2

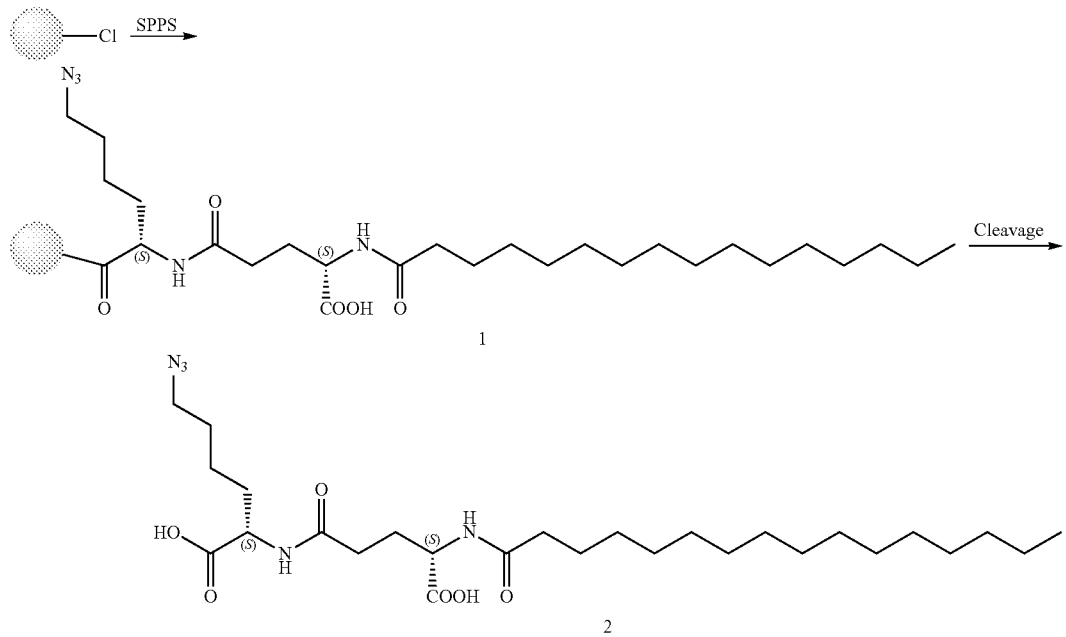

The peptide was synthesized using standard Fmoc chemistry. DCM was added to a reaction vessel containing Chlorotrityl resin (1 mmol, 0.91 g, 1.10 mmol/g) and Fmoc-Lys($N_3$)—OH (1 eq, 395.4 mg, 1 mmol) with $N_2$ bubbling. DIEA (4.0 eq) was added dropwise and mixed for 2 hours. MeOH (2 mL) was then added and mixed for 30 min. The resin was drained and washed with DMF 5 times. Fmoc deprotection was performed by addition of 20% piperidine/DMF and mixing for 30 min. The resin was drained and washed with DMF 5 times. For chain elongation, Fmoc-amino acid solution was added and mixed for 30 sec first, then add activation buffer (containing HBTU and DIEA in DMF) was added and stirred for 1 hr with continuous $N_2$ bubbling. Deprotection and coupling was repeated until the peptide was complete.

| # | Materials | Coupling reagents |
|---|---|---|
| 1 | Fmoc-Lys(N3) -OH (1 eq) | DIEA(4.0 eq) |
| 2 | Fmoc-γGlu(OtBu)-OH (3 eq) | HBTU(2.85 eq) and DIEA(6.0 eq) |
| 3 | Palmitic acid (3 eq) | HBTU(2.85 eq) and DIEA(6.0 eq) |

After last amino acid coupling, the resin was washed with MeOH 3 times, and then dried under vacuum. 10 ml of cleavage cocktail (95% TFA/2.5% TIS/2.5% $H_2O$) was added to the flask containing the side-chain protected peptide at room temperature and this was stirred for 1 hour. The resin was filtered and the filtrate concentrated to remove the solvent. The crude peptide was lyophilized to give the final product Compound 2 (palmitic acid azide) (200 mg, 97.78% purity, 37.06% yield). Calculated MW: 539.72, observed m/z: 540.4 ([M+H]$^+$).

Procedure for Preparation of BCY12023-palmitic acid azide

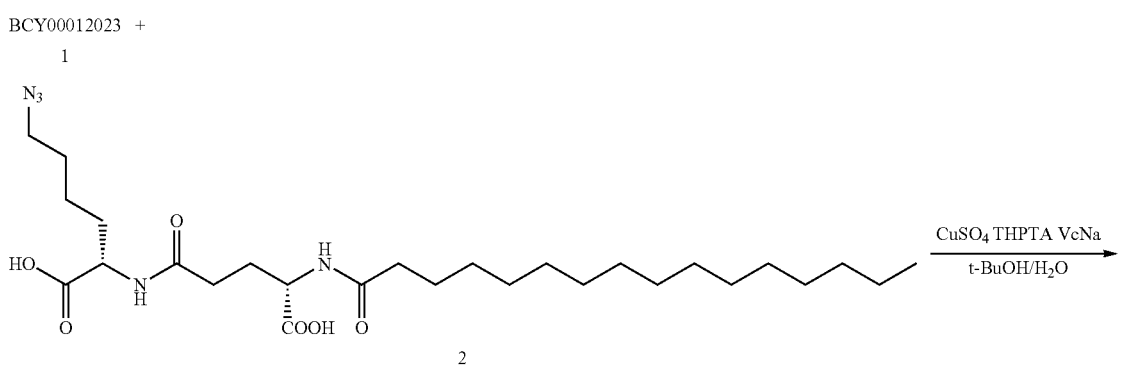

-continued

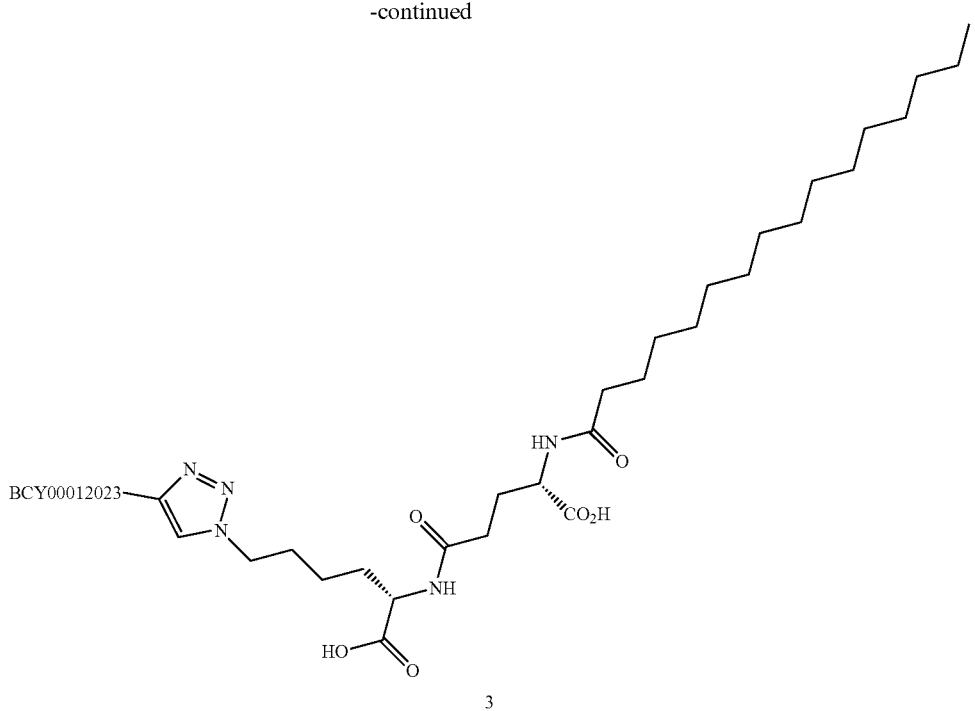

3

A mixture of compound 1 (40.0 mg, 17.66 μmol, 1.0 eq.), compound 2 (9.5 mg, 17.66 μmol, 1.0 eq.), and THPTA (8.0 mg, 17.66 μmol, 1.0 eq.) was dissolved in t-BuOH/H$_2$O (1:1, 1 mL, pre-degassed and purged with N$_2$ for 3 times), and then CuSO$_4$ (0.4 M, 45.0 μL, 1.0 eq.) and VcNa (8.0 mg, 35.33 μmol, 2.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 4 hr under N$_2$ atmosphere. LC-MS showed compound 1 was consumed completely and one main peak with desired m/z (calculated MW: 2804.30, observed m/z: 1402.8 ([M/2+1-1]$^+$), 935.9 ([M/3+H]$^+$)) was detected. The reaction mixture was filtered and concentrated under reduced pressure to give a residue. The crude product was purified by prep-HPLC (TFA condition), and BCY12023-palmitic acid azide (35.0 mg, 12.11 μmol, 68.54% yield, 97.00% purity) was obtained as a white solid.

Procedure for Preparation of BCY12023-Palmitic Acid-PEG5-N$_3$

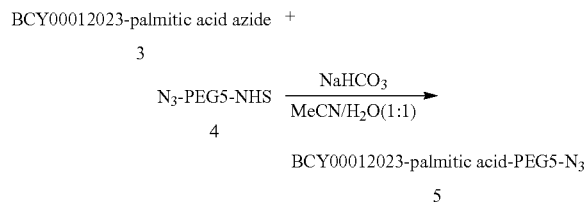

A mixture of compound 3 (35.0 mg, 12.48 μmol, 1.0 eq.), compound 4 (5.4 mg, 12.48 μmol, 1.0 eq.) was dissolved in MeCN/H$_2$O (1:1, 1 mL), and then the pH of this solution was adjusted to 8 by dropwise addition of NaHCO$_3$ (0.1 M). The reaction mixture was stirred at 30° C. for 2 hr. LC-MS showed compound 3 was consumed completely and one main peak with desired m/z (MW: 3121.63, observed m/z: 1561.2 ([(M/2+H$^+$])) was detected. The reaction mixture was concentrated under reduced pressure to remove solvent and produced a residue. The residue was then purified by prep-HPLC (neutral condition). BCY12023-palmitic acid-PEG5-N$_3$ (11.4 mg, 3.46 μmol, 27.71% yield, 94.70% purity) was obtained as a white solid.

Procedure for Preparation of BCY12661

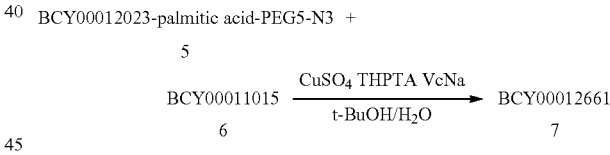

A mixture of compound 5 (11.4 mg, 3.65 μmol, 1.0 eq.), compound 6 (8.3 mg, 3.65 μmol, 1.0 eq.), and THPTA (1.6 mg, 3.65 μmol, 1.0 eq.) was dissolved in t-BuOH/H$_2$O (1:1, 1 mL, pre-degassed and purged with N$_2$ 3 times), and then CuSO$_4$ (0.4 M, 10.0 μL, 1.1 eq.) and VcNa (1.5 mg, 7.30 μmol, 2.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 4 hr under N$_2$ atmosphere. LC-MS showed compound 3 was consumed completely and one main peak with desired m/z (calculated MW: 5374.21, observed m/z: 1344.5 ([M/4+H]$^+$)) was detected. The reaction mixture was filtered and concentrated under reduced pressure to give a residue. The crude product was purified by prep-HPLC (TFA condition), and BCY12661 (9.8 mg, 19.63 μmol, 48.73% yield, 97.60% purity) was obtained as a white solid.

Example 9: Synthesis of BCY12969

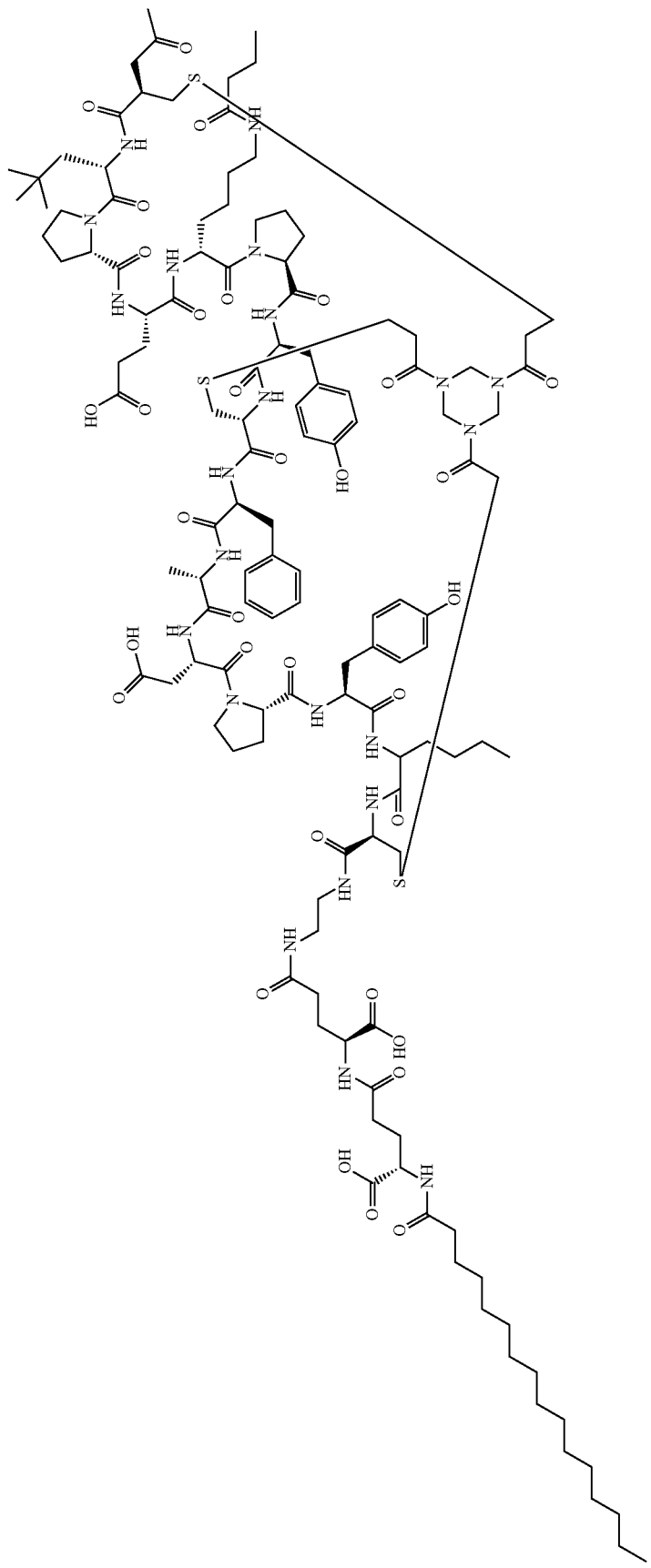

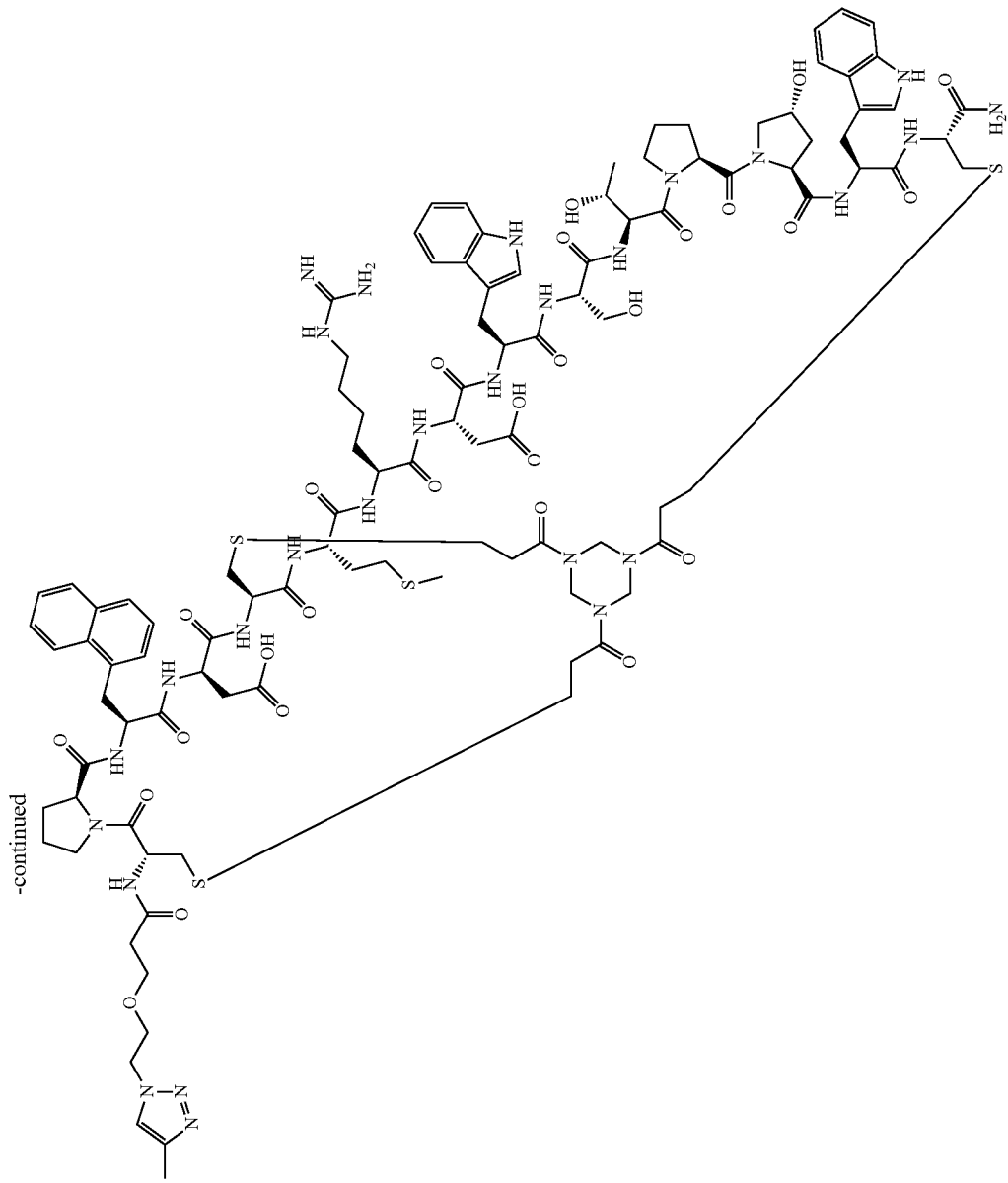

General Procedure for Preparation of Compound 1

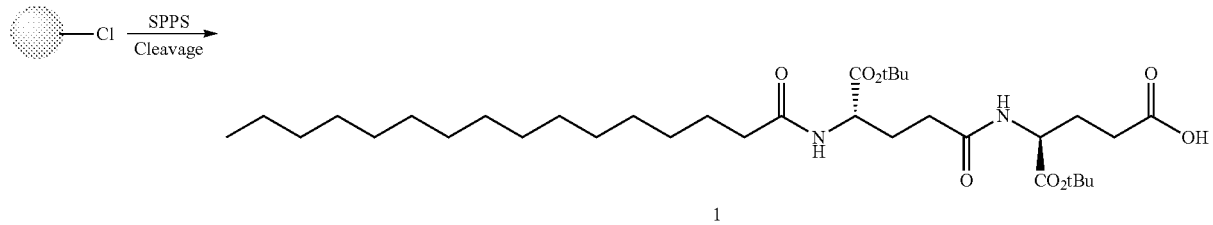

The peptide was synthesized using standard Fmoc chemistry. DCM was added to a reaction vessel containing chlorotrityl resin (1 mmol, 0.91 g, 1.1 mmol/g) and Fmoc-γGlu(OtBu)-OH (0.425 mg, 1 mmol, 1 eq) and the mixture stirred with $N_2$ bubbling. DIEA (4.0 eq) was added dropwise and the mixture was agitated for 2 hours. MeOH (4.6 mL) was then added and mixed for 30 min. The resin was drained and washed with DMF 5 times. 20% piperidine/DMF was added to the resin and mixed for 30 minutes. The resin was drained and washed with DMF 5 times. Fmoc-amino acid solution was added to the resin and mixed for 30 seconds, then activating agent and DIPEA was added and $N_2$ bubbled through the mixture for 1 hour. Deprotection and coupling steps were repeated with the following reagents:

Note:

| # | Materials | Coupling reagents |
|---|-----------|-------------------|
| 1 | Fmoc-Glu-OtBu (1 eq) | DIEA(4.0 eq) |
| 2 | Fmoc-Glu-OtBu (3 eq) | HBTU(2.85 eq) and DIEA(6.0 eq) |
| 3 | Palmitic acid (3 eq) | HBTU(2.85 eq) and DIEA(6.0 eq) |

After coupling of Palmitic acid, the resin was washed 3 times with MeOH and then dried under vacuum. The peptide was cleaved from the resin by addition of 20% HFIP/80% DCM at room temperature and the mixture stirred for 1 hour. This procedure was repeated once more then the resin was filtered and the filtrate concentrated to remove the solvent. The crude peptide was lyophilized to give the final product (280 mg, 84.80% purity, 44.67% yield). Calculated MW: 626.8, observed m/z: 627.4 ([M+H]$^+$)

General Procedure for Preparation of Compound 3

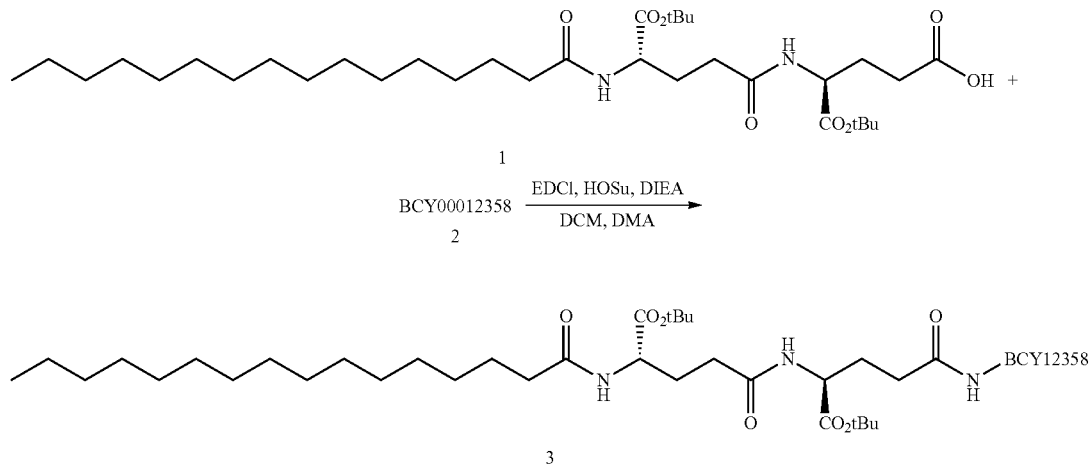

To a solution of compound 2 (15.8 mg, 25.1 μmol, 1.1 eq) in DMF (0.5 mL) was added EDCl (4.4 mg, 22.8 μmol, 1.0 eq) and stirred for 10 min. Then HOSu (2.9 mg, 25.1 μmol, 1.1 eq) and DIEA (8.8 mg, 68.5 μmol, 11.9 μL, 3 eq) were added to the mixture. The mixture was stirred for 16 hr at 25° C. Then BCY12358 (50.0 mg, 22.8 μmol, 1.0 eq) in DMF (0.5 mL) was added to the mixture and this was stirred at 25° C. for another 4 hr. LC-MS showed BCY12358 was consumed completely and one main peak with desired m/z (Calculated MW: 2798.42, observed m/z: 1399.6 [M/2+H]$^+$) was detected. The reaction mixture was purified by prep-HPLC (A: 0.075% TFA in $H_2O$, B: ACN) to give compound 3 (21.9 mg, 7.83 μmol, 34.3% yield) as a white solid.

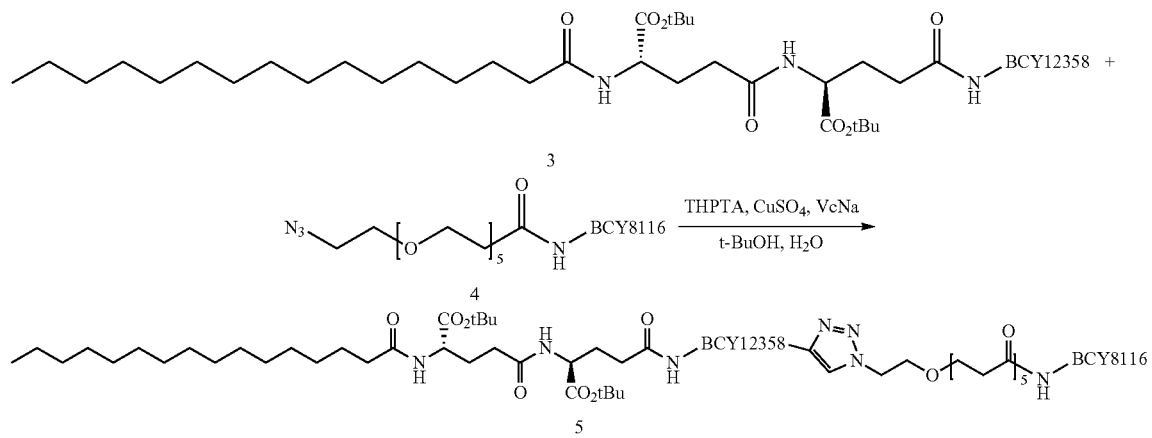

A mixture of compound 4 (20.0 mg, 8.03 μmol, 1.0 eq), compound 3 (22.5 mg, 8.03 μmol, 1.0 eq) and THPTA (4.0 mg, 9.21 μmol, 1.15 eq) in t-BuOH (0.5 mL) and H$_2$O (0.5 mL) was degassed and purged with N$_2$ 3 times, and then CuSO$_4$ (0.4 M, 20.1 μL, 1.0 eq), VcNa (0.4 M, 40.2 μL, 2.0 eq) and NH$_4$HCO$_3$ (0.2 M, 80.4 μL, 2.0 eq) were added to the mixture. The mixture was stirred at 30° C. for 2 hr under N$_2$ atmosphere. LC-MS showed compound 4 was consumed completely and one main peak with desired m/z (Calculated MW: 5288.25, observed m/z: 1322.3 [M/4+H]$^+$, 1763.8 [M/3+1-1]$^+$) was detected. EDTA (0.5 M, 20.0 μL) was added to the reaction mixture. The reaction mixture was concentrated under reduced pressure to give a crude product compound 5 (42.0 mg, crude) as gray solid and used into the next step without further purification.

General Procedure for Preparation of BCY12969

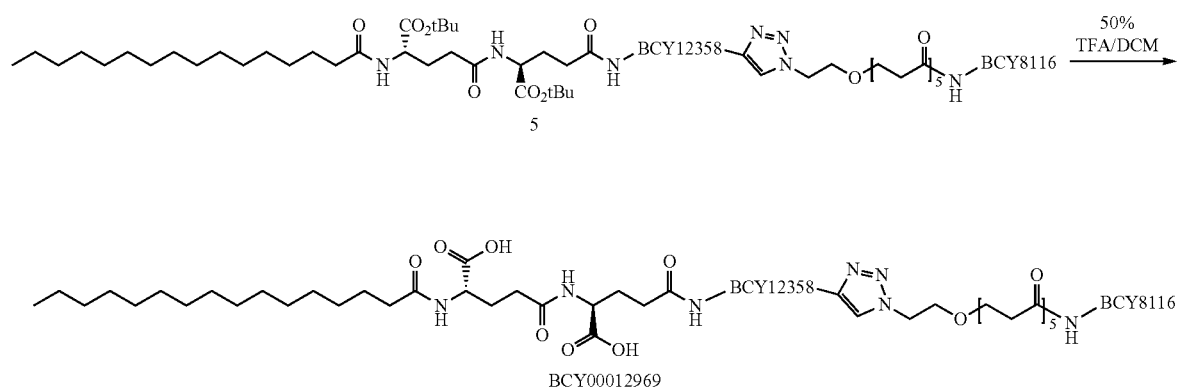

To a solution of compound 5 (42.0 mg, 8.22 μmol, 1.0 eq) in DCM (0.25 mL) was added TFA (3.37 μmol, 0.25 mL, 458.6 eq) dropwise. The mixture was stirred at 30° C. for 1 hr. LC-MS showed compound 5 was consumed completely and one main peak with desired m/z (Calculated MW: 5176.04, observed m/z: 1035.7 [M/5+H]$^+$, 1294.9 [M/4+H]$^+$, 1726.8 [M/3+1-1]$^+$) was detected. The reaction mixture was concentrated under reduced pressure to give residue. The residue was purified by prep-HPLC (A: 0.075% TFA in H$_2$O, B: ACN) to give BCY12969 (2.6 mg, 0.48 μmol, 5.85% yield, 92.4% purity) as a white solid.

Example 10: Synthesis of BCY13035

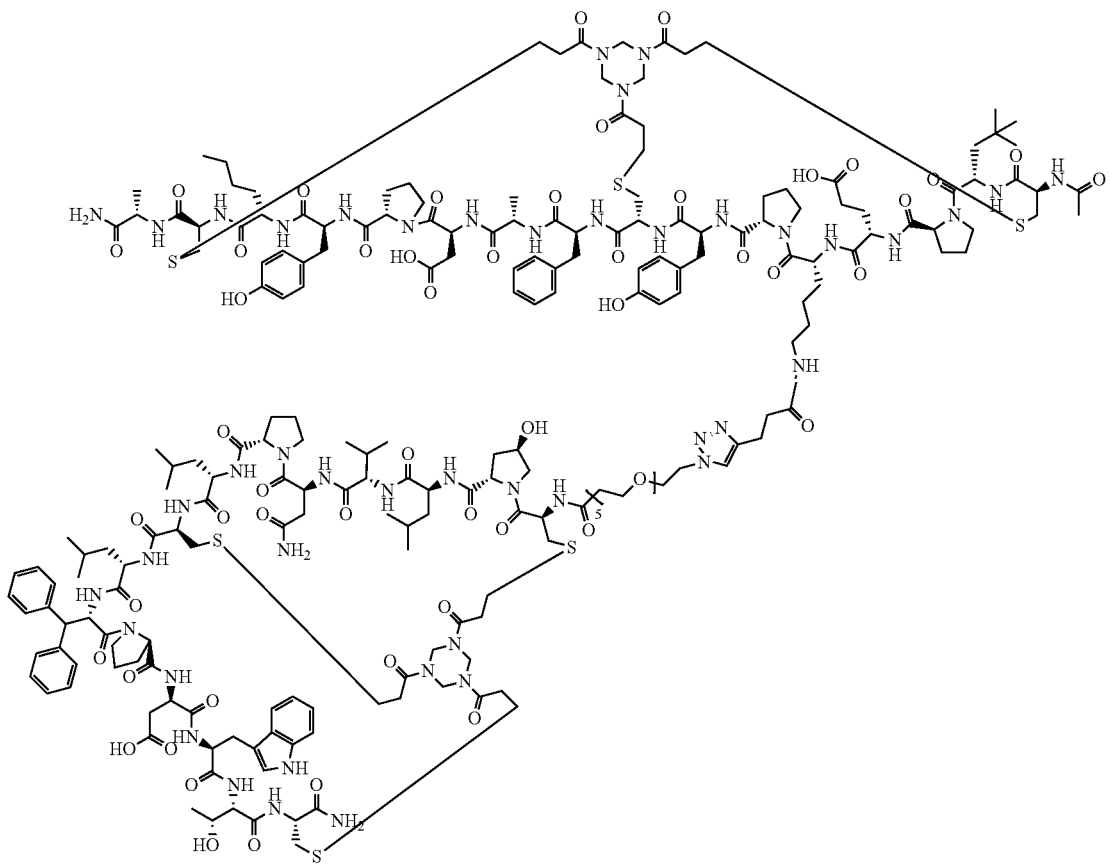

Procedure for Preparation of BCY12860-PEG5-N₃

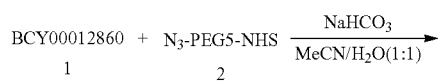

Procedure for Preparation of BCY13035

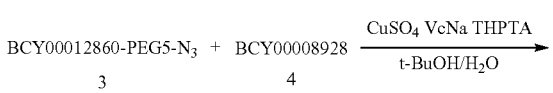

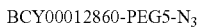

A mixture of BCY12860 (40.0 mg, 19.40 μmol, 1.0 eq.), compound 2 (10.0 mg, 21.34 μmol, 1.1 eq.) was dissolved in MeCN/H₂O (1:1, 1 mL), and then the pH of this solution was adjusted to 8 by dropwise addition of NaHCO₃ (0.1 M). The reaction mixture was stirred at 25° C. for 1 hr. LC-MS showed a peak with desired m/z. The reaction mixture was concentrated under reduced pressure to remove solvent and produced a residue. The residue was then purified by prep-HPLC (neutral condition). BCY12860-PEG5-N₃ (39.7 mg, 15.02 μmol, 77.41% yield, 90.0% purity) was obtained as a white solid. MW: 2378.78, observed m/z: 1190.1 ([(M/2+H⁺]), 793.5 ([(M/3+H⁺]).

A mixture of compound 3 (39.7 mg, 16.69 μmol, 1.0 eq.), BCY8928 (41.0 mg, 18.36 μmol, 1.1 eq.), and THPTA (0.4 M, 55 μL, 1.3 eq.) was dissolved in t-BuOH/H₂O (1:1, 1 mL, pre-degassed and purged with N₂ 3 times), and then CuSO₄ (0.4 M, 55 μL, 1.3 eq.) and VcNa (0.4 M, 109 μL, 2.6 eq.) were added under N₂. The pH of this solution was adjusted to 8 by dropwise addition of 0.2 M NH₄HCO₃ (in 1:1 t-BuOH/H₂O), and the solution turned to light yellow. The reaction mixture was stirred at 40° C. for 2 hr under N₂ atmosphere. LC-MS showed compound 3 was consumed completely and one main peak with desired m/z was detected. The reaction mixture was filtered and concentrated under reduced pressure to give a residue. The crude product was purified by prep-HPLC (TFA condition), and BCY13035 (42.0 mg, 8.85 μmol, 53.04% yield, 96.41% purity) was obtained as a white solid. Calculated MW: 4596.37, observed m/z: 1532.9 ([M/3+H]⁺), 1149.9 ([M/4+H]⁺).

Example 11: Synthesis of BCY13040

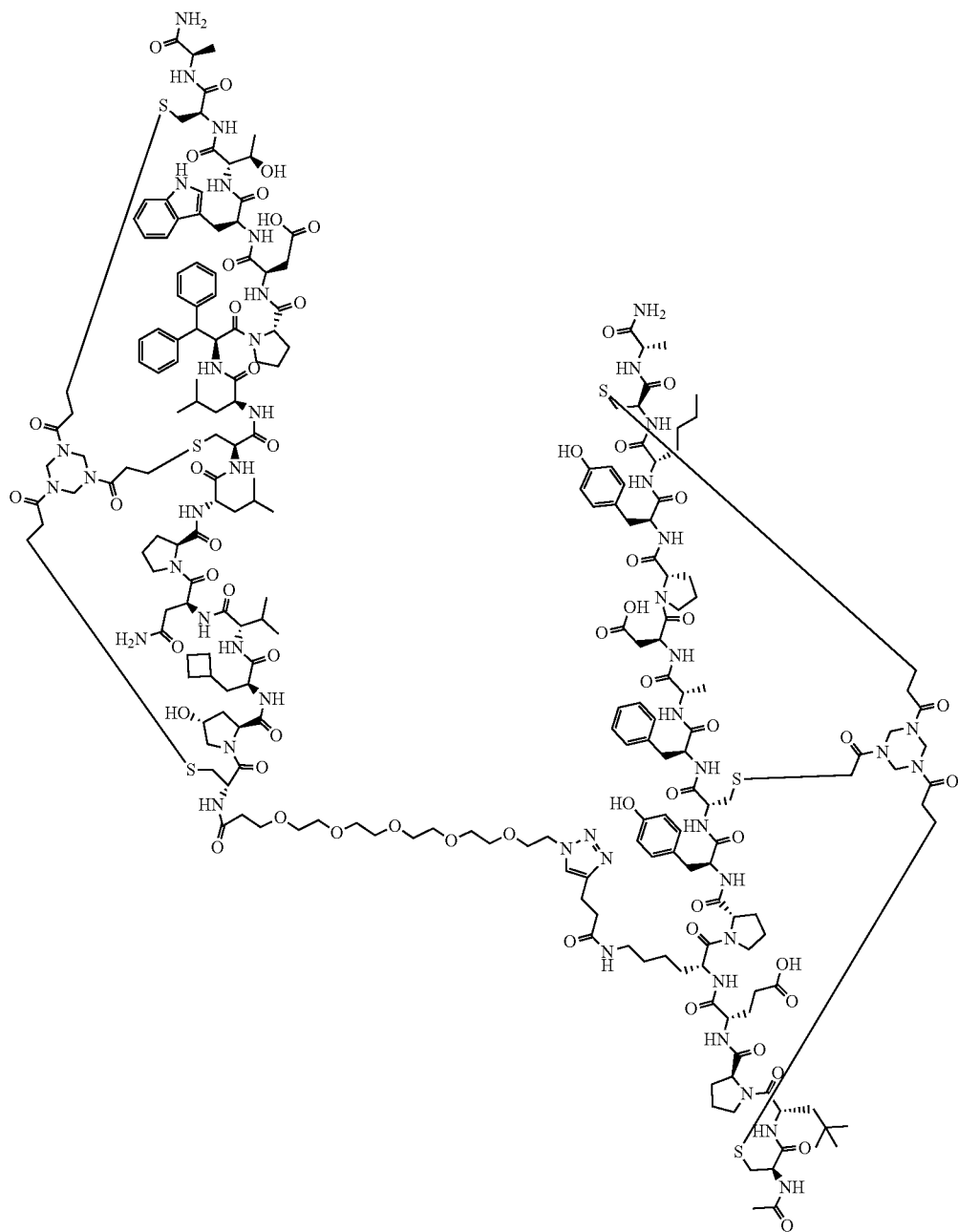

Procedure for Preparation of BCY12865-PEG5-N$_3$

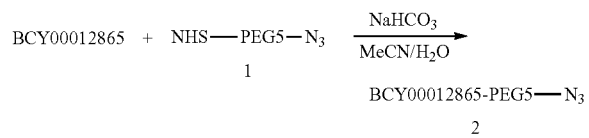

BCY12865 (30.0 mg, 13.99 μmol, 1.0 eq) and compound 1 (6.1 mg, 14.11 μmol, 1.01 eq), were dissolved in 1 mL of MeCN/H$_2$O (1:1), and then 1 M NaHCO$_3$ was added to adjust pH to 8. The mixture was stirred at 25° C. for 2 hr. LC-MS showed BCY12865 was consumed completely and one main peak with desired m/z was detected. The reaction mixture was purified by prep-HPLC (TFA condition) and compound 2 (15.6 mg, 6.32 μmol, 45.19% yield, 99.76% purity) was obtained as a white solid. Calculated MW: 2461.87, observed m/z: 1231.5 ([M/2+H]$^+$) and 821.3 ([M/3+H]$^+$).

Procedure for Preparation of BCY13040

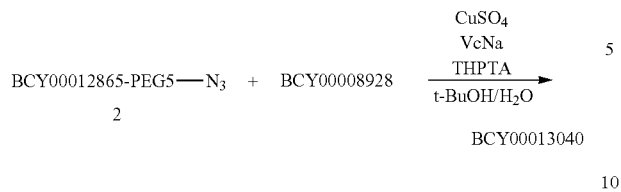

Compound 2 (15.6 mg, 6.34 μmol, 1.0 eq) and BCY8928 (14.5 mg, 6.54 μmol, 1.03 eq) were first dissolved in 2 mL of t-BuOH/$H_2O$ (1:1), and then $CuSO_4$ (0.4 M, 16 μL, 1.01 eq), VcNa (3.0 mg, 15.14 μmol, 2.39 eq) and THPTA (3 mg, 6.90 μmol, 1.09 eq) were added. Finally, 1 M $NH_4HCO_3$ was added to adjust the pH to 8. All solvents were degassed and purged with $N_2$ 3 times. The reaction mixture was stirred at 40° C. for 16 hr under $N_2$ atmosphere. LC-MS showed Compound 2 was consumed completely and one main peak with desired m/z was detected. The reaction mixture was purified by prep-HPLC (TFA condition) and BCY13040 (15.8 mg, 3.31 μmol, 52.27% yield, 98.1% purity) was obtained as a white solid. Calculated MW: 4679.45, observed m/z: 1560.8 ($[M/3+H]^+$), 1170.9 ($[M/4+H]^+$), 936.6 ($[M/5+H]^+$).

Example 12: Synthesis of BCY13253

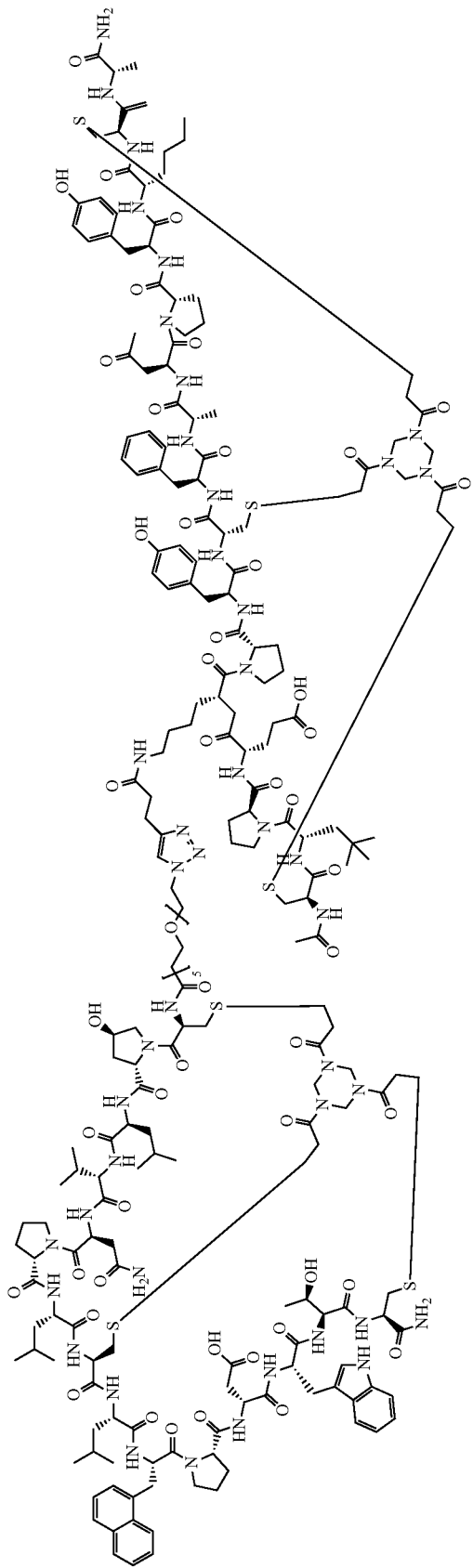

Procedure for Preparation of BCY13119-PEG5-N₃

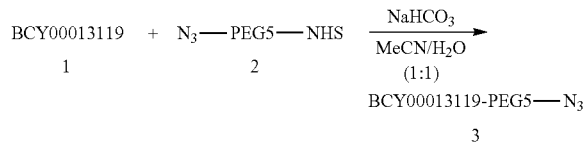

A mixture of BCY13119 (35.0 mg, 17.20 µmol, 1.0 eq.), compound 2 (7.8 mg, 18.06 µmol, 1.05 eq.) was dissolved in MeCN/H₂O (1:1, 1 mL), and then the pH of this solution was adjusted to 8 by dropwise addition of NaHCO₃ (0.1 M). The reaction mixture was stirred at 25° C. for 1 hr. LC-MS showed one main peak with desired m/z (MW: 2352.74, observed m/z: 1177.4 ([(M/2+H⁺])) was detected. The reaction mixture was concentrated under reduced pressure to remove solvent and produced a residue. The residue was then purified by prep-HPLC (neutral condition). BCY13119-PEG5-N₃ (25.7 mg, 9.97 µmol, 58.0% yield, 91.3% purity) was obtained as a white solid.

Procedure for Preparation of BCY13253

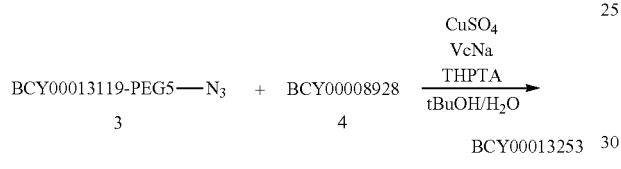

A mixture of compound 3 (25.7 mg, 10.92 µmol, 1.0 eq.), compound 2 (26.6 mg, 12.02 µmol, 1.1 eq.), and THPTA (5.7 mg, 13.11 µmol, 1.2 eq.) was dissolved in t-BuOH/H₂O (1:1, 1 mL, pre-degassed and purged with N₂ 3 times), and then CuSO₄ (0.4 M, 33.0 µL, 1.2 eq.) and VcNa (5.2 mg, 26.21 µmol, 2.4 eq.) were added under N₂. The pH of this solution was adjusted to 8 by dropwise addition of 0.2 M NH₄HCO₃ (in 1:1 t-BuOH/H₂O), and the solution turned to light yellow. The reaction mixture was stirred at 25° C. for 2 hr under N₂ atmosphere. LC-MS showed compound 3 was consumed completely and one main peak with desired m/z (calculated MW: 4570.32, observed m/z: 1143.4 ([M/4+1-1]⁺), 914.9 ([M/5+H]⁺)) was detected. The reaction mixture was filtered and concentrated under reduced pressure to give a residue. The crude product was purified by prep-HPLC (TFA condition), and BCY13253 (17.5 mg, 3.67 µmol, 33.58% yield, 95.8% purity) was obtained as a white solid.

Example 13: Synthesis of BCY13254

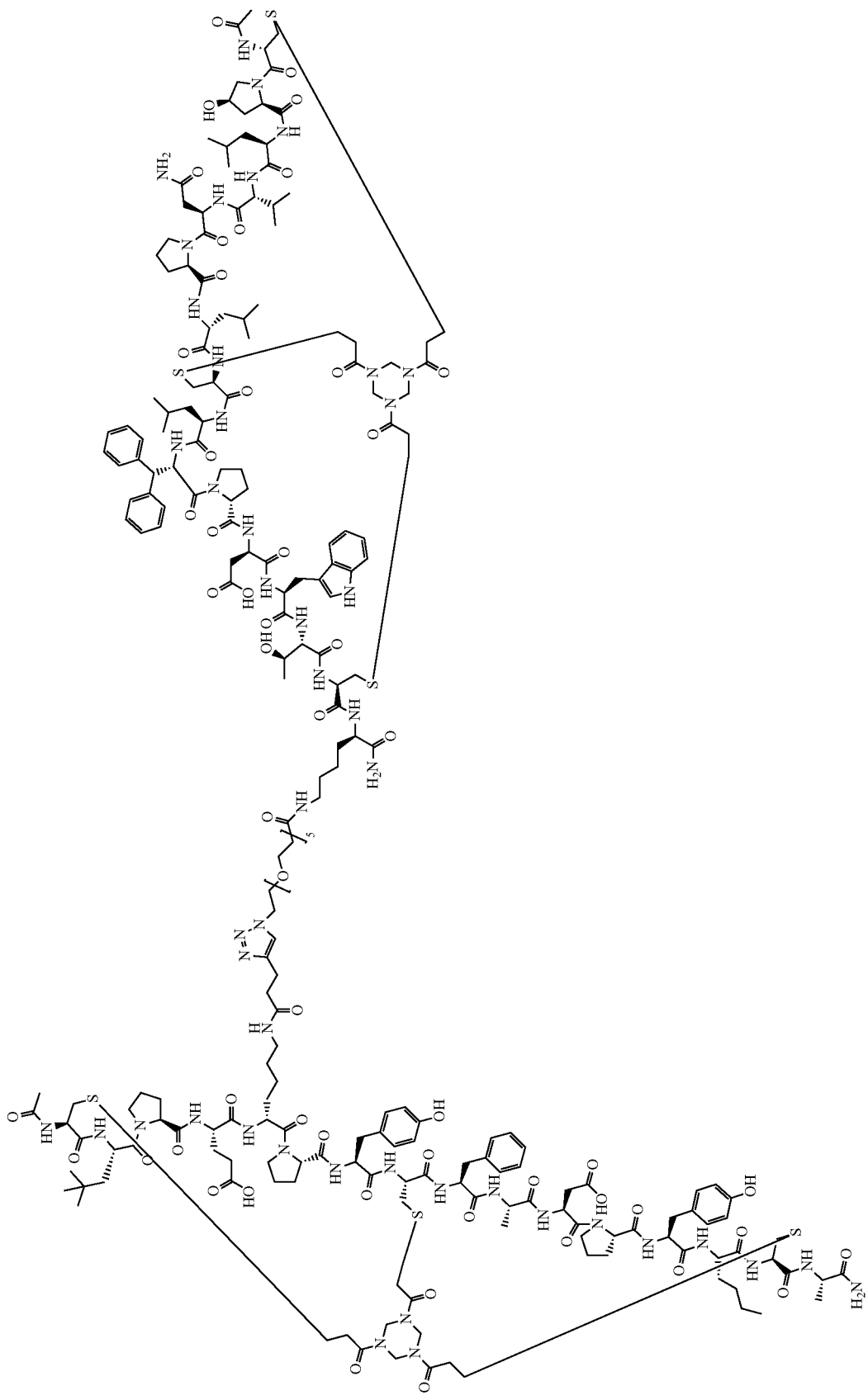

Procedure for Preparation of BCY13120-PEG5-N₃

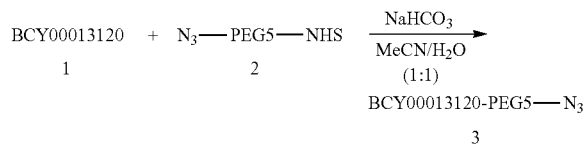

A mixture of BCY13120 (40.0 mg, 17.92 µmol, 1.0 eq.), compound 2 (8.5 mg, 19.72 µmol, 1.1 eq.) was dissolved in MeCN/H₂O (1:1, 1 mL), and then the pH of this solution was adjusted to 8 by dropwise addition of NaHCO₃ (0.1 M). The reaction mixture was stirred at 25° C. for 1 hr. LC-MS showed BCY13120 was consumed completely and one main peak with desired m/z (MW: 2548.99, observed m/z: 1275.3 ([(M/2+H⁺])) was detected. The reaction mixture was concentrated under reduced pressure to remove solvent and produced a residue. The residue was then purified by prep-HPLC (neutral condition). BCY13120-PEG5-N₃ (27.3 mg, 10.46 µmol, 58.38% yield, 97.7% purity) was obtained as a white solid.

Procedure for Preparation of BCY13254

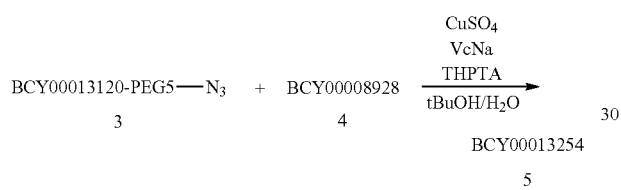

A mixture of compound 3 (27.3 mg, 10.71 µmol, 1.0 eq.), compound 2 (26.1 mg, 11.78 µmol, 1.1 eq.), and THPTA (5.6 mg, 12.85 µmol, 1.2 eq.) was dissolved in t-BuOH/H₂O (1:1, 1 mL, pre-degassed and purged with N₂ 3 times). CuSO₄ (0.4 M, 33.0 µL, 1.2 eq.) and VcNa (5.2 mg, 26.24 µmol, 2.4 eq.) were added under N₂. The pH of this solution was adjusted to 8 by dropwise addition of 0.2 M NH₄HCO₃ (in 1:1 t-BuOH/H₂O), and the solution turned to light yellow. The reaction mixture was stirred at 25° C. for 2 hr under N₂ atmosphere. LC-MS showed compound 3 was consumed completely and one main peak with desired m/z (calculated MW: 4766.58, observed m/z: 1192.5 ([M/4+H]⁺), 954.1 ([M/5+H]⁺)) was detected. The reaction mixture was filtered and concentrated under reduced pressure to give a residue. The crude product was purified by prep-HPLC (TFA condition), and BCY13254 (36.5 mg, 7.49 µmol, 69.92% yield, 97.8% purity) was obtained as a white solid.

Example 14: Synthesis of BCY13340

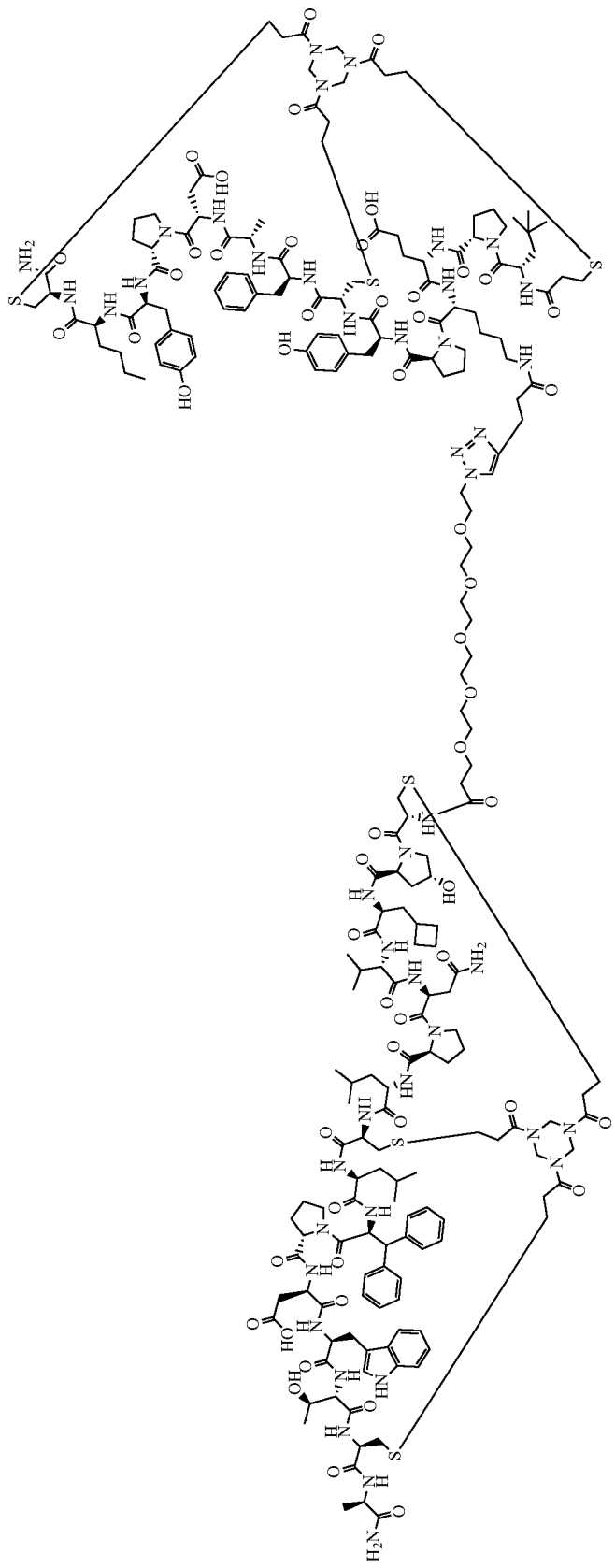

Procedure for Preparation of BCY12865-PEG5-N₃

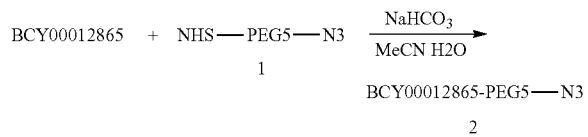

BCY12865 (50 mg, 23.32 μmol, 1.0 eq) and compound 1 (10.5 mg, 24.28 μmol, 1.04 eq), were dissolved in 2 mL of MeCN/H₂O (1:1), 1 M NaHCO₃ was added to adjust pH to 8. And then the mixture was stirred at 25° C. for 2 hr. LC-MS showed BCY12865 was consumed completely and one main peak with desired m/z (calculated MW: 2461.87, observed m/z: 1231.6 ([M/2+H]$^+$) and 821.4 ([M/3+H]$^+$)) was detected. The reaction mixture was purified by prep-HPLC (TFA condition) and compound 2 (31.5 mg, 12.62 μmol, 54.14% yield, 98.66% purity) was obtained as a white solid.

Procedure for Preparation of BCY13340

A mixture of compound 2 (31.5 mg, 12.80 μmol, 1.0 eq.), BCY12353 (27 mg, 12.92 μmol, 1.0 eq), and THPTA (5.7 mg, 13.12 μmol, 1.0 eq) was dissolved in t-BuOH/H₂O (1:1, 2 mL, pre-degassed and purged with N₂ 3 times), and then CuSO₄ (0.4 M, 32 μL, 1.0 eq) and VcNa (5.1 mg, 25.74 μmol, 2.0 eq) were added under N₂. The pH of this solution was adjusted to 8 by dropwise addition of 0.2 M NH₄HCO₃ (in 1:1 t-BuOH/H₂O), and the solution turned to light yellow. The reaction mixture was stirred at 40° C. for 1 hr under N₂ atmosphere. LC-MS showed compound 2 was completely consumed and one main peak with desired m/z (calculated MW: 4551.32, observed m/z: 1517.7 ([M/3+H]$^+$) and 1138.6 ([M/4+H]$^+$)) was detected. The reaction mixture was filtered and concentrated under reduced pressure to give a residue. The crude product was purified by prep-HPLC (TFA condition), and BCY13340 (34.7 mg, 7.62 μmol, 59.59% yield, 89.59% purity) was obtained as a white solid.

Example 15: Synthesis of BCY13342

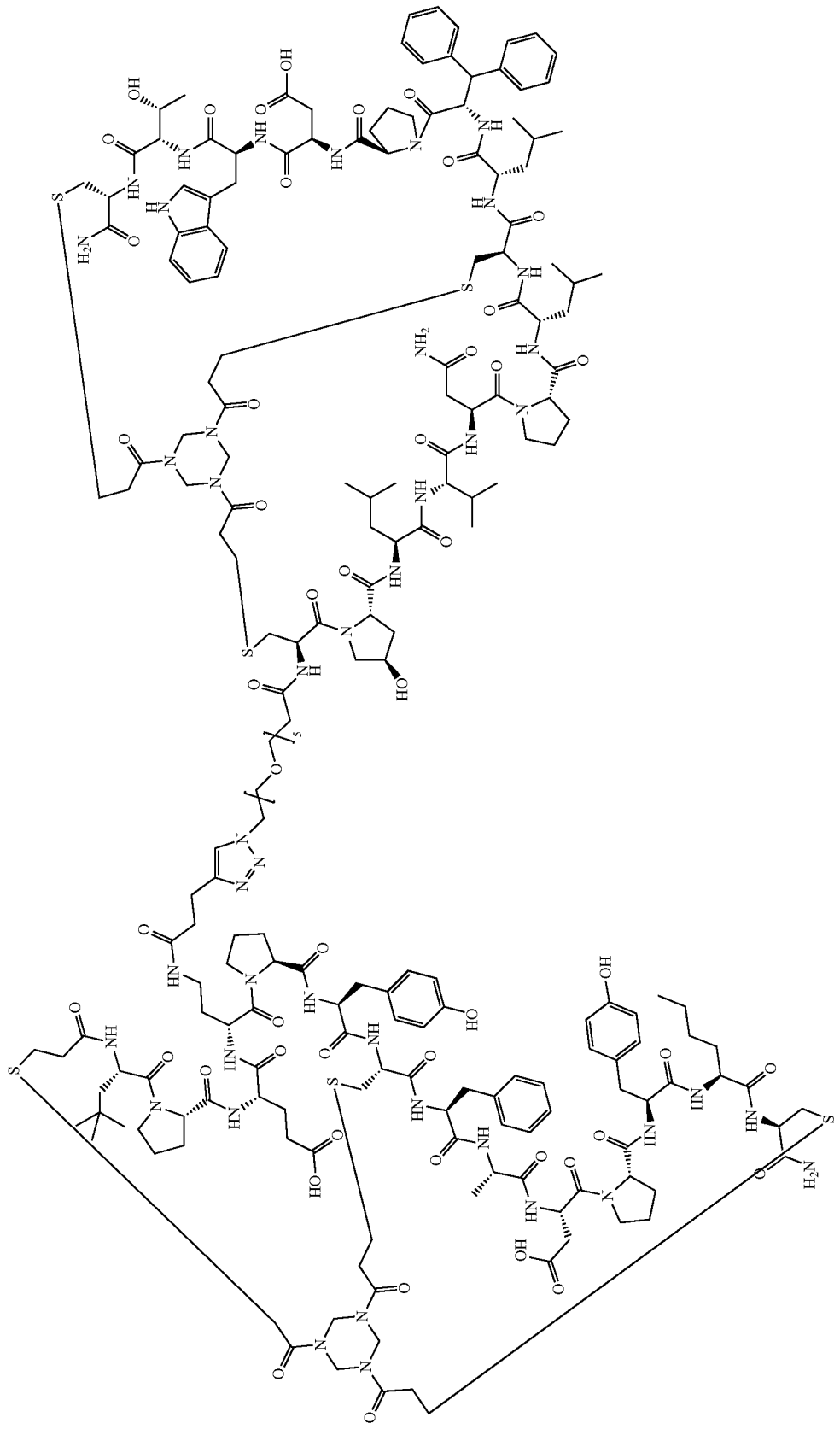

Procedure for Preparation of BCY12860-PEG5-N$_3$

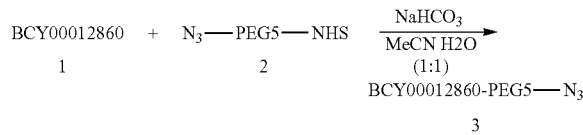

A mixture of BCY12860 (28.0 mg, 13.58 μmol, 1.0 eq.) and compound 2 (6.5 mg, 14.94 μmol, 1.1 eq.) was dissolved in MeCN/H$_2$O (1:1, 1 mL), and then the pH of this solution was adjusted to 8 by dropwise addition of NaHCO$_3$ (0.1 M). The reaction mixture was stirred at 25° C. for 1 hr. LC-MS showed BCY12860 was consumed completely and one main peak with desired m/z (MW: 2378.78, observed m/z: 1190.2 ([(M/2+H$^+$])) was detected. The reaction mixture was concentrated under reduced pressure to remove solvent and produced a residue. The residue was then purified by prep-HPLC (neutral condition). BCY12860-PEG5-N$_3$ (20.7 mg, 8.41 μmol, 61.95% yield, 96.7% purity) was obtained as a white solid.

Procedure for Preparation of BCY13342

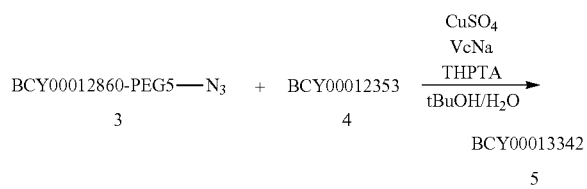

A mixture of compound 3 (20.7 mg, 8.70 μmol, 1.0 eq.), compound 4 (19.0 mg, 9.14 μmol, 1.05 eq.), and THPTA (5.0 mg, 11.31 μmol, 1.3 eq.) was dissolved in t-BuOH/H$_2$O (1:1, 1 mL, pre-degassed and purged with N$_2$ for 3 times), and then CuSO$_4$ (0.4 M, 28.3 μL, 1.3 eq.) and VcNa (4.5 mg, 22.62 μmol, 2.6 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25° C. for 2 hr under N$_2$ atmosphere. LC-MS showed compound 3 was consumed completely and one main peak with desired m/z (calculated MW: 4468.24, observed m/z: 1118.6 ([M/4+H]$^+$)) was detected. The reaction mixture was filtered and concentrated under reduced pressure to give a residue. The crude product was purified by prep-HPLC (TFA condition), and BCY13342 (21.7 mg, 4.60 μmol, 52.85% yield, 94.7% purity) was obtained as a white solid.

Analytical Data

The following heterotandem bicyclic peptide complexes of the invention were analysed using mass spectrometry and HPLC. HPLC setup was as follows:

Mobile Phase: A: 0.1% TFA in H$_2$O B: 0.1% TFA in ACN

Flow: 1.0 ml/min

Column: Gemini-NX C18 5 um 110 A 150*4.6 mm

Instrument: Agilent 1200 HPLC-BE(1-614)

Gradients used are described in the table below:

| Analytical Method | Gradient Description |
|---|---|
| A | 25-55% B over 20 minutes |
| B | 40-70% B over 20 minutes |
| C | 45-75% B over 20 minutes |
| D | 30-60% B over 20 minutes |
| E | 45-75% B over 20 minutes |
| F | 50-80% B over 20 min 50° C. |
| G | 35-65% B over 20 minutes |
| H | 20-50% B over 20 minutes | and the data was generated as follows:

| Complex ID | Analytical Data - Mass Spectrometry | HPLC Retention Time (min) | Analytical Method |
|---|---|---|---|
| BCY12229 | calculated MW: 5125.93, observed m/z: 1281.50 ([M/4 + H]$^+$ | 12.039 | A |
| BCY12230 | calculated MW: 5225.06, observed m/z: 1306.62([M/4 + H]$^+$), 1045.0([M/5 + H]$^+$) | 12.085 | A |
| BCY12231 | calculated MW: 5159.01, observed m/z: 1720.76 ([M/3 + H]$^+$), 1291.72 ([M/4 + H]$^+$) | 10.359 | A |
| BCY12232 | calculated MW: 5168.02, observed m/z: 1722.4([M/3 + H]$^+$), 1291.4 ([M/4 + H]$^+$) | 12.121 | A |
| BCY12242 | calculated MW: 5159.00, observed m/z: 1719.17([M/3 + H]$^+$), 1289.84([M/4 + H]$^+$) | 13.173 | A |
| BCY12375 | calculated MW: 6064.08, observed m/z: 1516.4([M/4 + H]$^+$), 1212.8([M/5 + H]$^+$) | 10.493 | B |
| BCY12663 | calculated MW: 5383.22, observed m/z: 1795.0([M/3 + H]$^+$), 1346.7 ([M/4 + H]$^+$) | 10.346 | A |
| BCY12796 | calculated MW: 5360.18, observed m/z: 1787.7([M/3 + H]$^+$), 1341.0([M/4 + H]$^+$) | 11.529 | A |
| BCY12021 | calculated MW: 6102.17, observedm/z: 1525.17([M/4 + H]+), 1221.3([M/5 + H]+) | 6.822 | C |
| BCY12233 | calculated MW: 4935.71, observed m/z: 1234.16 ([M/4 + H]$^+$) | 10.834 | A |
| BCY12234 | calculated MW: 5105.92, observed m/z: 1276.87([M/4 + H]$^+$), 1021.80([M/5 + H]$^+$) | 10.58 | A |
| BCY12235 | calculated MW: 4968.78, observed m/z: 1655.4([M/3 + H]$^+$), 1242.83([M/4 + H]$^+$) | 12.165 | A |
| BCY12236 | calculated MW: 4992.76, observed m/z: 1248.4([M/4 + H]$^+$) | 10.023 | A |
| BCY12237 | calculated MW: 4992.76, observed m/z: 1248.70([M/4 + H]$^+$), 998.70([M/5 + H]$^+$) | 10.091 | A |

-continued

| Complex ID | Analytical Data - Mass Spectrometry | HPLC Retention Time (min) | Analytical Method |
|---|---|---|---|
| BCY12711 | calculated MW: 4896.6, observed m/z: 1633.1 ([M/3 + H]$^+$), 1225.2([M/4 + H]$^+$) | 11.23 | A |
| BCY12712 | calculated MW: 4864.63, observed m/z: 1622.6([M/3 + H]$^+$), 1217.6([M/4 + H]$^+$) | 11.006 | A |
| BCY12713 | calculated MW: 4863.65, observed m/z: 1621.8([M/3 + H]$^+$), 1217.0([M/4 + H]$^+$) | 10.851 | A |
| BCY12714 | calculated MW: 4878.67, observed m/z: 1626.9([M/3 + H]$^+$), 1220.5([M/4 + H]$^+$) | 10.824 | A |
| BCY12715 | calculated MW: 4892.70, observed m/z: 1631.6([M/3 + H]$^+$), 1223.7([M/4 + H]$^+$) | 10.859 | A |
| BCY12717 | calculated MW: 4821.61, observed m/z: 1607.8([M/3 + H]$^+$), 1206.0([M/4 + H]$^+$) | 11.37 | A |
| BCY12718 | calculated MW: 4807.58, observed m/z: 1603.5([M/3 + H]$^+$), 1202.9([M/4 + H]$^+$) | 11.527 | A |
| BCY12719 | Calculated MW: 4764.57, observed m/z: 1192.0 [M/4 + H]$^+$, 1589.0 [M/3 + H]$^+$ | 15.353 | H |
| BCY12720 | Calculated MW: 5319.25, observed m/z: 1065.1 [M/5 + H]$^+$, 1331.0 [M/4 + H]$^+$, 1773.9 [M/3 + H]$^+$ | 9.285 | B |
| BCY12961 | Calculated MW: 5105.93, observed m/z: 1022.0 [M/5 + H]+, 1277.5 [M/4 + H]+, 1703.0 [M/3 + H]+ | 10.958 | A |
| BCY12962 | Calculated MW: 4968.79, observed m/z: 994.9 [M/5 + H]$^+$, 1243.3 [M/4 + H]$^+$, 1656.7 [M/3 + H]$^+$ | 12.517 | A |
| BCY12963 | Calculated MW: 4992.76, observed m/z: 1249.0 [M/4 + H]$^+$, 1664.9 [M/3 + H]$^+$) | 10.437 | A |
| BCY12964 | Calculated MW: 4992.78, observed m/z: 999.6 [M/5 + H]$^+$, 1249.3 [M/4 + H]$^+$, 1665.3 [M/3 + H]$^+$ | 10.445 | A |
| BCY12965 | Calculated MW: 4949.75, observed m/z: 990.6 [M/5 + H]$^+$, 1238.1 [M/4 + H]$^+$, 1650.4 [M/3 + H]$^+$ | 11.302 | A |
| BCY12966 | Calculated MW: 4963.78, observed m/z: 993.8 [M/5 + H]$^+$, 1241.7 [M/4 + H]$^+$ | 11.138 | A |
| BCY13029 | calculated MW: 4927.69, observed m/z: 1643.7 ([M/3 + H]$^+$), 1233.1 ([M/4 + H]$^+$) | 11.74 | A |
| BCY13030 | calculated MW: 4866.62, observed m/z: 1622.7 ([M/3 + H]$^+$), 1217.2 ([M/4 + H]$^+$), 974.0 ([M/5 + H]$^+$) | 11.393 | A |
| BCY13031 | calculated MW: 4858.59, observed m/z: 1619.9 ([M/3 + H]$^+$), 1215.1 ([M/4 + H]$^+$) | 10.381 | D |
| BCY13032 | calculated MW: 4929.67, observed m/z: 1643.9 ([M/3 + H]$^+$), 1233.3([M/4 + H]$^+$) | 13.144 | A |
| BCY13033 | calculated MW: 4814.57, observed m/z: 1606.0([M/3 + H]$^+$), 1204.2 ([M/4 + H]$^+$), 963.6 ([M/5 + H]$^+$) | 13.497 | A |
| BCY13034 | calculated MW: 4952.75, observed m/z: 1651.5([M/3 + H]$^+$), 1239.0([M/4 + H]$^+$) | 12.207 | G |
| BCY13035 | calculated MW: 4596.37, observed m/z: 1532.9([M/3 + H]$^+$), 1149.9 ([M/4 + H]$^+$)) | 8.083 | C |
| BCY13036 | calculated MW: 4573.29, observed m/z: 1525.4([M/3 + H]$^+$) and 1143.9([M/4 + H]$^+$) | 12.387 | D |
| BCY13037 | calculated MW: 4947.74, observed m/z: 1650.4([M/3 + H]$^+$), 1238.0 ([M/4 + H]$^+$) | 11.699 | A |
| BCY13038 | calculated MW: 4870.60, observed m/z: 1624.2([M/3 + H]$^+$), 1218.5 ([M/4 + H]$^+$) | 10.747 | D |
| BCY13039 | calculated MW: 4914.67, observed m/z: 1648.5([M/3 + H]$^+$), 1235.9 ([M/4 + H]$^+$) | 10.542 | D |
| BCY13040 | calculated MW: 4679.45, observed m/z: 1560.8 ([M/3 + H]$^+$), 1170.9 ([M/4 + H]$^+$), 936.6 ([M/5 + H]$^+$) | 14.688 | G |
| BCY13041 | calculated MW: 5021.86, observed m/z: 1674.4 ([M/3 + H]$^+$), 1256.1 ([M/4 + H]$^+$), 1005.2 ([M/5 + H]$^+$ | 9.609 | G |
| BCY11616 | calculated MW: 4827.46, observed m/z: 1609.7([M/3 + H]$^+$), 1207.5([M/4 + H]$^+$) | 12.538 | A |
| BCY12238 | calculated MW: 4763.50, observed m/z: 1587.84 ([M/3 + H]$^+$), 1191.37([M/4 + H]$^+$) | 14.249 | A |
| BCY12377 | calculated MW: 4668.32, observed m/z: 1556.1 ([M/3 + H]$^+$), 1167.0 ([M/4 + H]$^+$) | 14.304 | A |
| BCY12379 | calculated MW: 4636.32, observed m/z: 1159.8([M/4 + H]$^+$) | 10.779 | D |
| BCY12572 | calculated MW: 4593.29, observed m/z: 1531.7([M/3 + H]$^+$), 1148.8([M/4 + H]$^+$) | 11.303 | D |

-continued

| Complex ID | Analytical Data - Mass Spectrometry | HPLC Retention Time (min) | Analytical Method |
|---|---|---|---|
| BCY12573 | calculated MW: 4579.27, observed m/z: 1526.8([M/3 + H]+) | 14.454 | A |
| BCY12574 | calculated MW: 4536.24, observed m/z: 1512.9([M/3 + H]+) | 11.959 | D |
| BCY12575 | calculated MW: 5090.92, observed m/z: 1698.3([M/3 + H]+), 1273.9([M/4 + H]+) | 9.868 | C |
| BCY12576 | (calculated MW: 4705.47, observed m/z: 1568.7 ([M/3 + H]+), 1177.3([M/4 + H]+) | 11.383 | D |
| BCY12577 | Calculated MW: 4719.51, observed m/z: 1180.8 [M/4 + H]+, 1574.2 [M/3 + H]+) | 10.953 | D |
| BCY12578 | Calculated MW: 4662.45, observed m/z: 1165.9 [M/4 + H]+, 1554.8 [M/3 + H]+ | 11.906 | D |
| BCY12579 | calculated MW: 4784.57, observed m/z: 1595.7([M/3 + H]+), 1197.0([M/4 + H]+) | 12.811 | A |
| BCY12580 | calculated MW: 4776.56, observed m/z: 1592.2 ([M/3 + H]+) | 14.107 | A |
| BCY12581 | calculated MW: 4721.43, observed m/z: 1574.2 ([M/3 + H]+) and 1181.1 ([M/4 + H]+) | 10.776 | D |
| BCY12582 | calculated MW: 4663.39, observed m/z: 1555.5 ([M/3 + H]+)) | 11.002 | D |
| BCY12583 | calculated MW: 4703.38, observed m/z: 1568.6 ([M/3 + H]+), 1176.2([M/4 + H]+) | 11.017 | D |
| BCY12584 | Calculated MW: 5217.13, observed m/z: 1305.1 [M/4 + H]+, 1739.8 [M/3 + H]+) | 12.954 | B |
| BCY12585 | calculated MW: 4735.45, observed m/z: 1578.8 ([M/3 + H]+ | 14.077 | A |
| BCY12709 | Calculated MW: 4624.32, observed m/z: 925.5 [M/5 + H]+, 1156.7 [M/4 + H]+, 1541.8 [M/3 + H]+) | 10.749 | D |
| BCY12710 | Calculated MW: 4624.32, observed m/z: 925.6 [M/5 + H]+, 1157.3 [M/4 + H]+, 1541.9 [M/3 + H]+ | 13.832 | A |
| BCY11468 | calculated MW: 6783.93, observed m/z: 1131.7([M/6 + H]+ | 10.29 | B |
| BCY11618 | calculated MW: 5029.97, observed m/z: 1257.8([M/4 + H]+) and 1006.6([M/5 + H]+ | 8.89 | E |
| BCY11776 | calculated MW: 5031.91, observed m/z: 1258.52([M/4 + H]+) and 1006.7([M/5 + H]+) | 12.598 | E |
| BCY11860 | m/z (MW: 5617.56, observed m/z: 1404.56 ([(M/4 + H+]) | 10.166 | F |
| BCY12020 | calculated MW: 5709.68, observed m/z: 1902.80([M/3 + H]+), 1427.56([M/4 + H]+ | 14.108 | B |
| BCY12661 | calculated MW: 5374.21, observed m/z: 1344.5 ([M/4 + H]+) | 12.408 | B |
| BCY12969 | Calculated MW: 5176.04, observed m/z: 1035.7 [M/5 + H]+, 1294.9 [M/4 + H]+, 1726.8 [M/3 + H]+) | 13.147 | B |

Biological Data

1. CD137 Reporter Assay Co-Culture with Tumour Cells

Culture medium, referred to as R1 media, is prepared by adding 1% FBS to RPMI-1640 (component of Promega kit CS196005). Serial dilutions of test articles in R1 are prepared in a sterile 96 well-plate. Add 25 μL per well of test articles or R1 (as a background control) to designated wells in a white cell culture plate. Tumour cells* are harvested and resuspended at a concentration of 400,000 cells/mL in R1 media. Twenty five (25) μL/well of tumour cells are added to the white cell culture plate. Jurkat cells (Promega kit CS196005, 0.5 mL) are thawed in the water bath and then added to 5 ml pre-warmed R1 media. Twenty five (25) μL/well of Jurkat cells are then added to the white cell culture plate. Incubate the cells and test articles for 6 h at 37° C., 5% $CO_2$. At the end of 6 h, add 75 μL/well Bio-Glo™ reagent (Promega) and incubate for 10 min before reading luminescence in a plate reader (Clariostar, BMG). The fold change relative to cells alone (Jurkat cells+Cell line used in co-culture) is calculated and plotted in GraphPad Prism as log(agonist) vs response to determine EC50 (nM) and Fold Induction over background (Max).

The tumour cell type used in co-culture is NCI-H292 which has been shown to express Nectin-4. The tumour cell type used in co-culture for EphA2 is PC3. The tumour cell type used in co-culture for PD-L1 is RKO.

A summary of the fold induction induced by Nectin-4/CD137 heterotandem peptides in the CD137 reporter coculture assay with NCI-H292 cells is shown in Table 1. All compounds are compared to plate control BCY10000 which has an average EC50 of 1.1±0.5 nM and Emax of 28±11 fold over background.

TABLE 1

Fold induction induced by Nectin-4/CD137 heterotandem bicyclic peptide complexes in a CD137 reporter assay

| Complex ID | Fold improvement in EC50 over BCY10000 on same plate | Fold improvement in Emax over BCY10000 on same plate |
|---|---|---|
| BCY11616 | 0.21 | 1.22 |
| BCY12377 | 0.78 | 1.37 |
| BCY12379 | 0.91 | 1.29 |

TABLE 1-continued

Fold induction induced by Nectin-4/CD137 heterotandem bicyclic peptide complexes in a CD137 reporter assay

| Complex ID | Fold improvement in EC50 over BCY10000 on same plate | Fold improvement in Emax over BCY10000 on same plate |
|---|---|---|
| BCY12572 | 0.35 | 1.67 |
| BCY12573 | 0.74 | 1.34 |
| BCY12574 | 0.22 | 0.77 |
| BCY12575 | 0.73 | 0.35 |
| BCY12576 | 0.23 | 1.45 |
| BCY12577 | 0.25 | 1.06 |
| BCY12578 | 0.05 | 0.93 |
| BCY12579 | 0.29 | 1.07 |
| BCY12580 | 0.64 | 0.97 |
| BCY12581 | 1.35 | 0.88 |
| BCY12582 | 1.69 | 1.32 |
| BCY12583 | 0.60 | 1.47 |
| BCY12585 | 1.31 | 1.50 |
| BCY12709 | 0.08 | 2.15 |
| BCY12710 | 0.16 | 1.41 |
| BCY11468 | 0.45 | 0.68 |
| BCY11618 | 0.09 | 2.59 |
| BCY11776 | 0.05 | 0.07 |
| BCY11860 | 0.29 | 1.53 |
| BCY12020 | 0.15 | 0.48 |
| BCY12661 | 0.34 | 0.50 |

A summary of the fold induction induced by EphA2/CD137 heterotandem peptides in the CD137 reporter coculture assay with PC3 cells is shown in Table 2. All compounds are compared to plate control BCY9173 which has an average EC50 of 0.54 nM and Emax of 42 fold over background.

TABLE 2

Fold induction induced by EphA2/CD137 heterotandem bicyclic peptide complexes in a CD137 reporter assay

| Complex ID | Cell line | Fold improvement in EC50 over BCY9173 on same plate | Fold improvement in Emax over BCY9173 on same plate |
|---|---|---|---|
| BCY12233 | PC3 | 1.0 | 0.9 |
| BCY12234 | PC3 | 1.0 | 0.8 |
| BCY12235 | PC3 | 1.1 | 0.8 |
| BCY12236 | PC3 | 1.4 | 0.8 |
| BCY12237 | PC3 | 1.0 | 0.8 |

A summary of the fold induction induced by PD-L1/CD137 heterotandem peptides in the CD137 reporter coculture assay with RKO cells is shown in Table 3.

TABLE 3

Fold induction induced by PD-L1/CD137 heterotandem bicyclic peptide complexes in a CD137 reporter assay

| Bicycle ID | EC50(nM) | Fold Induction over background |
|---|---|---|
| BCY12229 | 18 | 8 |
| BCY12230 | 46 | 10 |
| BCY12242 | 20 | 13 |
| BCY12375 | 22 | 3 |

2. Pharmacokinetics of CD137 Heterotandem Bicyclic Peptide Complexes in SD Rats

Male SD Rats were dosed with 2 mg/kg of each heterotandem Bicycle peptide complex formulated in 25 mM Histidine HCl, 10% sucrose pH 7. Serial bleeding (about 80 µL blood/time point) was performed via submadibular or saphenous vein at each time point. All blood samples were immediately transferred into prechilled microcentrifuge tubes containing 2 µL K2-EDTA (0.5M) as anti-coagulant and placed on wet ice. Blood samples were immediately processed for plasma by centrifugation at approximately 4° C., 3000 g. The precipitant including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 µL of the supernatant samples were directly injected for LC-MS/MS analysis using an Orbitrap Q Exactive in positive ion mode to determine the concentrations of Bicycle. Plasma concentration versus time data were analyzed by non-compartmental approaches using the Phoenix WinNonlin 6.3 software program. C0, Cl, Vdss, T½, AUC(0-last), AUC(0-inf), MRT(0-last), MRT(0-inf) and graphs of plasma concentration versus time profile were reported. The pharmacokinetic parameters from the experiment are as shown in Table 4:

TABLE 4

Pharmacokinetic Parameters in SD Rats

| Compound | Dosing Route | Dose (mg/kg) | T½(h) | Vdss (L/kg) | Clp (ml/min/kg) |
|---|---|---|---|---|---|
| BCY12234 | IV Inf | 2.0 | 0.42 | 0.95 | 26 |
| BCY13035 | IV Inf | 3.0 | 1.5 | 0.63 | 11 |
| BCY13040 | IV Inf | 3.0 | 1.6 | 0.63 | 10 |

The invention claimed is:

1. A heterotandem bicyclic peptide complex comprising:
(a) a first peptide ligand which binds to a component present on a cancer cell; conjugated via a linker to
(b) a second peptide ligand which binds to a component present on an immune cell; wherein each of said peptide ligands comprise a polypeptide comprising at least three reactive groups, separated by at least two loop sequences, and a molecular scaffold which forms covalent bonds with the reactive groups of the polypeptide such that at least two polypeptide loops are formed on the molecular scaffold, characterized in that said heterotandem bicyclic peptide complex comprises the following first and second peptide ligands:

| Heterotandem Complex No. | First Peptide | Second Peptide |
|---|---|---|
| BCY12229 | [Ac]D[HArg]CSAGWLTMCQKLHLCPSH (SEQ ID NO: 1; BCY11865) | Ac-C[tBuAla]PE[D-Lys(PYA)]PYCFADPY[Nle]CA (SEQ ID NO: 67; BCY8928) |
| BCY12230 | [Ac]D[HArg]CSKGWLTMCQK(Ac)LHLCPSH (SEQ ID NO: 2; BCY11866) | Ac-C[tBuAla]PE[D-Lys(PYA)]PYCFADPY[Nle]CA (SEQ ID NO: 67; BCY8928) |
| BCY12231 | [Ac]D[HArg]CSAGWLTKCQK(Ac)LHLCPSH (SEQ ID NO: 3; BCY11867) | Ac-C[tBuAla]PE[D-Lys(PYA)]PYCFADPY[Nle]CA (SEQ ID NO: 67; BCY8928) |

-continued

| Heterotandem Complex No. | First Peptide | Second Peptide |
|---|---|---|
| BCY12232 | [Ac]D[HArg]CSAGWLTMCKK(Ac)LHLCPSH (SEQ ID NO: 4; BCY11868) | Ac-C[tBuAla]PE[D-Lys(PYA)]PYCFADPY[Nle]CA (SEQ ID NO: 67; BCY8928) |
| BCY12242 | [Ac]D[HArg]CSAGWLTMCQK(Ac)LKLCPSH (SEQ ID NO: 5; BCY11869) | Ac-C[tBuAla]PE[D-Lys(PYA)]PYCFADPY[Nle]CA (SEQ ID NO: 67; BCY8928) |
| BCY12375 | Ac-SDKCSAGWLTMCQK[PYA]LHLCPSH (SEQ ID NO: 6; BCY10861) | [Ac]C[tBuAla]EE(dK)PYCFADPY[Nle]C[Dap(PYA)] (SEQ ID NO: 68; BCY12023) |
| BCY12663 | [Ac]SD[HArg]CSAGWLTMCQ[HArg]LHLCPSHK (SEQ ID NO: 7; BCY12479) | Ac-C[tBuAla]PE[D-Lys(PYA)]PYCFADPY[Nle]CA (SEQ ID NO: 67; BCY8928) |
| BCY12796 | [Ac]SD[HArg]CSAGWLTMC[HArg]QLNLCPSHK (SEQ ID NO: 8; BCY12477) | Ac-C[tBuAla]PE[D-Lys(PYA)]PYCFADPY[Nle]CA (SEQ ID NO: 67; BCY8928) |
| BCY12021 | Ac-SDKCSAGWLTMCQK[PYA]LHLCPSH (SEQ ID NO: 9; BCY10861) | [Ac]C[tBuAla]PE[dK]PYCFADPY[Nle]C[Dap(PYA)] (SEQ ID NO: 69; BCY11144) |
| BCY12233 | [PYA]A[HArg]DC[HyP]LVNPLCLHP[dD]W[HArg]C (SEQ ID NO: 10; BCY11813) | Ac-C[tBuAla]PE[D-Lys]PYCFADPY[Nle]CA (SEQ ID NO: 70; BCY8920) |
| BCY12234 | [Ac]A[HArg]DC[HyP]LVNPLCLHP[dD]W[HArg]CK(PYA) (SEQ ID NO: 11; BCY11814) | Ac-C[tBuAla]PE[D-Lys]PYCFADPY[Nle]CA (SEQ ID NO: 70; BCY8920) |
| BCY12235 | [Ac]A[HArg]DC[HyP]LVNPLCLK(PYA)P[dD]W[HArg]C (SEQ ID NO: 12; BCY11815) | Ac-C[tBuAla]PE[D-Lys]PYCFADPY[Nle]CA (SEQ ID NO: 70; BCY8920) |
| BCY12236 | [Ac]A[HArg]DC[HyP]K(PYA)VNPLCLHP[dD]W[HArg]C (SEQ ID NO: 13; BCY11816) | Ac-C[tBuAla]PE[D-Lys]PYCFADPY[Nle]CA (SEQ ID NO: 70; BCY8920) |
| BCY12237 | [Ac]A[HArg]DC[HyP]LVNPLCK(PYA)HP[dD]W[HArg]C (SEQ ID NO: 14; BCY11817) | Ac-C[tBuAla]PE[D-Lys]PYCFADPY[Nle]CA (SEQ ID NO: 70; BCY8920) |
| BCY12711 | A[HArg]DC[HyP]LVNPLCLHP[dD]W[HArg]C (SEQ ID NO: 15; BCY9594) | [Ac]C[tBuAla]EE[dK(PYA)]PYCFADPY[Nle]C (SEQ ID NO: 71; BCY12143) |
| BCY12712 | A[HArg]DC[HyP]LVNPLCLHP[dD]W[HArg]C (SEQ ID NO: 15; BCY9594) | [Ac]C[tBuAla]PE[dK(PYA)]PYCFADPY[Nle]C (SEQ ID NO: 72; BCY12149) |
| BCY12713 | A[HArg]DC[HyP]LVNPLCLHP[dD]W[HArg]C (SEQ ID NO: 15; BCY9594) | [Ac]C[tBuAla]PE[dK(PYA)]PYCFANPY[Nle]C (SEQ ID NO: 73; BCY12147) |
| BCY12714 | A[HArg]DC[HyP]LVNPLCLHP[dD]W[HArg]C (SEQ ID NO: 15; BCY9594) | [Ac]C[tBuAla]PE[dK(PYA)]PYCFAEPY[Nle]C (SEQ ID NO: 74; BCY12145) |
| BCY12715 | A[HArg]DC[HyP]LVNPLCLHP[dD]W[HArg]C (SEQ ID NO: 15; BCY9594) | [Ac]C[tBuAla]PE[dK(PYA)]PYCFA[Aad]PY[Nle]C (SEQ ID NO: 75; BCY12146) |
| BCY12717 | A[HArg]DC[HyP]LVNPLCLHP[dD]W[HArg]C (SEQ ID NO: 15; BCY9594) | [Ac]C[tBuAla]PE[dK(PYA)]PYCFADPY[Nle][Cysteamine] (SEQ ID NO: 76; BCY12352) |
| BCY12718 | A[HArg]DC[HyP]LVNPLCLHP[dD]W[HArg]C (SEQ ID NO: 15; BCY9594) | [3-mercaptopropionic acid][tBuAla]PE[dK(PYA)]PYCFADPY[Nle]C (SEQ ID NO: 77; BCY12353) |
| BCY12719 | A[HArg]DC[HyP]LVNPLCLHP[dD]W[HArg]C (SEQ ID NO: 15; BCY9594) | [3-mercaptopropionic acid][tBuAla]PE[dK(PYA)]PYCFADPY[Nle][Cysteamine] (SEQ ID NO: 78; BCY12354) |
| BCY12720 | A[HArg]DC[HyP]LVNPLCLHP[dD]W[HArg]C (SEQ ID NO: 15; BCY9594) | Palmitic acid-yGly-yGlu-C[tBuAla]PE[dK(PYA)]PYCFADPY[Nle]C (SEQ ID NO: 79; BCY12360) |
| BCY12961 | [Ac]A[HArg]DC[HyP]LVNPLCLHP[dD]W[HArg]CK (SEQ ID NO: 16; BCY12734) | Ac-C[tBuAla]PE[D-Lys(PYA)]PYCFADPY[Nle]CA (SEQ ID NO: 67; BCY8928) |
| BCY12962 | [Ac]A[HArg]DC[HyP]LVNPLCLKP[dD]W[HArg]C (SEQ ID NO: 17; BCY12735) | Ac-C[tBuAla]PE[D-Lys(PYA)]PYCFADPY[Nle]CA (SEQ ID NO: 67; BCY8928) |
| BCY12963 | [Ac]A[HArg]DC[HyP]KVNPLCLHP[dD]W[HArg]C (SEQ ID NO: 18; BCY12736) | Ac-C[tBuAla]PE[D-Lys(PYA)]PYCFADPY[Nle]CA (SEQ ID NO: 67; BCY8928) |
| BCY12964 | [Ac]A[HArg]DC[HyP]LVNPLCKHP[dD]W[HArg]C (SEQ ID NO: 19; BCY12737) | Ac-C[tBuAla]PE[D-Lys(PYA)]PYCFADPY[Nle]CA (SEQ ID NO: 67; BCY8928) |

-continued

| Heterotandem Complex No. | First Peptide | Second Peptide |
|---|---|---|
| BCY12965 | A[HArg]DC[HyP]LVNPLCLHP[dE]W[HArg]C (SEQ ID NO: 20; BCY12738) | Ac-C[tBuAla]PE[D-Lys(PYA)]PYCFADPY[Nle]CA (SEQ ID NO: 67; BCY8928) |
| BCY12966 | A[HArg]EC[HyP]LVNPLCLHP[dE]W[HArg]C (SEQ ID NO: 21; BCY12739) | Ac-C[tBuAla]PE[D-Lys(PYA)]PYCFADPY[Nle]CA (SEQ ID NO: 67; BCY8928) |
| BCY13029 | A[HArg]DC[HyP]LVNPLCLEP[dD]W[HArg]C (SEQ ID NO: 22; BCY12854) | Ac-C[tBuAla]PE[D-Lys(PYA)]PYCFADPY[Nle]CA (SEQ ID NO: 67; BCY8928) |
| BCY13030 | A[HArg]DC[HyP]LVNPLCLHP[dD]WTC SEQ ID NO: 23; BCY12855) | Ac-C[tBuAla]PE[D-Lys(PYA)]PYCFADPY[Nle]CA (SEQ ID NO: 67; BCY8928) |
| BCY13031 | A[HArg]DC[HyP]LVNPLCLEP[dD]WTC SEQ ID NO: 24; BCY12856) | Ac-C[tBuAla]PE[D-Lys(PYA)]PYCFADPY[Nle]CA (SEQ ID NO: 67; BCY8928) |
| BCY13032 | A[HArg]DC[HyP]LVNPLCLEP[dD]WTC[dA] (SEQ ID NO: 25; BCY12857) | Ac-C[tBuAla]PE[D-Lys(PYA)]PYCFADPY[Nle]CA (SEQ ID NO: 67; BCY8928) |
| BCY13033 | A[HArg]DC[HyP]LVNPLCLEP[dA]WTC SEQ ID NO: 26; BCY12858) | Ac-C[tBuAla]PE[D-Lys(PYA)]PYCFADPY[Nle]CA (SEQ ID NO: 67; BCY8928) |
| BCY13034 | A[HArg]DC[HyP]LVNPLCL[33DPA]P[dD]WTC (SEQ ID NO: 27; BCY12859) | Ac-C[tBuAla]PE[D-Lys(PYA)]PYCFADPY[Nle]CA (SEQ ID NO: 67; BCY8928) |
| BCY13035 | C[HyP]LVNPLCL[33DPA]P[dD]WTC (SEQ ID NO: 28; BCY12860) | Ac-C[tBuAla]PE[D-Lys(PYA)]PYCFADPY[Nle]CA (SEQ ID NO: 67; BCY8928) |
| BCY13036 | C[HyP]LVNPLCLEP[dD]WTC[dA] (SEQ ID NO: 29; BCY12861) | Ac-C[tBuAla]PE[D-Lys(PYA)]PYCFADPY[Nle]CA (SEQ ID NO: 67; BCY8928) |
| BCY13037 | A[HArg]DC[HyP][Cba]VNPLCLHP[dD]W[HArg]C (SEQ ID NO: 30; BCY12862) | Ac-C[tBuAla]PE[D-Lys(PYA)]PYCFADPY[Nle]CA (SEQ ID NO: 67; BCY8928) |
| BCY13038 | A[HArg]DC[HyP][Cba]VNPLCLEP[dD]WTC (SEQ ID NO: 31; BCY12863) | Ac-C[tBuAla]PE[D-Lys(PYA)]PYCFADPY[Nle]CA (SEQ ID NO: 67; BCY8928) |
| BCY13039 | [dA][HArg]DC[HyP][Cba]VNPLCLEP[dD]WTC[dA] (SEQ ID NO: 32; BCY12864) | Ac-C[tBuAla]PE[D-Lys(PYA)]PYCFADPY[Nle]CA (SEQ ID NO: 67; BCY8928) |
| BCY13040 | C[HyP][Cba]VNPLCL[33DPA]P[dD]WTC[dA] (SEQ ID NO: 33; BCY12865) | Ac-C[tBuAla]PE[D-Lys(PYA)]PYCFADPY[Nle]CA (SEQ ID NO: 67; BCY8928) |
| BCY13041 | A[HArg]DC[HyP]LVNPLCL[33DPA]P[dD]W[HArg]C (SEQ ID NO: 34; BCY12866) | Ac-C[tBuAla]PE[D-Lys(PYA)]PYCFADPY[Nle]CA (SEQ ID NO: 67; BCY8928) |
| BCY13141 | A[HArg]DC[HyP]LVNPLCLEP[dD]WTC SEQ ID NO: 24; BCY12856) | [3-mercaptopropionic acid][tBuAla]PE[dK(PYA)]PYCFADPY[Nle]C (SEQ ID NO: 77; BCY12353) |
| BCY13142 | A[HArg]DC[HyP]LVNPLCLHP[dD]W[HArg]C (SEQ ID NO: 15; BCY9594) | [3-mercaptopropionic acid][tBuAla]EE[dK]PYCFADPY[Nle]C (SEQ ID NO: 80; BCY13137) |
| BCY13143 | A[HArg]DC[HyP]LVNPLCLEP[dD]WTC SEQ ID NO: 24; BCY12856) | [3-mercaptopropionic acid][tBuAla]EE[dK]PYCFADPY[Nle]C (SEQ ID NO: 80; BCY13137) |
| BCY13250 | A[HArg]DC[HyP]LVNPLCLHP[d1Nal]W[HArg]C (SEQ ID NO: 35; BCY13116) | Ac-C[tBuAla]PE[D-Lys(PYA)]PYCFADPY[Nle]CA (SEQ ID NO: 67; BCY8928) |
| BCY13251 | A[HArg]DC[HyP]LVNPLCL[1Nal]P[dD]W[HArg]C (SEQ ID NO: 36; BCY13117) | Ac-C [tBuAla]PE[D-Lys(PYA)]PYCFADPY[Nle]CA (SEQ ID NO: 67; BCY8928) |
| BCY13252 | A[HArg]DC[HyP]LVNPLCLEP[d1Nal]WTC (SEQ ID NO: 37; BCY13118) | Ac-C[tBuAla]PE[D-Lys(PYA)]PYCFADPY[Nle]CA (SEQ ID NO: 67; BCY8928) |
| BCY13253 | C[HyP]LVNPLCL[1Nal]P[dD]WTC (SEQ ID NO: 38; BCY13119) | Ac-C[tBuAla]PE[D-Lys(PYA)]PYCFADPY[Nle]CA (SEQ ID NO: 67; BCY8928) |
| BCY13254 | [Ac]C[HyP]LVNPLCL[33DPA]P[dD]WTC[dK] (SEQ ID NO: 39; BCY13120) | Ac-C[tBuAla]PE[D-Lys(PYA)]PYCFADPY[Nle]CA (SEQ ID NO: 67; BCY8928) |
| BCY13255 | [NMeAla][HArg]DC[HyP]LVNPLCLHP[dD]W[HArg]C (SEQ ID NO: 40; BCY13121) | Ac-C[tBuAla]PE[D-Lys(PYA)]PYCFADPY[Nle]CA (SEQ ID NO: 67; BCY8928) |

-continued

| Heterotandem Complex No. | First Peptide | Second Peptide |
|---|---|---|
| BCY13256 | [NMeAla][HArg]DC[HyP]LVNPLCLEP[dD]WTC (SEQ ID NO: 41; BCY13122) | Ac-C[tBuAla]PE[D-Lys(PYA)]PYCFADPY[Nle]CA (SEQ ID NO: 67; BCY8928) |
| BCY13257 | [dA][HArg]DC[HyP][Cba]VNPLCLEP[dA]WTC[dA] (SEQ ID NO: 42; BCY13123) | Ac-C[tBuAla]PE[D-Lys(PYA)]PYCFADPY[Nle]CA (SEQ ID NO: 67; BCY8928) |
| BCY13258 | [d1Nal][HArg]DC[HyP][Cba]VNPLCLEP[dA]WTC[dA] (SEQ ID NO: 43; BCY13124) | Ac-C[tBuAla]PE[D-Lys(PYA)]PYCFADPY[Nle]CA (SEQ ID NO: 67; BCY8928) |
| BCY13260 | [dA]EDC[HyP]LVNPLCLEP[dD]WTC SEQ ID NO: 44; BCY13126) | Ac-C[tBuAla]PE[D-Lys(PYA)]PYCFADPY[Nle]CA (SEQ ID NO: 67; BCY8928) |
| BCY13261 | [dA][dA]DC[HyP]LVNPLCLEP[dD]WTC (SEQ ID NO: 45; BCY13127) | Ac-C[tBuAla]PE[D-Lys(PYA)]PYCFADPY[Nle]CA (SEQ ID NO: 67; BCY8928) |
| BCY13262 | ADC[HyP]LVNPLCLEP[dD]WTC (SEQ ID NO: 46; BCY13128) | Ac-C[tBuAla]PE[D-Lys(PYA)]PYCFADPY[Nle]CA (SEQ ID NO: 67; BCY8928) |
| BCY13264 | A[HArg]DC[HyP][hGlu]VNPLCLHP[dD]W[HArg]C (SEQ ID NO: 47; BCY13130) | Ac-C[tBuAla]PE[D-Lys(PYA)]PYCFADPY[Nle]CA (SEQ ID NO: 67; BCY8928) |
| BCY13265 | A[HArg]DC[HyP]LVNPLC[hGlu]HP[dD]W[HArg]C (SEQ ID NO: 48; BCY13131) | Ac-C[tBuAla]PE[D-Lys(PYA)]PYCFADPY[Nle]CA (SEQ ID NO: 67; BCY8928) |
| BCY13266 | A[HArg]DC[HyP]LVNPLCL[hGlu]P[dD]W[HArg]C (SEQ ID NO: 49; BCY13132) | Ac-C[tBuAla]PE[D-Lys(PYA)]PYCFADPY[Nle]CA (SEQ ID NO: 67; BCY8928) |
| BCY13268 | A[HArg]DC[HyP]LVNPLCLHP[dNle]W[HArg]C (SEQ ID NO: 50; BCY13134) | Ac-C[tBuAla]PE[D-Lys(PYA)]PYCFADPY[Nle]CA (SEQ ID NO: 67; BCY8928) |
| BCY13269 | A[HArg]DC[HyP]LVNPLCL[Nle]P[dD]W[HArg]C (SEQ ID NO: 51; BCY13135) | Ac-C[tBuAla]PE[D-Lys(PYA)]PYCFADPY[Nle]CA (SEQ ID NO: 67; BCY8928) |
| BCY13340 | C[HyP][Cba]VNPLCL[33DPA]P[dD]WTC[dA] (SEQ ID NO: 33; BCY12865) | [3-mercaptopropionic acid][tBuAla]PE[dK(PYA)]PYCFADPY[Nle]C (SEQ ID NO: 77; BCY12353) |
| BCY13342 | C[HyP]LVNPLCL[33DPA]P[dD]WTC (SEQ ID NO: 28; BCY12860) | [3-mercaptopropionic acid][tBuAla]PE[dK(PYA)]PYCFADPY[Nle]C (SEQ ID NO: 77; BCY12353) |
| BCY11616 | CP[1Nal][dD]CM[HArg]DWSTP[HyP]WC (SEQ ID NO: 52; BCY8116) | Ac-ACIEE(D-K)(PYA)QYCFADPY(Nle)CA (SEQ ID NO: 81; BCY7744) |
| BCY12238 | [Ac]CP[1Nal][dK]CM[HArg]DWSTP[HyP]WC (SEQ ID NO: 53; BCY12024) | Ac-C[tBuAla]PE[D-Lys(PYA)]PYCFADPY[Nle]CA (SEQ ID NO: 67; BCY8928) |
| BCY12377 | CP[1Nal][dD]CM[HArg]DWSTP[HyP]WC (SEQ ID NO: 52; BCY8116) | [Ac]C[tBuAla]EE[dK(PYA)]PYCFADPY[Nle]C (SEQ ID NO: 71; BCY12143) |
| BCY12379 | CP[1Nal][dD]CM[HArg]DWSTP[HyP]WC (SEQ ID NO: 52; BCY8116) | [Ac]C[tBuAla]PE[dK(PYA)]PYCFADPY[Nle]C (SEQ ID NO: 72; BCY12149) |
| BCY12572 | CP[1Nal][dD]CM[HArg]DWSTP[HyP]WC (SEQ ID NO: 52; BCY8116) | [Ac]C[tBuAla]PE[dK(PYA)]PYCFADPY[Nle][Cysteamine] (SEQ ID NO: 76; BCY12352) |
| BCY12573 | CP[1Nal][dD]CM[HArg]DWSTP[HyP]WC (SEQ ID NO: 52; BCY8116) | [3-mercaptopropionic acid][tBuAla]PE[dK(PYA)]PYCFADPY[Nle]C (SEQ ID NO: 77; BCY12353) |
| BCY12574 | CP[1Nal][dD]CM[HArg]DWSTP[HyP]WC (SEQ ID NO: 52; BCY8116) | [3-mercaptopropionic acid][tBuAla]PE[dK(PYA)]PYCFADPY[Nle][Cysteamine] (SEQ ID NO: 78; BCY12354) |
| BCY12575 | CP[1Nal][dD]CM[HArg]DWSTP[HyP]WC (SEQ ID NO: 52; BCY8116) | Palmitic acid-yGly-yGlu-C[tBuAla]PE[dK(PYA)]PYCFADPY[Nle]C (SEQ ID NO: 79; BCY12360) |
| BCY12576 | [3-mercaptopropionic acid]P[1Nal][dK]CM[HArg]DWSTP[HyP]WC (SEQ ID NO: 54; BCY12363) | Ac-C[tBuAla]PE[D-Lys(PYA)]PYCFADPY[Nle]CA (SEQ ID NO: 67; BCY8928) |
| BCY12577 | [Ac]CP[1Nal][dK]CM[HArg]DWSTP[HyP]W[Cysteamine] (SEQ ID NO: 55; BCY12364) | Ac-C[tBuAla]PE[D-Lys(PYA)]PYCFADPY[Nle]CA (SEQ ID NO: 67; BCY8928) |

| Heterotandem Complex No. | First Peptide | Second Peptide |
|---|---|---|
| BCY12578 | [3-mercaptopropionic acid]P[1Nal][dK]CM[HArg]DWSTP[HyP]W[Cysteamine] (SEQ ID NO: 56; BCY12365) | Ac-C[tBuAla]PE[D-Lys(PYA)]PYCFADPY[Nle]CA (SEQ ID NO: 67; BCY8928) |
| BCY12579 | [Ac]CP[1Nal][dK]CM[HArg]HWSTP[HyP]WC (SEQ ID NO: 57; BCY12366) | Ac-C[tBuAla]PE[D-Lys(PYA)]PYCFADPY[Nle]CA (SEQ ID NO: 67; BCY8928) |
| BCY12580 | [Ac]CP[1Nal][dK]CM[HArg]EWSTP[HyP]WC (SEQ ID NO: 58; BCY12367) | Ac-C[tBuAla]PE[D-Lys(PYA)]PYCFADPY[Nle]CA (SEQ ID NO: 67; BCY8928) |
| BCY12581 | CP[1Nal][dE]CM[HArg]DWSTP[HyP]WC (SEQ ID NO: 59; BCY12368) | Ac-C[tBuAla]PE[D-Lys(PYA)]PYCFADPY[Nle]CA (SEQ ID NO: 67; BCY8928) |
| BCY12582 | CP[1Nal][dA]CM[HArg]DWSTP[HyP]WC (SEQ ID NO: 60; BCY12369) | Ac-C[tBuAla]PE[D-Lys(PYA)]PYCFADPY[Nle]CA (SEQ ID NO: 67; BCY8928) |
| BCY12583 | CP[1Nal][dE]CL[HArg]DWSTP[HyP]WC (SEQ ID NO: 61; BCY12370) | Ac-C[tBuAla]PE[D-Lys(PYA)]PYCFADPY[Nle]CA (SEQ ID NO: 67; BCY8928) |
| BCY12584 | Palmitic acid-yGlu-yGlu-CP[1Nal][dK]CM[HArg]DWSTP[HyP]WC (SEQ ID NO: 62; BCY12371) | Ac-C[tBuAla]PE[D-Lys(PYA)]PYCFADPY[Nle]CA (SEQ ID NO: 67; BCY8928) |
| BCY12585 | CP[1Nal][dE]CM[HArg]EWSTP[HyP]WC (SEQ ID NO: 63; BCY12384) | Ac-C[tBuAla]PE[D-Lys(PYA)]PYCFADPY[Nle]CA (SEQ ID NO: 67; BCY8928) |
| BCY12709 | CP[1Nal][dD]CM[HArg]DWSTP[HyP]WC (SEQ ID NO: 52; BCY8116) | [Ac]C[tBuAla]PE[dK(PYA)]PYCFAD[NMeAla]Y[Nle]C (SEQ ID NO: 82; BCY12381) |
| BCY12710 | CP[1Nal][dD]CM[HArg]DWSTP[HyP]WC (SEQ ID NO: 52; BCY8116) | [Ac]C[tBuAla]PE[dK(PYA)]PYCFAD[NMeDAla]Y[Nle]C (SEQ ID NO: 83; BCY12382) |
| BCY11468 | [PYA][B-AlalCP[1Nal][dD]CM[HArg]DWSTP[HyP]WC (SEQ ID NO: 64; BCY11016) | Ac-C[tBuAla]PE[D-Lys(PYA)]PYCFADPY[Nle]CA (SEQ ID NO: 67; BCY8928) |
| BCY11618 | [PYA][B-Ala]CP[1Nal][dK]CM[HArg]DWSTP[HyP]WC (SEQ ID NO: 65; BCY11143) | Ac-C[tBuAla]PE[D-Lys]PYCFADPY[Nle]CA (SEQ ID NO: 70; BCY8920) |
| BCY11776 | CP[1Nal][dD]CM[HArg]DWSTP[HyP]WC (SEQ ID NO: 52; BCY8116) | [Ac]C[tBuAla]PE[dK]PYCFADPY[Nle]C[Dap(PYA)] (SEQ ID NO: 69; BCY11144) |
| BCY11860 | [PYA][B-Ala]CP[1Nal][dK]CM[HArg]DWSTP[HyP]WC (SEQ ID NO: 65; BCY11143) | Ac-C[tBuAla]PE[D-Lys]PYCFADPY[Nle]CA (SEQ ID NO: 70; BCY8920) |
| BCY12020 | [PYA][B-Ala]CP[1Nal][dD]CM[HArg]DWSTP[HyP]WC (SEQ ID NO: 64; BCY11016) | [Ac]C[tBuAla]PE[dK]PYCFADPY[Nle]C[Dap(PYA)] (SEQ ID NO: 69; BCY11144) |
| BCY12661 | [PYA[CP[1Nal][dD]CM[HArg]DWSTP[HyP]WC (SEQ ID NO: 66; BCY11015) | [Ac]C[tBuAla]EE(dK)PYCFADPY[Nle]C[Dap(PYA)] (SEQ ID NO: 68; BCY12023) |
| BCY12969 | CP[1Nal][dD]CM[HArg]DWSTP[HyP]WC (SEQ ID NO: 52; BCY8116) | [Ac]C[tBuAla]PE[dK(PYA)]PYCFADPY[Nle]C[1,2-diaminoethane] (SEQ ID NO: 84; BCY12358) | wherein 1Nal represents 1-naphthylalanine, HArg represents homoarginine, HyP represents hydroxyproline, B-Ala represents beta-alanine, PYA represents 4-pentynoic acid, 3,3-DPA represents 3,3-diphenylalanine, Cba represents β-cyclobutylalanine, hGlu represents homoglutamic acid, Nle represents norleucine, NMeAla represents N-methyl-alanine, tBuAla represents t-butyl-alanine, Aad represents alpha-L-aminoadipic acid, Ac represents an acetyl group, Dap represents diaminopropionic acid, or a pharmaceutically acceptable salt thereof.

2. The heterotandem bicyclic peptide complex as defined in claim 1, wherein the immune cell is selected from: white blood cells, lymphocytes CD8 cells, CD4 cells, dendritic cells, follicular dendritic cells and granulocytes.

3. The heterotandem bicyclic peptide complex as defined in claim 2, wherein the lymphocytes are selected from T lymphocytes or T cells, B cells, or natural killer cells.

4. The heterotandem bicyclic peptide complex as defined in claim 1, wherein the second peptide ligand comprises a CD137 binding bicyclic peptide ligand.

5. The heterotandem bicyclic peptide complex as defined in claim 4, wherein the CD137 binding bicyclic peptide ligand is selected from any of the peptides of SEQ ID NOS: 67 to 84.

6. The heterotandem bicyclic peptide complex as defined in claim 1, wherein the first peptide ligand comprises a Nectin-4 binding bicyclic peptide ligand.

7. The heterotandem bicyclic peptide complex as defined in claim 6, wherein the Nectin-4 binding bicyclic peptide ligand is selected from any of the peptides of SEQ ID NOS: 52 to 66.

8. The heterotandem bicyclic peptide complex as defined in claim 6, which is selected from BCY11468, BCY11618, BCY11776, BCY11860, BCY12020, BCY12661 and BCY12969.

9. The heterotandem bicyclic peptide complex as defined in claim 1, wherein the first peptide ligand comprises an EphA2 binding bicyclic peptide ligand.

10. The heterotandem bicyclic peptide complex as defined in claim 9, wherein the EphA2 binding bicyclic peptide ligand is selected from any of the peptides of SEQ ID NOS: 10 to 51.

11. The heterotandem bicyclic peptide complex as defined in claim 9, which is selected from BCY13035, BCY13040, BCY13253, BCY13254, BCY13340 and BCY13342.

12. The heterotandem bicyclic peptide complex as defined in claim 1, wherein the first peptide ligand comprises a PD-L1 binding bicyclic peptide ligand.

13. The heterotandem bicyclic peptide complex as defined in claim 12, wherein the PD-L1 binding bicyclic peptide ligand is selected from any of the peptides of SEQ ID NOS: 1 to 9.

14. The heterotandem bicyclic peptide complex as defined in claim 12, which is selected from BCY12375 and BCY12021.

15. The heterotandem bicyclic peptide complex as defined in claim 1, wherein the molecular scaffold is 1,1',1''-(1,3,5-triazinane-1,3,5-triyl)triprop-2-en-1-one (TATA).

16. The heterotandem bicyclic peptide complex as defined in claim 1, wherein the pharmaceutically acceptable salt is selected from the free acid or the sodium, potassium, calcium, or ammonium salt.

17. A pharmaceutical composition which comprises the heterotandem bicyclic peptide complex of claim 1 in combination with one or more pharmaceutically acceptable excipients.

18. The heterotandem bicyclic peptide complex as defined in claim 1, wherein the linker is PEG-5:

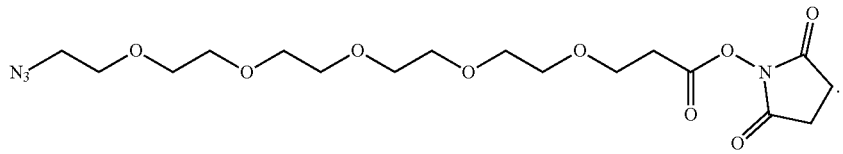 [SMILES: [N-]=[N+]=NCCOCCOCCOCCOCCOCCC(=O)ON1C(=O)CCC1=O]

19. The heterotandem bicyclic peptide complex as defined in claim 5, wherein the CD137 binding bicyclic peptide ligand is SEQ ID NO: 77.

20. The heterotandem bicyclic peptide complex as defined in claim 10, wherein the EphA2 binding bicyclic peptide ligand is SEQ ID NO: 33.

21. The heterotandem bicyclic peptide complex as defined in claim 11, which is BCY13340.

* * * * *

SEQUENCE LISTING

<160> NUMBER OF SEQ ID NOS: 84

<210> SEQ ID NO 1
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg

<400> SEQUENCE: 1

```
Asp Xaa Cys Ser Ala Gly Trp Leu Thr Met Cys Gln Lys Leu His Leu
1               5                   10                  15

Cys Pro Ser His
            20

<210> SEQ ID NO 2
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg

<400> SEQUENCE: 2

Asp Xaa Cys Ser Lys Gly Trp Leu Thr Met Cys Gln Lys Leu His Leu
1               5                   10                  15

Cys Pro Ser His
            20

<210> SEQ ID NO 3
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg

<400> SEQUENCE: 3

Asp Xaa Cys Ser Ala Gly Trp Leu Thr Lys Cys Gln Lys Leu His Leu
1               5                   10                  15

Cys Pro Ser His
            20

<210> SEQ ID NO 4
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg

<400> SEQUENCE: 4

Asp Xaa Cys Ser Ala Gly Trp Leu Thr Met Cys Lys Lys Leu His Leu
1               5                   10                  15

Cys Pro Ser His
            20

<210> SEQ ID NO 5
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg

<400> SEQUENCE: 5
```

```
Asp Xaa Cys Ser Ala Gly Trp Leu Thr Met Cys Gln Lys Leu Lys Leu
1               5                   10                  15

Cys Pro Ser His
            20

<210> SEQ ID NO 6
<211> LENGTH: 21
<212> TYPE: PRT
<213> ORGANISM: Artificial
<220> FEATURE:
<223> OTHER INFORMATION: Synthetic Peptide

<400> SEQUENCE: 6

Ser Asp Lys Cys Ser Ala Gly Trp Leu Thr Met Cys Gln Lys Leu His
1               5                   10                  15

Leu Cys Pro Ser His
                20

<210> SEQ ID NO 7
<211> LENGTH: 22
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is HArg
<220> FEATURE:
<221> NAME/KEY: Xaa
<222> LOCATION: (14)..(14)
<223> OTHER INFORMATION: Xaa is HArg

<400> SEQUENCE: 7

Ser Asp Xaa Cys Ser Ala Gly Trp Leu Thr Met Cys Gln Xaa Leu His
1               5                   10                  15

Leu Cys Pro Ser His Lys
                20

<210> SEQ ID NO 8
<211> LENGTH: 22
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is HArg
<220> FEATURE:
<221> NAME/KEY: Xaa
<222> LOCATION: (13)..(13)
<223> OTHER INFORMATION: Xaa is HArg

<400> SEQUENCE: 8

Ser Asp Xaa Cys Ser Ala Gly Trp Leu Thr Met Cys Xaa Gln Leu Asn
1               5                   10                  15

Leu Cys Pro Ser His Lys
                20

<210> SEQ ID NO 9
<211> LENGTH: 21
<212> TYPE: PRT
<213> ORGANISM: Artificial
<220> FEATURE:
<223> OTHER INFORMATION: Synthetic Peptide
```

```
<400> SEQUENCE: 9

Ser Asp Lys Cys Ser Ala Gly Trp Leu Thr Met Cys Gln Lys Leu His
1               5                  10                  15

Leu Cys Pro Ser His
            20

<210> SEQ ID NO 10
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 10

Ala Xaa Asp Cys Xaa Leu Val Asn Pro Leu Cys Leu His Pro Asp Trp
1               5                  10                  15

Xaa Cys

<210> SEQ ID NO 11
<211> LENGTH: 19
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 11

Ala Xaa Asp Cys Xaa Leu Val Asn Pro Leu Cys Leu His Pro Asp Trp
1               5                  10                  15

Xaa Cys Lys

<210> SEQ ID NO 12
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
```

<222> LOCATION: (17)..(17)
<223> OTHER INFORMATION: Xaa is HArg

<400> SEQUENCE: 12

Ala Xaa Asp Cys Xaa Leu Val Asn Pro Leu Cys Leu Lys Pro Asp Trp
1               5                   10                  15

Xaa Cys

<210> SEQ ID NO 13
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 13

Ala Xaa Asp Cys Xaa Lys Val Asn Pro Leu Cys Leu His Pro Asp Trp
1               5                   10                  15

Xaa Cys

<210> SEQ ID NO 14
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 14

Ala Xaa Asp Cys Xaa Leu Val Asn Pro Leu Cys Lys His Pro Asp Trp
1               5                   10                  15

Xaa Cys

<210> SEQ ID NO 15
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP

```
<220> FEATURE:
<221> NAME/KEY: Xaa
<222> LOCATION: (17)..(17)
<223> OTHER INFORMATION: Xaa is HArg

<400> SEQUENCE: 15

Ala Xaa Asp Cys Xaa Leu Val Asn Pro Leu Cys Leu His Pro Asp Trp
 1               5                  10                  15

Xaa Cys

<210> SEQ ID NO 16
<211> LENGTH: 19
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 16

Ala Xaa Asp Cys Xaa Leu Val Asn Pro Leu Cys Leu His Pro Asp Trp
 1               5                  10                  15

Xaa Cys Lys

<210> SEQ ID NO 17
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 17

Ala Xaa Asp Cys Xaa Leu Val Asn Pro Leu Cys Leu Lys Pro Asp Trp
 1               5                  10                  15

Xaa Cys

<210> SEQ ID NO 18
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
```

<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 18

Ala Xaa Asp Cys Xaa Lys Val Asn Pro Leu Cys Leu His Pro Asp Trp
1               5                   10                  15

Xaa Cys

<210> SEQ ID NO 19
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 19

Ala Xaa Asp Cys Xaa Leu Val Asn Pro Leu Cys Lys His Pro Asp Trp
1               5                   10                  15

Xaa Cys

<210> SEQ ID NO 20
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 20

Ala Xaa Asp Cys Xaa Leu Val Asn Pro Leu Cys Leu His Pro Glu Trp
1               5                   10                  15

Xaa Cys

<210> SEQ ID NO 21
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg

```
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 21

Ala Xaa Glu Cys Xaa Leu Val Asn Pro Leu Cys Leu His Pro Glu Trp
1               5                   10                  15

Xaa Cys

<210> SEQ ID NO 22
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 22

Ala Xaa Asp Cys Xaa Leu Val Asn Pro Leu Cys Leu Glu Pro Asp Trp
1               5                   10                  15

Xaa Cys

<210> SEQ ID NO 23
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP

<400> SEQUENCE: 23

Ala Xaa Asp Cys Xaa Leu Val Asn Pro Leu Cys Leu His Pro Asp Trp
1               5                   10                  15

Thr Cys

<210> SEQ ID NO 24
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
```

```
<222> LOCATION: (5)..(5)
<223> OTHER INFORMATION: Xaa is HyP

<400> SEQUENCE: 24

Ala Xaa Asp Cys Xaa Leu Val Asn Pro Leu Cys Leu Glu Pro Asp Trp
1               5                   10                  15

Thr Cys

<210> SEQ ID NO 25
<211> LENGTH: 19
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP

<400> SEQUENCE: 25

Ala Xaa Asp Cys Xaa Leu Val Asn Pro Leu Cys Leu Glu Pro Asp Trp
1               5                   10                  15

Thr Cys Ala

<210> SEQ ID NO 26
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP

<400> SEQUENCE: 26

Ala Xaa Asp Cys Xaa Leu Val Asn Pro Leu Cys Leu Glu Pro Ala Trp
1               5                   10                  15

Thr Cys

<210> SEQ ID NO 27
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (13)..(13)
<223> OTHER INFORMATION: Xaa is 3,3-DPA

<400> SEQUENCE: 27

Ala Xaa Asp Cys Xaa Leu Val Asn Pro Leu Cys Leu Xaa Pro Asp Trp
```

-continued

```
1               5                   10                  15

Thr Cys

<210> SEQ ID NO 28
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HyP
<220> FEATURE:
<221> NAME/KEY: Xaa
<222> LOCATION: (10)..(10)
<223> OTHER INFORMATION: Xaa is 3,3-DPA

<400> SEQUENCE: 28

Cys Xaa Leu Val Asn Pro Leu Cys Leu Xaa Pro Asp Trp Thr Cys
1               5                   10                  15

<210> SEQ ID NO 29
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HyP

<400> SEQUENCE: 29

Cys Xaa Leu Val Asn Pro Leu Cys Leu Glu Pro Asp Trp Thr Cys Ala
1               5                   10                  15

<210> SEQ ID NO 30
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (6)..(6)
<223> OTHER INFORMATION: Xaa is Cba
<220> FEATURE:
<221> NAME/KEY: Xaa
<222> LOCATION: (17)..(17)
<223> OTHER INFORMATION: Xaa is HArg

<400> SEQUENCE: 30

Ala Xaa Asp Cys Xaa Xaa Val Asn Pro Leu Cys Leu His Pro Asp Trp
1               5                   10                  15

Xaa Cys

<210> SEQ ID NO 31
<211> LENGTH: 18
<212> TYPE: PRT
<213> ORGANISM: Artificial
<220> FEATURE:
```

<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (6)..(6)
<223> OTHER INFORMATION: Xaa is Cba

<400> SEQUENCE: 31

Ala Xaa Asp Cys Xaa Xaa Val Asn Pro Leu Cys Leu Glu Pro Asp Trp
1               5                   10                  15

Thr Cys

<210> SEQ ID NO 32
<211> LENGTH: 19
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (6)..(6)
<223> OTHER INFORMATION: Xaa is Cba

<400> SEQUENCE: 32

Ala Xaa Asp Cys Xaa Xaa Val Asn Pro Leu Cys Leu Glu Pro Asp Trp
1               5                   10                  15

Thr Cys Ala

<210> SEQ ID NO 33
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HyP
<220> FEATURE:
<221> NAME/KEY: Xaa
<222> LOCATION: (3)..(3)
<223> OTHER INFORMATION: Xaa is Cba
<220> FEATURE:
<221> NAME/KEY: Xaa
<222> LOCATION: (10)..(10)
<223> OTHER INFORMATION: Xaa is 3,3-DPA

<400> SEQUENCE: 33

Cys Xaa Xaa Val Asn Pro Leu Cys Leu Xaa Pro Asp Trp Thr Cys Ala
1               5                   10                  15

<210> SEQ ID NO 34
<211> LENGTH: 18
<212> TYPE: PRT
<213> ORGANISM: Artificial
<220> FEATURE:

```
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (13)..(13)
<223> OTHER INFORMATION: Xaa is 3,3-DPA
<220> FEATURE:
<221> NAME/KEY: Xaa
<222> LOCATION: (17)..(17)
<223> OTHER INFORMATION: Xaa is HArg

<400> SEQUENCE: 34

Ala Xaa Asp Cys Xaa Leu Val Asn Pro Leu Cys Leu Xaa Pro Asp Trp
1               5                   10                  15

Xaa Cys

<210> SEQ ID NO 35
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (15)..(15)
<223> OTHER INFORMATION: Xaa is d1Nal
<220> FEATURE:
<221> NAME/KEY: Xaa
<222> LOCATION: (17)..(17)
<223> OTHER INFORMATION: Xaa is HArg

<400> SEQUENCE: 35

Ala Xaa Asp Cys Xaa Leu Val Asn Pro Leu Cys Leu His Pro Xaa Trp
1               5                   10                  15

Xaa Cys

<210> SEQ ID NO 36
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (13)..(13)
<223> OTHER INFORMATION: Xaa is d1Nal
<220> FEATURE:
<221> NAME/KEY: Xaa
<222> LOCATION: (17)..(17)
<223> OTHER INFORMATION: Xaa is HArg
```

<400> SEQUENCE: 36

Ala Xaa Asp Cys Xaa Leu Val Asn Pro Leu Cys Leu Xaa Pro Asp Trp
1               5                   10                  15
Xaa Cys

<210> SEQ ID NO 37
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (15)..(15)
<223> OTHER INFORMATION: Xaa is d1Nal

<400> SEQUENCE: 37

Ala Xaa Asp Cys Xaa Leu Val Asn Pro Leu Cys Leu Glu Pro Xaa Trp
1               5                   10                  15
Thr Cys

<210> SEQ ID NO 38
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HyP
<220> FEATURE:
<221> NAME/KEY: Xaa
<222> LOCATION: (10)..(10)
<223> OTHER INFORMATION: Xaa is 1Nal

<400> SEQUENCE: 38

Cys Xaa Leu Val Asn Pro Leu Cys Leu Xaa Pro Asp Trp Thr Cys
1               5                   10                  15

<210> SEQ ID NO 39
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HyP
<220> FEATURE:
<221> NAME/KEY: Xaa
<222> LOCATION: (10)..(10)
<223> OTHER INFORMATION: Xaa is 3,3-DPA

<400> SEQUENCE: 39

Cys Xaa Leu Val Asn Pro Leu Cys Leu Xaa Pro Asp Trp Thr Cys Lys
1               5                   10                  15

<210> SEQ ID NO 40

```
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is NMeAla
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (17)..(17)
<223> OTHER INFORMATION: Xaa is HArg

<400> SEQUENCE: 40

Xaa Xaa Asp Cys Xaa Leu Val Asn Pro Leu Cys Leu His Pro Asp Trp
1               5                   10                  15

Xaa Cys

<210> SEQ ID NO 41
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is NMeAla
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP

<400> SEQUENCE: 41

Xaa Xaa Asp Cys Xaa Leu Val Asn Pro Leu Cys Leu Glu Pro Asp Trp
1               5                   10                  15

Thr Cys

<210> SEQ ID NO 42
<211> LENGTH: 19
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (6)..(6)
<223> OTHER INFORMATION: Xaa is Cba

<400> SEQUENCE: 42

Ala Xaa Asp Cys Xaa Xaa Val Asn Pro Leu Cys Leu Glu Pro Ala Trp
```

<210> SEQ ID NO 43
<211> LENGTH: 19
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is d1Nal
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (6)..(6)
<223> OTHER INFORMATION: Xaa is Cba

<400> SEQUENCE: 43

Xaa Xaa Asp Cys Xaa Xaa Val Asn Pro Leu Cys Leu Glu Pro Ala Trp
1               5                   10                  15
Thr Cys Ala

<210> SEQ ID NO 44
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is HyP

<400> SEQUENCE: 44

Ala Glu Asp Cys Xaa Leu Val Asn Pro Leu Cys Leu Glu Pro Asp Trp
1               5                   10                  15
Thr Cys

<210> SEQ ID NO 45
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is HyP

<400> SEQUENCE: 45

Ala Ala Asp Cys Xaa Leu Val Asn Pro Leu Cys Leu Glu Pro Asp Trp
1               5                   10                  15
Thr Cys

<210> SEQ ID NO 46
<211> LENGTH: 17
<212> TYPE: PRT
<213> ORGANISM: Artificial
<220> FEATURE:

<223> OTHER INFORMATION: Synthetic Peptide
<220> FEATURE:
<221> NAME/KEY: Xaa
<222> LOCATION: (4)..(4)
<223> OTHER INFORMATION: Xaa is HyP

<400> SEQUENCE: 46

Ala Asp Cys Xaa Leu Val Asn Pro Leu Cys Leu Glu Pro Asp Trp Thr
1               5                   10                  15

Cys

<210> SEQ ID NO 47
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (6)..(6)
<223> OTHER INFORMATION: Xaa is hGlu
<220> FEATURE:
<221> NAME/KEY: Xaa
<222> LOCATION: (17)..(17)
<223> OTHER INFORMATION: Xaa is HArg

<400> SEQUENCE: 47

Ala Xaa Asp Cys Xaa Xaa Val Asn Pro Leu Cys Leu His Pro Asp Trp
1               5                   10                  15

Xaa Cys

<210> SEQ ID NO 48
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (12)..(12)
<223> OTHER INFORMATION: Xaa is hGlu
<220> FEATURE:
<221> NAME/KEY: Xaa
<222> LOCATION: (17)..(17)
<223> OTHER INFORMATION: Xaa is HArg

<400> SEQUENCE: 48

Ala Xaa Asp Cys Xaa Leu Val Asn Pro Leu Cys Xaa His Pro Asp Trp
1               5                   10                  15

Xaa Cys

<210> SEQ ID NO 49
<211> LENGTH: 18
<212> TYPE: PRT

```
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (13)..(13)
<223> OTHER INFORMATION: Xaa is hGlu
<220> FEATURE:
<221> NAME/KEY: Xaa
<222> LOCATION: (17)..(17)
<223> OTHER INFORMATION: Xaa is HArg

<400> SEQUENCE: 49

Ala Xaa Asp Cys Xaa Leu Val Asn Pro Leu Cys Leu Xaa Pro Asp Trp
1               5                   10                  15

Xaa Cys

<210> SEQ ID NO 50
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (15)..(15)
<223> OTHER INFORMATION: Xaa is dNle
<220> FEATURE:
<221> NAME/KEY: Xaa
<222> LOCATION: (17)..(17)
<223> OTHER INFORMATION: Xaa is HArg

<400> SEQUENCE: 50

Ala Xaa Asp Cys Xaa Leu Val Asn Pro Leu Cys Leu His Pro Xaa Trp
1               5                   10                  15

Xaa Cys

<210> SEQ ID NO 51
<211> LENGTH: 18
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (13)..(13)
<223> OTHER INFORMATION: Xaa is Nle
<220> FEATURE:
<221> NAME/KEY: Xaa
```

```
<222> LOCATION: (17)..(17)
<223> OTHER INFORMATION: Xaa is HArg

<400> SEQUENCE: 51

Ala Xaa Asp Cys Xaa Leu Val Asn Pro Leu Cys Leu Xaa Pro Asp Trp
1               5                   10                  15

Xaa Cys

<210> SEQ ID NO 52
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 52

Cys Pro Xaa Asp Cys Met Xaa Asp Trp Ser Thr Pro Xaa Trp Cys
1               5                   10                  15

<210> SEQ ID NO 53
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 53

Cys Pro Xaa Lys Cys Met Xaa Asp Trp Ser Thr Pro Xaa Trp Cys
1               5                   10                  15

<210> SEQ ID NO 54
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is proline modified with 3-
     mercaptopropionic acid
<220> FEATURE:
<221> NAME/KEY: Xaa
<222> LOCATION: (2)..(2)
<223> OTHER INFORMATION: Xaa is 1Nal
<220> FEATURE:
<221> NAME/KEY: Xaa
<222> LOCATION: (6)..(6)
```

```
<223> OTHER INFORMATION: Xaa is HArg
<220> FEATURE:
<221> NAME/KEY: Xaa
<222> LOCATION: (12)..(12)
<223> OTHER INFORMATION: Xaa is HyP

<400> SEQUENCE: 54

Xaa Xaa Lys Cys Met Xaa Asp Trp Ser Thr Pro Xaa Trp Cys
1               5                   10

<210> SEQ ID NO 55
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP
<220> FEATURE:
<221> NAME/KEY: Xaa
<222> LOCATION: (14)..(14)
<223> OTHER INFORMATION: Xaa is Tryptophan modified with Cysteamine

<400> SEQUENCE: 55

Cys Pro Xaa Lys Cys Met Xaa Asp Trp Ser Thr Pro Xaa Xaa
1               5                   10

<210> SEQ ID NO 56
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is proline modified with 3-
      mercaptopropionic acid
<220> FEATURE:
<221> NAME/KEY: Xaa
<222> LOCATION: (2)..(2)
<223> OTHER INFORMATION: Xaa is 1Nal
<220> FEATURE:
<221> NAME/KEY: Xaa
<222> LOCATION: (6)..(6)
<223> OTHER INFORMATION: Xaa is HArg
<220> FEATURE:
<221> NAME/KEY: Xaa
<222> LOCATION: (12)..(12)
<223> OTHER INFORMATION: Xaa is HyP
<220> FEATURE:
<221> NAME/KEY: Xaa
<222> LOCATION: (13)..(13)
<223> OTHER INFORMATION: Xaa is Tryptophan modified with Cysteamine

<400> SEQUENCE: 56

Xaa Xaa Lys Cys Met Xaa Asp Trp Ser Thr Pro Xaa Xaa
1               5                   10

<210> SEQ ID NO 57
<211> LENGTH: 15
<212> TYPE: PRT
<213> ORGANISM: Artificial
```

```
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 57

Cys Pro Xaa Lys Cys Met Xaa His Trp Ser Thr Pro Xaa Trp Cys
1               5                   10                  15

<210> SEQ ID NO 58
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 58

Cys Pro Xaa Lys Cys Met Xaa Glu Trp Ser Thr Pro Xaa Trp Cys
1               5                   10                  15

<210> SEQ ID NO 59
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 59

Cys Pro Xaa Glu Cys Met Xaa Asp Trp Ser Thr Pro Xaa Trp Cys
1               5                   10                  15

<210> SEQ ID NO 60
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
```

```
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 60

Cys Pro Xaa Ala Cys Met Xaa Asp Trp Ser Thr Pro Xaa Trp Cys
1               5                   10                  15

<210> SEQ ID NO 61
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 61

Cys Pro Xaa Glu Cys Leu Xaa Asp Trp Ser Thr Pro Xaa Trp Cys
1               5                   10                  15

<210> SEQ ID NO 62
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is yGlu modifed with palmitic acid
<220> FEATURE:
<221> NAME/KEY: Xaa
<222> LOCATION: (2)..(2)
<223> OTHER INFORMATION: Xaa is yGlu
<220> FEATURE:
<221> NAME/KEY: Xaa
<222> LOCATION: (5)..(5)
<223> OTHER INFORMATION: Xaa is 1Nal
<220> FEATURE:
<221> NAME/KEY: Xaa
<222> LOCATION: (9)..(9)
<223> OTHER INFORMATION: Xaa is HArg
<220> FEATURE:
<221> NAME/KEY: Xaa
<222> LOCATION: (15)..(15)
<223> OTHER INFORMATION: Xaa is HyP

<400> SEQUENCE: 62

Xaa Xaa Cys Pro Xaa Lys Cys Met Xaa Asp Trp Ser Thr Pro Xaa
1               5                   10                  15

Trp Cys

<210> SEQ ID NO 63
<211> LENGTH: 15
```

```
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 63

Cys Pro Xaa Glu Cys Met Xaa Glu Trp Ser Thr Pro Xaa Trp Cys
1               5                   10                  15

<210> SEQ ID NO 64
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is B-Ala modified with PYA
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (8)..(8)
<223> OTHER INFORMATION: Xaa is HArg
<220> FEATURE:
<221> NAME/KEY: Xaa
<222> LOCATION: (14)..(14)
<223> OTHER INFORMATION: Xaa is HyP

<400> SEQUENCE: 64

Xaa Cys Pro Xaa Asp Cys Met Xaa Asp Trp Ser Thr Pro Xaa Trp
1               5                   10                  15

Cys

<210> SEQ ID NO 65
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is B-Ala modified with PYA
<220> FEATURE:
<221> NAME/KEY: Xaa
<222> LOCATION: (4)..(4)
<223> OTHER INFORMATION: Xaa is 1Nal
<220> FEATURE:
<221> NAME/KEY: Xaa
<222> LOCATION: (8)..(8)
<223> OTHER INFORMATION: Xaa is HArg
<220> FEATURE:
<221> NAME/KEY: Xaa
<222> LOCATION: (14)..(14)
<223> OTHER INFORMATION: Xaa is HyP

<400> SEQUENCE: 65
```

-continued

```
Xaa Cys Pro Xaa Lys Cys Met Xaa Asp Trp Ser Thr Pro Xaa Trp
1               5                   10                  15

Cys

<210> SEQ ID NO 66
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is Cys modified with PYA
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 66

Xaa Pro Xaa Asp Cys Met Xaa Asp Trp Ser Thr Pro Xaa Trp Cys
1               5                   10                  15

<210> SEQ ID NO 67
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 67

Cys Xaa Pro Glu Xaa Pro Tyr Cys Phe Ala Asp Pro Tyr Xaa Cys Ala
1               5                   10                  15

<210> SEQ ID NO 68
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle
<220> FEATURE:
<221> NAME/KEY: Xaa
<222> LOCATION: (16)..(16)
<223> OTHER INFORMATION: Xaa is Dap(PYA)
```

```
<400> SEQUENCE: 68

Cys Xaa Glu Glu Lys Pro Tyr Cys Phe Ala Asp Pro Tyr Xaa Cys Xaa
1               5                   10                  15

<210> SEQ ID NO 69
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle
<220> FEATURE:
<221> NAME/KEY: Xaa
<222> LOCATION: (16)..(16)
<223> OTHER INFORMATION: Xaa is Dap(PYA)

<400> SEQUENCE: 69

Cys Xaa Pro Glu Lys Pro Tyr Cys Phe Ala Asp Pro Tyr Xaa Cys Xaa
1               5                   10                  15

<210> SEQ ID NO 70
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 70

Cys Xaa Pro Glu Lys Pro Tyr Cys Phe Ala Asp Pro Tyr Xaa Cys Ala
1               5                   10                  15

<210> SEQ ID NO 71
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 71

Cys Xaa Glu Glu Lys Pro Tyr Cys Phe Ala Asp Pro Tyr Xaa Cys
1               5                   10                  15

<210> SEQ ID NO 72
<211> LENGTH: 15
<212> TYPE: PRT
<213> ORGANISM: Artificial
<220> FEATURE:
<223> OTHER INFORMATION: Synthetic Peptide
```

```
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 72

Cys Xaa Pro Glu Lys Pro Tyr Cys Phe Ala Asp Pro Tyr Xaa Cys
1               5                   10                  15

<210> SEQ ID NO 73
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 73

Cys Xaa Pro Glu Lys Pro Tyr Cys Phe Ala Asn Pro Tyr Xaa Cys
1               5                   10                  15

<210> SEQ ID NO 74
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 74

Cys Xaa Pro Glu Lys Pro Tyr Cys Phe Ala Glu Pro Tyr Xaa Cys
1               5                   10                  15

<210> SEQ ID NO 75
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (11)..(11)
<223> OTHER INFORMATION: Xaa is Aad
<220> FEATURE:
<221> NAME/KEY: Xaa
<222> LOCATION: (14)..(14)
<223> OTHER INFORMATION: Xaa is Nle

<400> SEQUENCE: 75

Cys Xaa Pro Glu Lys Pro Tyr Cys Phe Ala Xaa Pro Tyr Xaa Cys
```

```
<210> SEQ ID NO 76
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle modified with Cysteamine

<400> SEQUENCE: 76

Cys Xaa Pro Glu Lys Pro Tyr Cys Phe Ala Asp Pro Tyr Xaa
1               5                   10

<210> SEQ ID NO 77
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is tBuAla modified with 3-mercaptopropionic
      acid
<220> FEATURE:
<221> NAME/KEY: Xaa
<222> LOCATION: (13)..(13)
<223> OTHER INFORMATION: Xaa is Nle

<400> SEQUENCE: 77

Xaa Pro Glu Lys Pro Tyr Cys Phe Ala Asp Pro Tyr Xaa Cys
1               5                   10

<210> SEQ ID NO 78
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is tBuAla modified with 3-mercaptopropionic
      acid
<220> FEATURE:
<221> NAME/KEY: Xaa
<222> LOCATION: (13)..(13)
<223> OTHER INFORMATION: Xaa is Nle modified with Cysteamine

<400> SEQUENCE: 78

Xaa Pro Glu Lys Pro Tyr Cys Phe Ala Asp Pro Tyr Xaa
1               5                   10

<210> SEQ ID NO 79
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is yGlu modified with Palmitic acid
<220> FEATURE:
```

```
<221> NAME/KEY: Xaa
<222> LOCATION: (2)..(2)
<223> OTHER INFORMATION: Xaa is yGlu
<220> FEATURE:
<221> NAME/KEY: Xaa
<222> LOCATION: (4)..(4)
<223> OTHER INFORMATION: Xaa is tBuAla
<220> FEATURE:
<221> NAME/KEY: Xaa
<222> LOCATION: (16)..(16)
<223> OTHER INFORMATION: Xaa is Nle

<400> SEQUENCE: 79

Xaa Xaa Cys Xaa Pro Glu Lys Pro Tyr Cys Phe Ala Asp Pro Tyr
1               5                   10                  15

Xaa Cys

<210> SEQ ID NO 80
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa is tBuAla modified with 3-mercaptopropionic
      acid
<220> FEATURE:
<221> NAME/KEY: Xaa
<222> LOCATION: (13)..(13)
<223> OTHER INFORMATION: Xaa is Nle

<400> SEQUENCE: 80

Xaa Glu Glu Lys Pro Tyr Cys Phe Ala Asp Pro Tyr Xaa Cys
1               5                   10

<210> SEQ ID NO 81
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (15)..(15)
<223> OTHER INFORMATION: Xaa is Nle

<400> SEQUENCE: 81

Ala Cys Ile Glu Glu Lys Gln Tyr Cys Phe Ala Asp Pro Tyr Xaa Cys
1               5                   10                  15

Ala

<210> SEQ ID NO 82
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (12)..(12)
<223> OTHER INFORMATION: Xaa is NMeAla
<220> FEATURE:
<221> NAME/KEY: Xaa
<222> LOCATION: (14)..(14)
<223> OTHER INFORMATION: Xaa is Nle
```

<400> SEQUENCE: 82

Cys Xaa Pro Glu Lys Pro Tyr Cys Phe Ala Asp Xaa Tyr Xaa Cys
1               5                   10                  15

<210> SEQ ID NO 83
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (12)..(12)
<223> OTHER INFORMATION: Xaa is NMeDAla
<220> FEATURE:
<221> NAME/KEY: Xaa
<222> LOCATION: (14)..(14)
<223> OTHER INFORMATION: Xaa is Nle

<400> SEQUENCE: 83

Cys Xaa Pro Glu Lys Pro Tyr Cys Phe Ala Asp Xaa Tyr Xaa Cys
1               5                   10                  15

<210> SEQ ID NO 84
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle
<220> FEATURE:
<221> NAME/KEY: Xaa
<222> LOCATION: (15)..(15)
<223> OTHER INFORMATION: Xaa is Cys modified with 1,2-diaminoethane

<400> SEQUENCE: 84

Cys Xaa Pro Glu Lys Pro Tyr Cys Phe Ala Asp Pro Tyr Xaa Xaa
1               5                   10                  15